United States Patent
Gao et al.

(10) Patent No.: US 12,030,935 B2
(45) Date of Patent: Jul. 9, 2024

(54) ANTI-PDGF-B ANTIBODIES AND PHARMACEUTICAL COMPOSITION THEREOF

(71) Applicant: Regeneron Pharmaceuticals, Inc., Tarrytown, NY (US)

(72) Inventors: Yinglin Gao, Upper Saddle River, NJ (US); Scott Macdonnell, New Milford, CT (US); Bharathi Sundaram, Yonkers, NY (US); Jee Kim, Ardsley, NY (US); Isabella Del Priore, Smithtown, NY (US); Jake Megna, Pine Bush, NY (US); Qin Ruan, Yorktown Heights, NY (US); Lori C. Morton, Chappaqua, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 17/583,930

(22) Filed: Jan. 25, 2022

(65) Prior Publication Data

US 2022/0242943 A1 Aug. 4, 2022

Related U.S. Application Data

(60) Provisional application No. 63/141,030, filed on Jan. 25, 2021.

(51) Int. Cl.
*A61K 39/395* (2006.01)
*A61P 9/12* (2006.01)
*A61P 43/00* (2006.01)
*C07K 16/22* (2006.01)
*C07K 16/24* (2006.01)

(52) U.S. Cl.
CPC ............... *C07K 16/22* (2013.01); *A61P 9/12* (2018.01); *A61P 43/00* (2018.01); *C07K 16/24* (2013.01); *C07K 2317/21* (2013.01); *C07K 2317/24* (2013.01); *C07K 2317/622* (2013.01); *C07K 2317/76* (2013.01)

(58) Field of Classification Search
None
See application file for complete search history.

(56) References Cited

FOREIGN PATENT DOCUMENTS

| WO | 2014/072876 A1 | 5/2014 |
| WO | 2016/075036 A1 | 5/2016 |

OTHER PUBLICATIONS

Andrae et al. Genes & Develop. 22: 1276-1312, 2008.*
Edwards et al. (J. Mol. Biol. 334: 103-118, 2003).*
Torres et al. (Trends in Immunol. 29(2): 91-97, 2008).*
Khan e tal. (J. Immunol. 192: 5398-5405, 2014).*
Poosarla et al. (Biotech. Bioengineer. 124(6): 1331-1342, 2017).*
Paul, Fundamental Immunology, 3rd Ed., 1993, pp. 292-295.*
Rudikoff et al. (PNAS 79: 1979-1983, 1982).*
De Pacalis et al. (J. Immunol. 169: 3076-3084, 2002).*
Casset et al. (Biochem. Biophys. Res. Comm. 307: 198-205, 2003).*
Chen et al. (J. Mol. Biol. 293: 865-881, 1999).*
Wu et al. (J. Mol. Biol. 294: 151-162, 1999).*
Maccallum et al. (J. Mol. Biol. 262: 732-745, 1996).*
Andrae et al., Role of platelet-derived growth factors in physiology and medicine. Genes Dev. May 15, 2008;22(10):1276-312.
Ghofrani et al., Imatinib for the Treatment of Pulmonary Arterial Hypertension. The New England Journal of Medicine. Sep. 29, 2005;353(13):1412-1413.
Prassler et al., In vitro affinity maturation of HuCAL antibodies: complementarity determining region exchange and RapMAT technology. Immunotherapy. Jul. 2009;1(4):571-83.

* cited by examiner

*Primary Examiner* — Christine J Saoud
(74) *Attorney, Agent, or Firm* — McCarter & English, LLP; Marcie B. Clarke

(57) ABSTRACT

The present disclosure provides anti-Platelet-Derived Growth Factor Subunit B (PDGF-B) antibodies, and antigen-binding fragments thereof, as well as methods of use of such antibodies, or antigen-binding fragments thereof, for treating a subject having pulmonary arterial hypertension (PAH).

9 Claims, 41 Drawing Sheets

Specification includes a Sequence Listing.

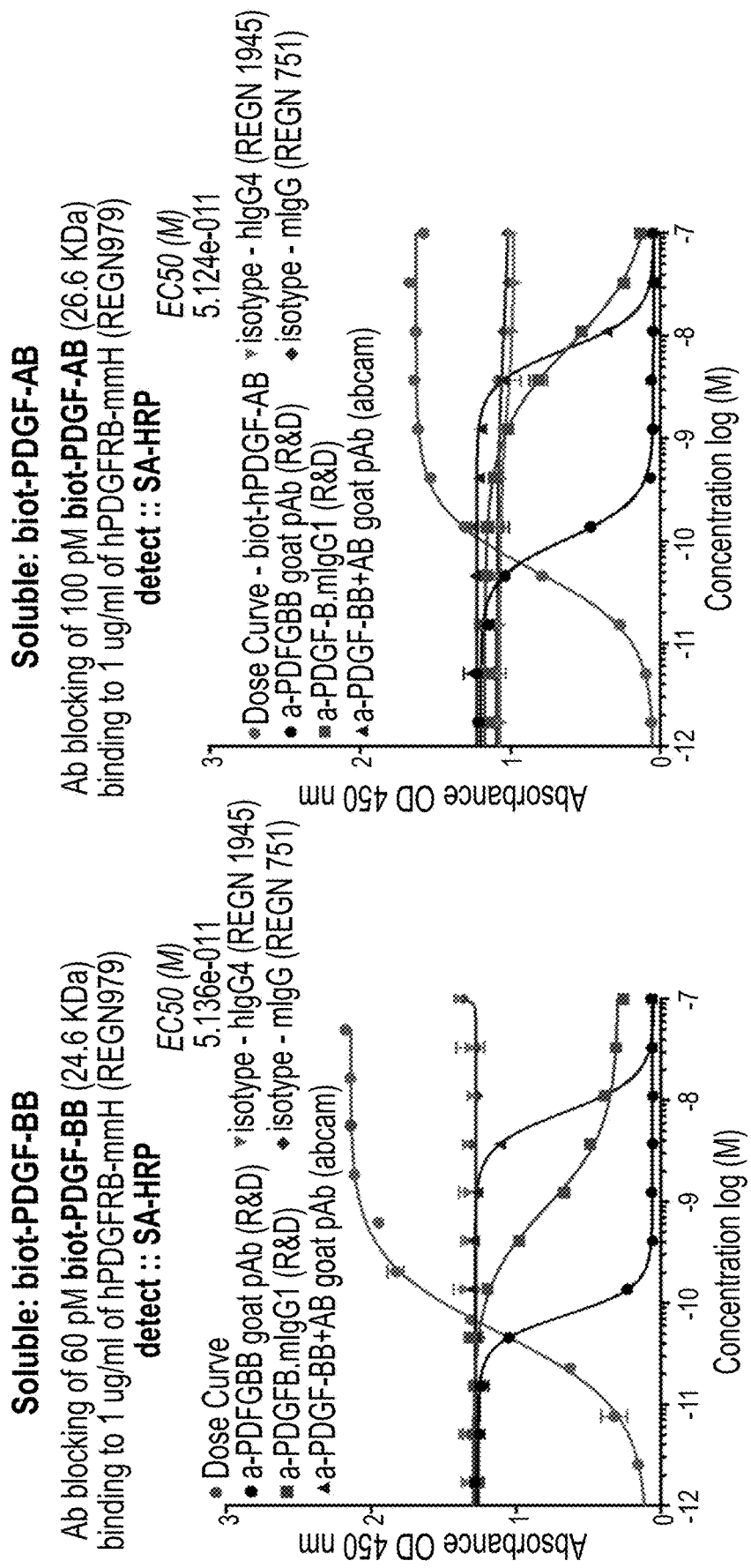

FIG. 4C

| AB PID | Ab blocking of 60pM Biot-PDGF-BB (dimer) on 1 ug/ml hPDGFRb-mmH, IC50 (M) | 100nM Ab blocking of 60pM Biot-PDGF-BB (dimer) on 1 ug/ml hPDGFRb-mmH, % blocking | Ab blocking of 100pM Biot-PDGF-AB (dimer) on 1 ug/ml hPDGFRb-mmH, IC50 (M) | 100nM Ab blocking of 100pM Biot-PDGF-AB (dimer) on 1 ug/ml hPDGFRb-mmH, % blocking |
|---|---|---|---|---|
| H4H13148P | 2.3E-10 | 102 | INC | 73 |
| H4H13145P | 3.0E-10 | 101 | 4.6E-09 | 97 |
| H4H13132P | 1.8E-09 | 96 | 1.4E-08 | 92 |
| H4H13162P | 5.5E-10 | 75 | NB | 1 |
| H4H13151P | 6.4E-10 | 90 | NB | -2 |
| H4H13157P | 2.8E-09 | 50 | 1.1E-07 | 57 |
| H4H13163P | 1.3E-08 | 48 | 1.9E-07 | 68 |
| H4H13167P | 6.4E-10 | 66 | NB | 2 |
| H4H13169P | 1.7E-09 | 67 | NB | 14 |
| H4H13155P | 2.6E-09 | 61 | NB | 2 |
| H4H13166P | 2.8E-09 | 50 | NB | 2 |
| H4H13127P | 5.1E-10 | 40 | 1.5E-08 | 29 |
| H4H13159P | 2.0E-08 | 29 | NB | 2 |
| H4H13143P | NB | 18 | NB | 13 |
| H4H13152P | NB | 3 | NB | -7 |
| H4H13170P | NB | 1 | NB | 1 |
| H4H13153P | NB | -17 | NB | -9 |
| CONTROLS | | | | |
| a-PDGF-BB+AB goat poly (abcam, ab34074) | 7.7E-09 | 103 | 7.4E-09 | 99 |
| a-PDGF-BB+AB goat poly (R&D, AF-220-NA) | 7.6E-11 | 102 | 1.1E-10 | 100 |
| a-PDGFB.mIgG1 (R&D, MAB1739) | 8.7E-10 | 87 | 8.0E-09 | 93 |
| isotype - hIgG4 (REGN 1945) | NB | -6 | NB | 21 |
| isotype - mIgG4 (REGN 751) | NB | -5 | NB | 18 |
| Theoretical bottom | <3.0E-11 | | <5.0E-11 | |
| Blocks>70% | | >70% | | >70% |
| Blockes between 45-70% | | 40-75% | | 40-75% |
| Block <25% - IC50 is not shown, considered to be Non-Blocker (NB) | | | | |

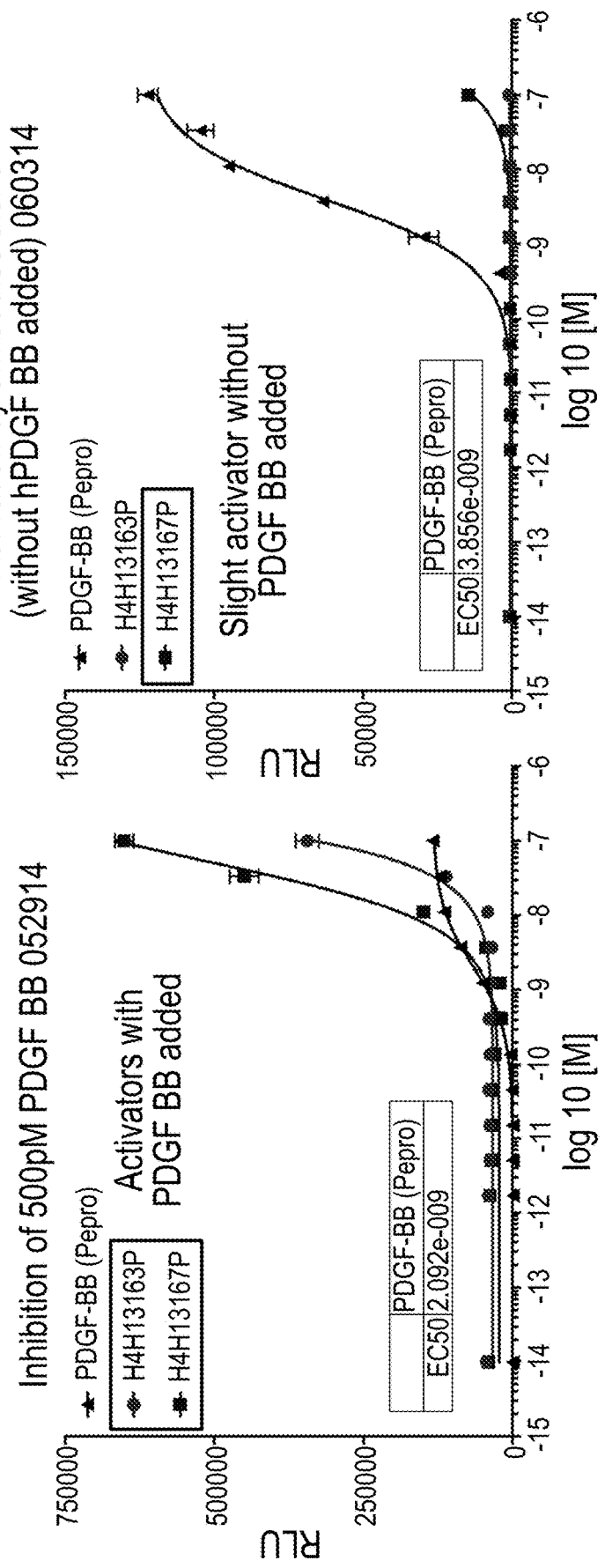

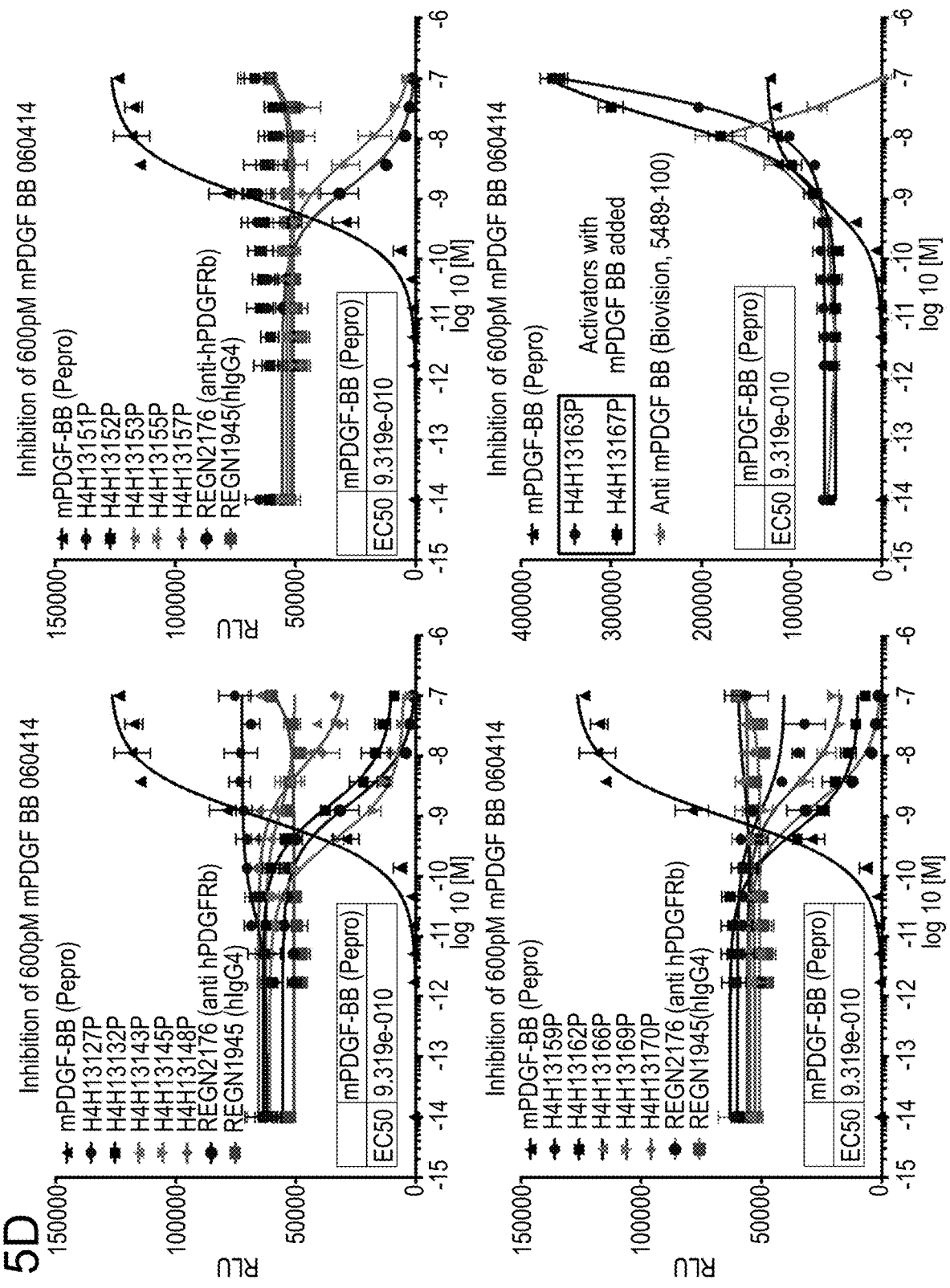

FIG. 8

| Ab PID # / REGN # | Lot # | Capture Surface Description | Human PDGF-BB homodimer (R&D) | | | | | Monkey PDGF-BB homodimer (Kingfisher) | | | | | Monkey PDGF-BB Fc homodimer-mouse Fc (IgG1) tag (Sino Biological) | | | | |
|---|---|---|---|---|---|---|---|---|---|---|---|---|---|---|---|---|---|
| | | | mAb Capture (RU) | 30nM hPDGF-BB (R&D) Bound (RU) | ka (1/Ms) | kd (1/s) | KD (M) | t½ (min) | mAb Capture (RU) | 30nM mfPDGF-BB (Kingfisher) Bound (RU) | ka (1/Ms) | kd (1/s) | KD (M) | t½ (min) | mAb Capture (RU) | 30nM mfPDGF-BB (Sino) Bound (RU) | ka (1/Ms) | kd (1/s) | KD (M) | t½ (min) |
| H4H13132P | L1 | Anti PDGF-B | 249 ± 1.7 | 48.4 | 2.60E+06 | 5.01E-05 | 1.93E-11 | 230.5 | 257.6 ± 1.5 | 50.3 | 4.31E+06 | 4.17E-05 | 9.67E-12 | 277.2 | 271.2 ± 2.6 | 116.7 | 4.09E+05 | 1.05E-05 | 2.56E-11 | 1102.3 |
| H4H13145P | L2 | Anti PDGF-B | 297.8 ± 21.5 | 62.2 | 1.09E+06 | 3.09E-05 | 2.82E-11 | 374.2 | 300.1 ± 13.5 | 73.4 | 9.30E+05 | 1.50E-05 | 1.61E-11 | 769.7 | 340 ± 11.4 | 151.5 | 4.04E+05 | 1.08E-05 | 2.68E-11 | 1066.7 |
| REGN1945 | L49 | Anti FelD1 | 356.7 ± 0.8 | 6.7 | NB | NB | NB | NB | 359.9 ± 1.1 | 6.8 | NB | NB | NB | NB | 367.4 ± 0.5 | -1.4 | NB | NB | NB | NB |

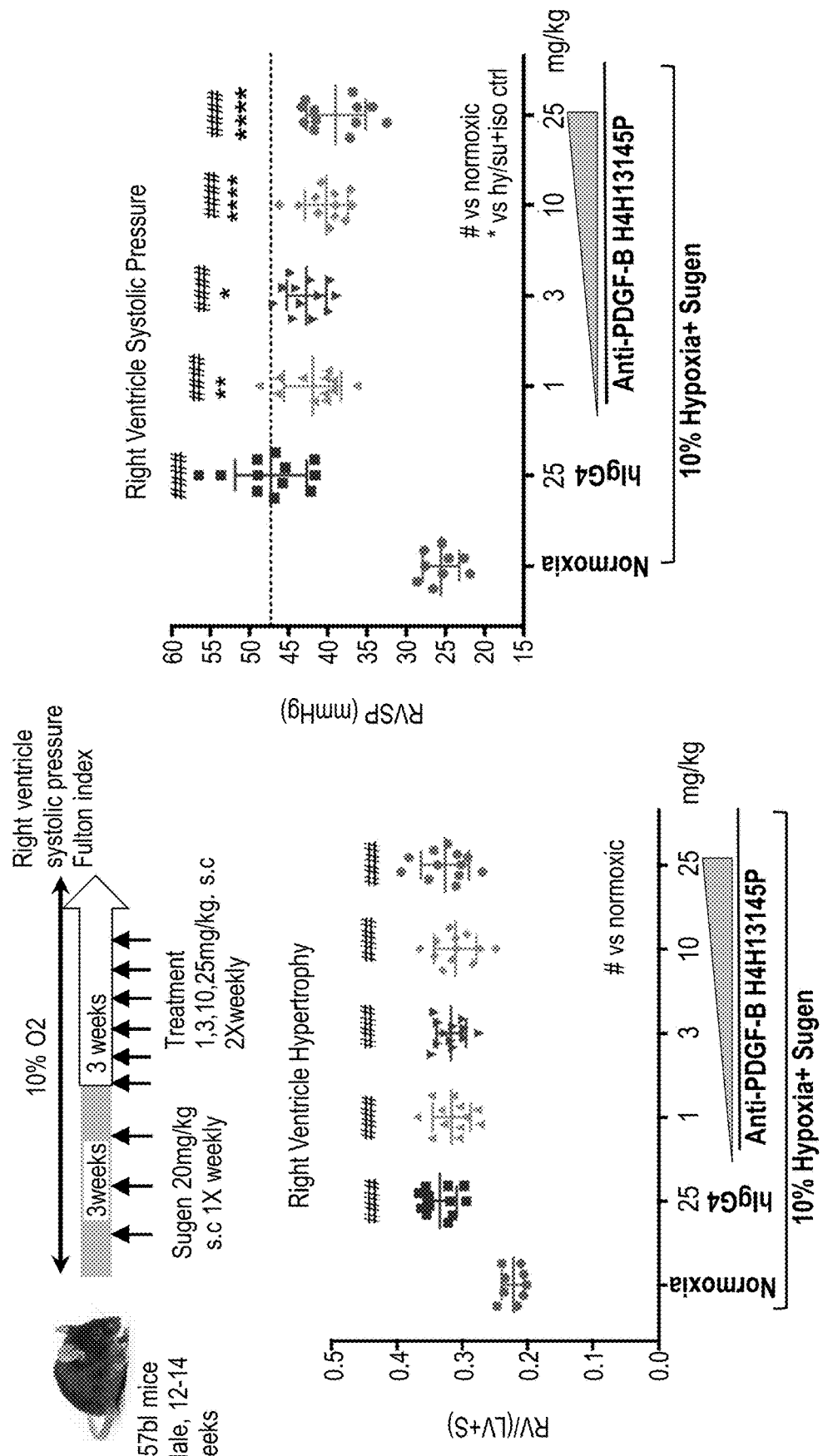

FIG. 13B
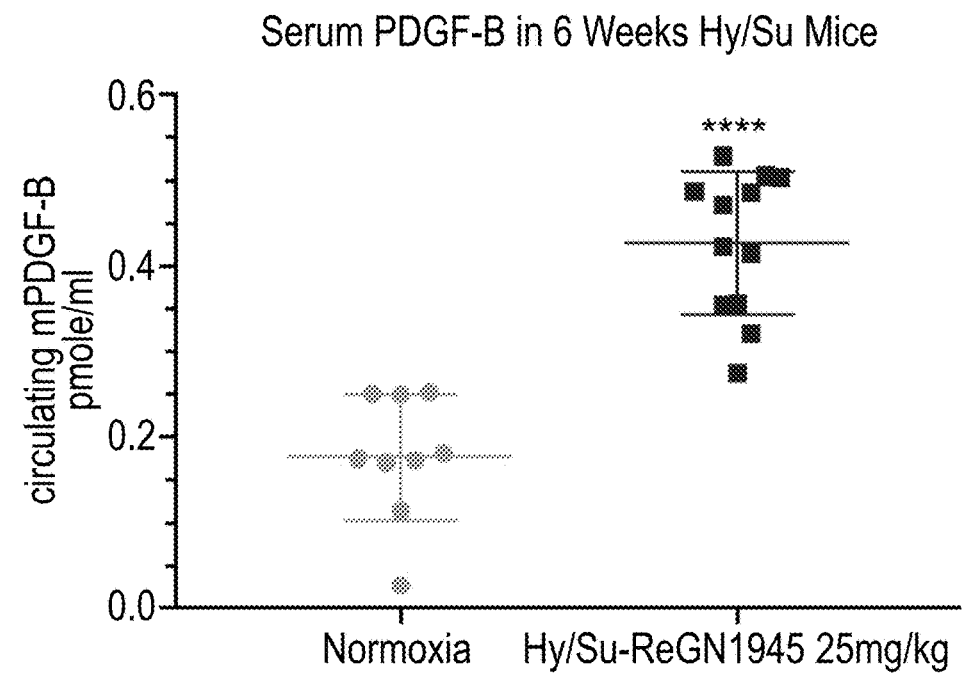
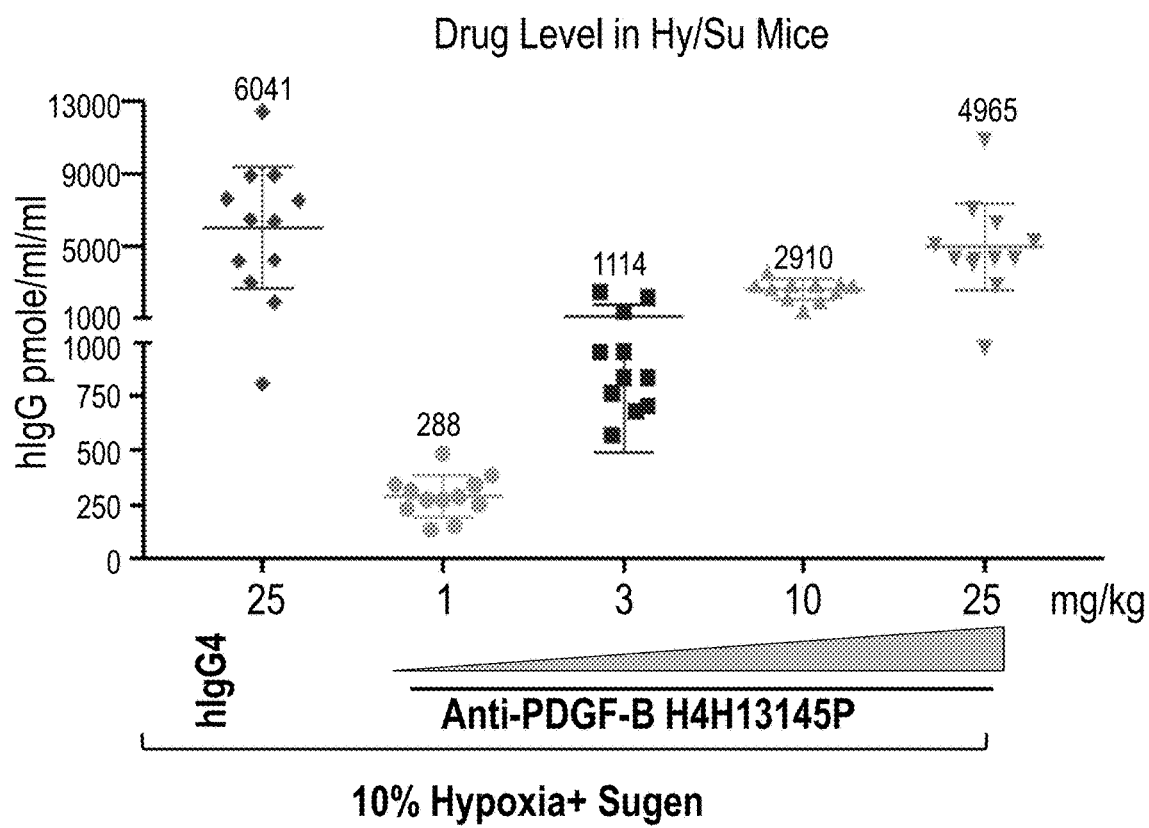

FIG. 17

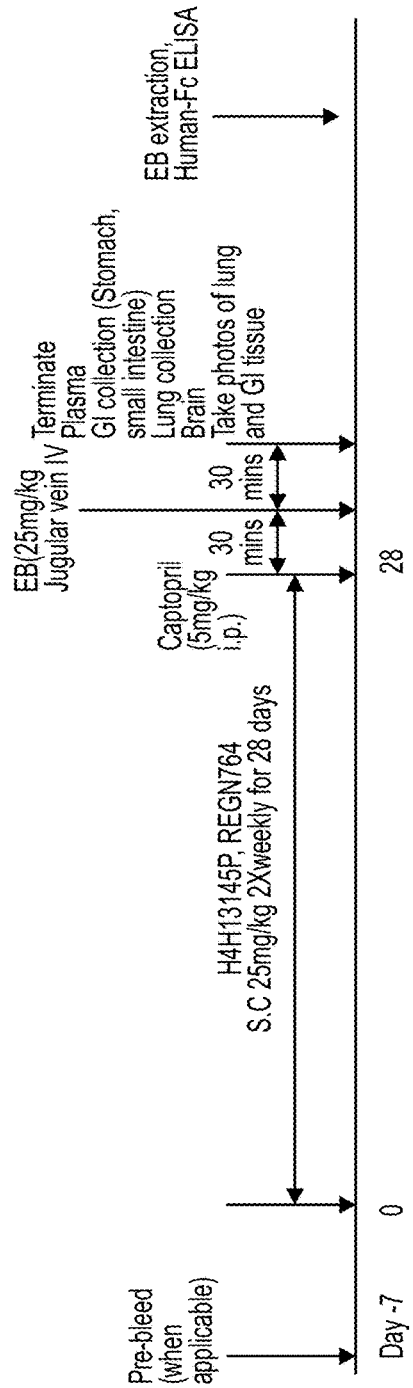

1. Saline (no Ab, no Captopril) + EB 25mg/kg 30mins
2. Saline (no Ab, Captopril 5mg/kg i.p) + EB 25mg/kg 30mins
3. Saline (Iso ctrl Ab REGN1945 25mg/kg 2Xweekly 28 days) + EB 25mg/kg 30mins
4. Saline (Anti-PDGFRb REGN764 25mg/kg 2Xweekly 28 days,) + EB 25mg/kg 30mins
5. Saline (Anti-PDGF-B REGN13335 25mg/kg 2Xweekly 28 days,) + EB 25mg/kg 30mins
6. Saline (Iso ctrl Ab REGN1945 25mg/kg 2Xweekly 28 days, Captopril 5mg/kg i.p) + EB 25mg/kg 30mins
7. Saline (Anti-PDGFRb REGN764 25mg/kg 2Xweekly 28 days, Captopril 5mg/kg i.p) + EB 25mg/kg 30mins
8. Saline (Anti-PDGF-B REGN13335 25mg/kg 2Xweekly 28 days, Captopril 5mg/kg i.p) + EB 25mg/kg 30mins

Primary Endpoints:
- Stomach weight,
- Small Intestine weight
- Lung weight
- Brain weight
- Stomach EB dye content
- Small intestine EB dye content
- Lung EB dye content
- Brain EB dye content

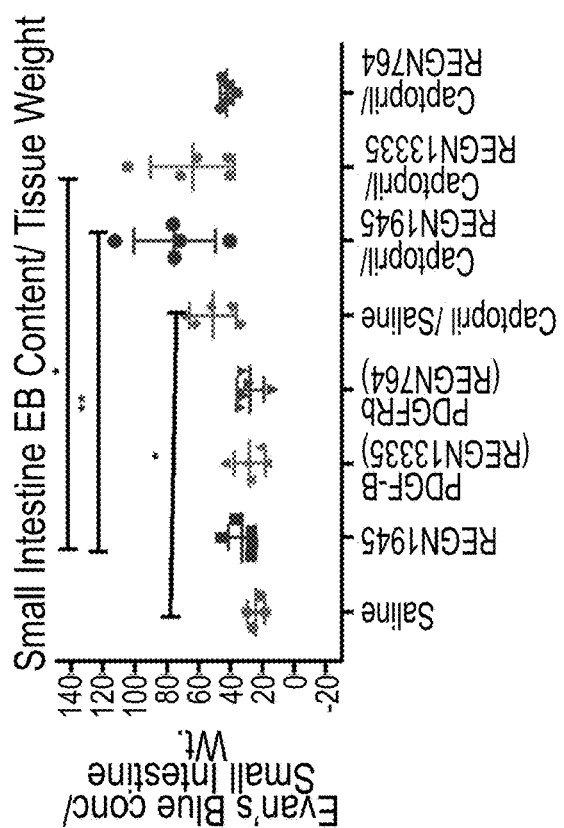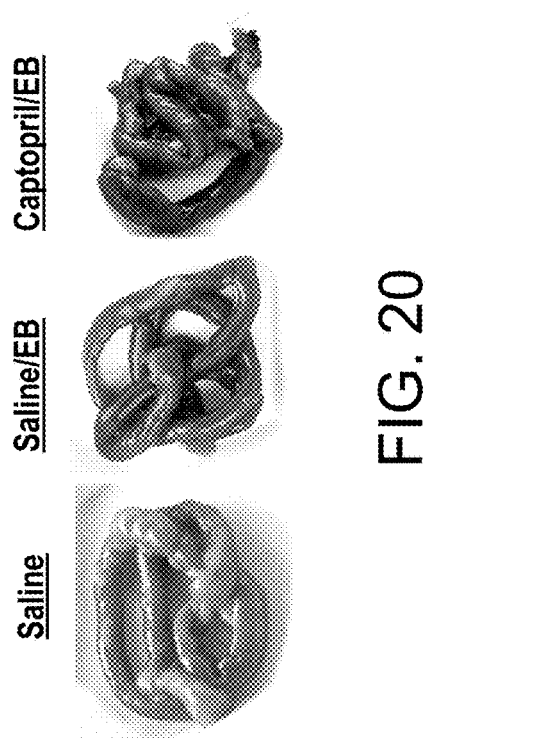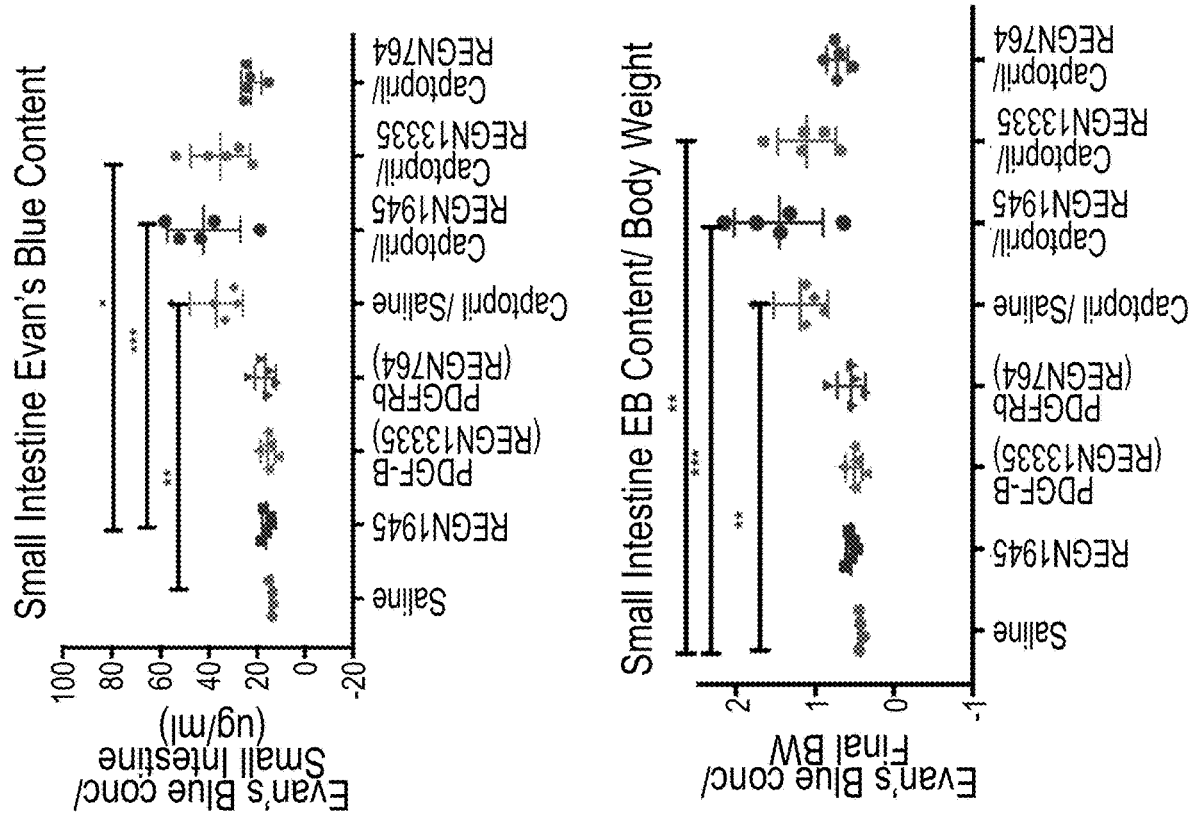
FIG. 20

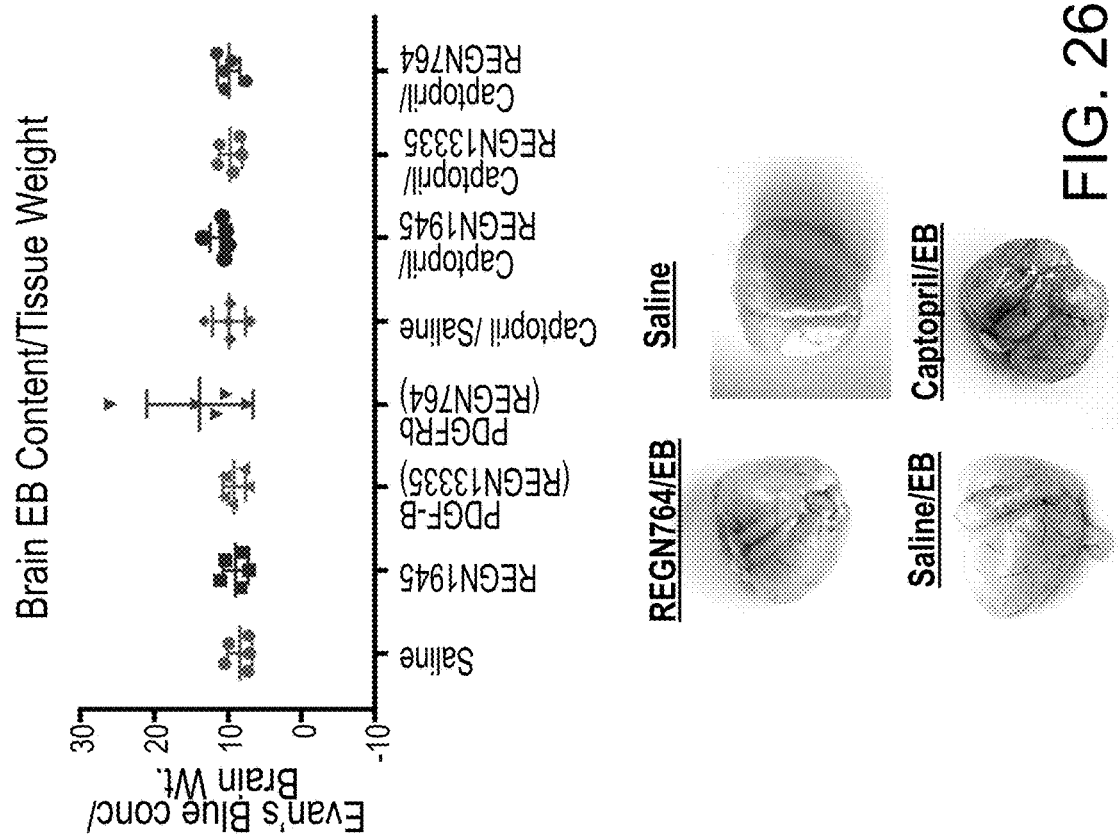
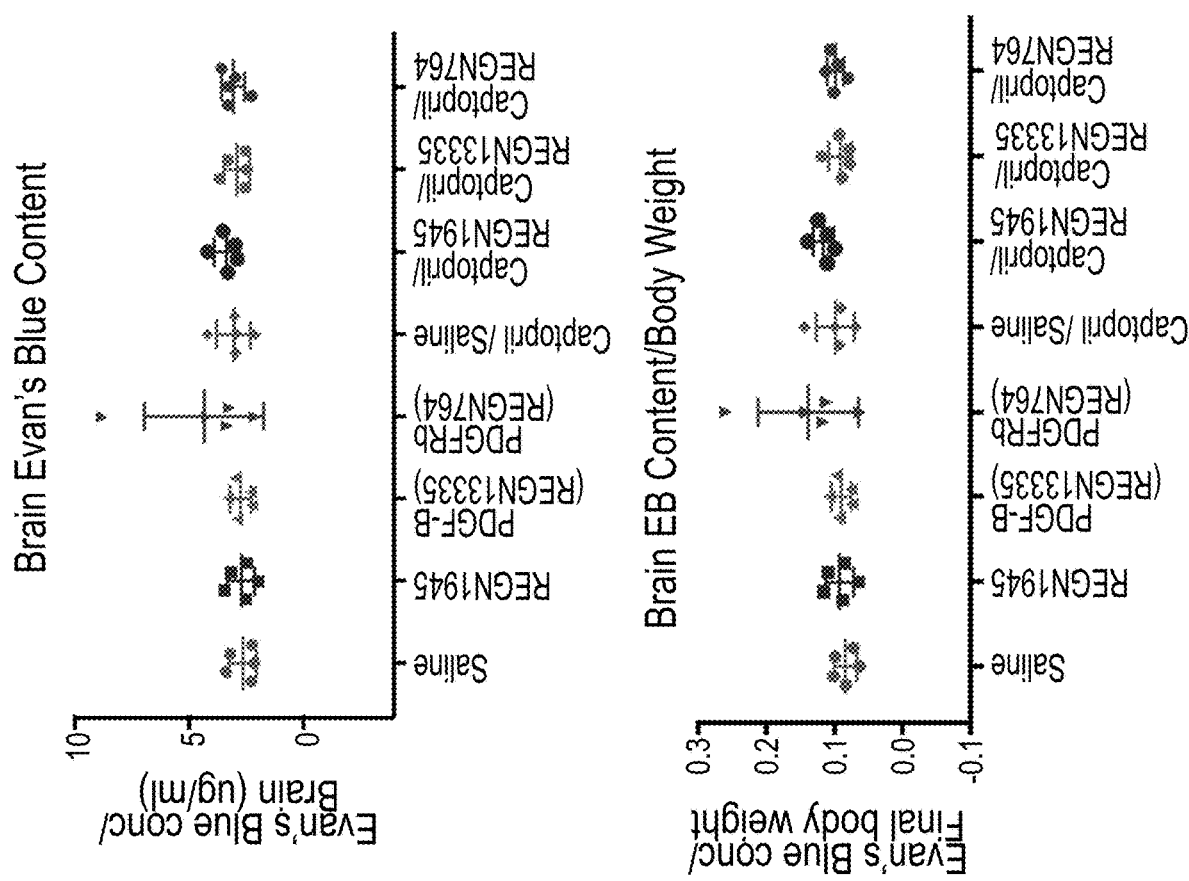
FIG. 26

ANTI-PDGF-B ANTIBODIES AND PHARMACEUTICAL COMPOSITION THEREOF

RELATED APPLICATIONS

The instant application claims priority to U.S. Provisional Application No. 63/141,030, filed on Jan. 25, 2021, the entire contents of which are expressly incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 20, 2022, is named 118003-00720_SL.txt and is 33,624 bytes in size.

FIELD

The present invention is related to human antibodies and antigen-binding fragments thereof that specifically bind to Platelet-Derived Growth Factor Subunit B (PDGF-B), and to therapeutic and diagnostic methods of using such antibodies and fragments.

BACKGROUND

Platelet-derived growth factors (PDGFs) are potent mitogens that exist as five different dimeric configurations composed of four different isoform subunits: A, B, C and D. The five dimeric forms of the PDGFs are AA, BB, AB, CC and DD, which are formed by disulfide linkage of the corresponding individual PDGF monomers. PDGF ligands exert their biological effects through their interactions with PDGF receptors (PDGFRs). PDGFRs are single-pass, transmembrane, tyrosine kinase receptors composed of heterodimeric or homodimeric associations of an alpha (α) receptor chain (PDGFR-alpha) and/or a beta (β) receptor chain (PDGF-B). Thus, active PDGFRs may consist of αα, ββ or αβ receptor chain pairings. PDGFRs share a common domain structure, including five extracellular immunoglobulin (Ig) loops, a transmembrane domain, and a split intracellular tyrosine kinase (TK) domain. The interaction between dimeric PDGF ligands and PDGFRs leads to receptor chain dimerization, receptor autophosphorylation and intracellular signal transduction. It has been demonstrated in vitro that ββ receptors are activated by PDGF-BB and -DD, while αβ receptors are activated by PDGF-BB, -CC, -DD and -AB, and αα receptors are activated by PDGF-AA, -BB, -CC and -AB (see Andrae et al. (2008) Genes Dev 22(10): 1276-1312).

PDGF signaling has been implicated in various human diseases including pulmonary arterial hypertension (PAH). Pulmonary arterial hypertension (PAH) is a progressive disorder characterized by a sustained increase in pulmonary artery pressure that damages both the large and small pulmonary arteries. PAH is defined hemodynamically as a systolic pulmonary artery pressure greater than 30 mm Hg or evaluation of mean pulmonary artery pressure greater than 25 mm Hg with a pulmonary capillary or left atrial pressure equal to or less than 15 mm Hg. See, e.g., Zaiman et al., *Am. J. Respir. Cell Mol. Biol.* 33:425-31 (2005). The persistent vasoconstriction in PAH leads to structural remodeling during which pulmonary vascular smooth muscle cells and endothelial cells undergo a phenotypic switch from a contractile normal phenotype to a synthetic phenotype leading to cell growth and matrix deposition. As the walls of the smallest blood vessels thicken, they are less able to transfer oxygen and carbon dioxide normally between the blood and the lungs and, in time, pulmonary hypertension leads to thickening of the pulmonary arteries and narrowing of the passageways through which blood flows. Eventually, the proliferation of vascular smooth muscle and endothelial cells leads to remodeling of the vessels with obliteration of the lumen of the pulmonary vasculature. Histological examination of tissue samples from patients with pulmonary hypertension shows intimal thickening, as well as smooth muscle cell hypertrophy, especially for those vessels <100 μm diameter. This causes a progressive rise in pulmonary pressures as blood is pumped through decreased lumen area. As a consequence, the right side of the heart works harder to compensate and the increased effort causes the right ventricle to become enlarged and thickened. The enlarged right ventricle places a person at risk for pulmonary embolism because blood tends to pool in the ventricle and in the legs. If clots form in the pooled blood, they may eventually travel and lodge in the lungs. Eventually, the additional workload placed on the right ventricle causes the heart to fail and leads to premature death in these patients.

Standard therapies for treatment of subjects having PAH are primarily hemodynamic, influencing vessel tone and include, e.g., prostacyclin analogs, endothelin receptor antagonists, phosphodiesterase inhibitors and soluble guanylate cyclases activators/stimulators, which provide symptomatic relief and improve prognosis. However, these therapies fall short and do not re-establish the structural and functional integrity of the lung vasculature to provide a patient having PAH with handicap-free long-term survival.

Despite all the advances in the therapy of PAH there is as yet no prospect of cure of this deadly disease and the majority of patients continue to progress to right ventricular failure. Thus, there is a need in the art for new, highly specific and potent inhibitors of PDGF signaling.

SUMMARY

The disclosure provides fully human monoclonal antibodies (mAbs) and antigen-binding fragments thereof that bind specifically to Platelet-Derived Growth Factor Subunit B (PDGF-B). Such antibodies may be useful for treating a subject having pulmonary arterial hypertension (PAH).

The circulating and lung expression of PDGF-B, the potent mitogens for pulmonary smooth muscle cells and fibroblast, are increased in both patients displaying idiopathic PAH and the hypoxia/sugen PAH mouse model. The interactions of PDGF-B with PDGFRββ, PDGFRαβ, and PDGFRαα have been implicated in promoting pathological vascularization and pulmonary vascular remodeling. Accordingly, targeting PDGF-B may provide enhanced efficacy beyond PDGFRβ by targeting signaling through PDGFRαα, PDGFRαβ and PDGFRββ that coordinate to promote abnormal vessel remodeling.

Accordingly, in one aspect, the present disclosure provides an isolated human monoclonal antibody or antigen-binding fragment thereof that binds specifically to human Platelet-Derived Growth Factor Subunit B (PDGF-B).

In some embodiments, the antibody or antigen-binding fragment exhibits one or more properties selected from the group consisting of: (a) binds to human PDGF-subunit B homodimer (PDGF-BB) at 37° C. with a binding dissociation equilibrium constant ($K_D$) of less than about 1.84 pM as measured by surface plasmon resonance; (b) binds to human PDGF-BB at 37° C. with a $K_D$ of less than about 1.36 pM as measured by surface plasmon resonance; (c) binds to human PDGF-BB at 37° C. with a t½ of greater than or equal to about 1155 minutes as measured by surface plasmon resonance; (d) binds to human PDGF-BB at 25° C. with a $K_D$ of less than about 2.79 pM as measured by surface plasmon resonance; (e) binds to human PDGF-BB at 25° C. with a t½ of greater than or equal to about 1155 minutes as measured by surface plasmon resonance; (f) inhibits PDGF-B activation against human PDGF-BB with an $IC_{50}$ of less than about 1.9 nM as measured in a competition ELISA assay at 25° C.; (g) inhibits PDGF-B activation against human PDGF-subunit A and subunit B heterodimer (PDGF-AB) with an $IC_{50}$ of less than about 8.8 nM as measured in a competition ELISA assay at 25° C.; and (h) blocks interaction between human PDGF-BB and one or more of human PDGFR-αα, PDGFRαβ and PDGFR-ββ.

In some embodiments, the antibody or antigen-binding fragment comprises three heavy chain complementarity determining regions (CDRs) (HCDR1, HCDR2 and HCDR3) contained within any one of the heavy chain variable region (HCVR) sequences selected from the group consisting of SEQ ID NOs: 2 and 22; and three light chain CDRs (LCDR1, LCDR2 and LCDR3) contained within any one of the light chain variable region (LCVR) sequences selected from the group consisting of SEQ ID NOs: 10 and 30.

In some embodiments, the isolated human antibody or antigen-binding fragment thereof comprises an HCVR comprising an amino acid sequence having at least 90% identity to the sequence of SEQ ID NO:2 or SEQ ID NO:22.

In some embodiments, the antibody or antigen-binding fragment comprises a LCVR comprising an amino acid sequence having at least 90% identity to the sequence of SEQ ID NO:10 or SEQ ID NO:30.

In some embodiments, the antibody or antigen-binding fragment comprises: (a) a HCVR comprising an amino acid sequence selected from the group consisting of SEQ ID NOs: 2 and 22; and (b) a LCVR comprising an amino acid sequence selected from the group consisting of SEQ ID NO: 10 and 30.

In some embodiments, the antibody or antigen-binding fragment comprises: (a) a HCDR1 domain comprising an amino acid sequence selected from the group consisting of SEQ ID NOs: 4 and 24; (b) a HCDR2 domain comprising an amino acid sequence selected from the group consisting of SEQ ID NOs: 6 and 26; (c) a HCDR3 domain comprising an amino acid sequence selected from the group consisting of SEQ ID NOs: 8 and 28; (d) a LCDR1 domain comprising an amino acid sequence selected from the group consisting of SEQ ID NOs: 12 and 32; (e) a LCDR2 domain comprising an amino acid sequence selected from the group consisting of SEQ ID NOs: 14 and 34; and/or (f) a LCDR3 domain comprising an amino acid sequence selected from the group consisting of SEQ ID NOs: 16 and 36.

In some embodiments, the antibody or antigen-binding fragment comprises a HCVR/LCVR amino acid sequence pair selected from the group consisting of SEQ ID NOs: 2/10 and 22/30.

In some embodiments, the antibody or antigen-binding fragment comprises (i) a light chain immunoglobulin comprising the amino acid sequence set forth in SEQ ID NO: 20, and a heavy chain immunoglobulin comprising the amino acid sequence set forth in SEQ ID NO: 18; and/or (ii) a light chain immunoglobulin comprising the amino acid sequence set forth in SEQ ID NO: 40, and a heavy chain immunoglobulin comprising the amino acid sequence set forth in SEQ ID NO: 38.

In some embodiments, the antigen-binding fragment is a Fab fragment, a F(ab')2 fragment, a Fd fragment, a Fv fragment, a single-chain Fv (scFv) molecule, or a dAb fragment.

In another aspect, the disclosure provides an isolated antibody or antigen-binding fragment thereof that binds the same epitope on human PDGF-B as the antibody, or antigen binding fragment comprising three heavy chain complementarity determining regions (CDRs) (HCDR1, HCDR2 and HCDR3) contained within any one of the heavy chain variable region (HCVR) sequences selected from the group consisting of SEQ ID NOs: 2 and 22; and three light chain CDRs (LCDR1, LCDR2 and LCDR3) contained within any one of the light chain variable region (LCVR) sequences selected from the group consisting of SEQ ID NOs: 10 and 30.

In another aspect, the disclosure provides an isolated antibody or antigen-binding fragment thereof that competes for binding to human PDGF-B as the antibody, or antigen binding fragment comprising three heavy chain complementarity determining regions (CDRs) (HCDR1, HCDR2 and HCDR3) contained within any one of the heavy chain variable region (HCVR) sequences selected from the group consisting of SEQ ID NOs: 2 and 22; and three light chain CDRs (LCDR1, LCDR2 and LCDR3) contained within any one of the light chain variable region (LCVR) sequences selected from the group consisting of SEQ ID NOs: 10 and 30.

In another aspect, the invention provides nucleic acid molecules encoding anti-PDGF antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In another aspect, the disclosure provides a method for making an antibody or antigen-binding fragment disclosed herein, the method comprising: (i) introducing one or more polynucleotides encoding a light immunoglobulin chain of said antibody or fragment and a heavy immunoglobulin chain of said antibody or fragment into a host cell; (ii) culturing the host cell in a growth medium under condition favorable to expression of the polynucleotide(s); and (iii) optionally, isolating the antibody or fragment from the host cell and/or medium in which the host cell is grown.

In another aspect, the disclosure provides an antibody or antigen-binding fragment produced by the method comprising: (i) introducing one or more polynucleotides encoding a light immunoglobulin chain of said antibody or fragment and a heavy immunoglobulin chain of said antibody or fragment into a host cell; (ii) culturing the host cell in a growth medium under condition favorable to expression of the polynucleotide(s); and (iii) optionally, isolating the antibody or fragment from the host cell and/or medium in which the host cell is grown.

In some embodiments, the antibody, or antigen binding fragment comprises three heavy chain complementarity determining regions (CDRs) (HCDR1, HCDR2 and HCDR3) contained within any one of the heavy chain variable region (HCVR) sequences selected from the group consisting of SEQ ID NOs: 2 and 22; and three light chain CDRs (LCDR1, LCDR2 and LCDR3) contained within any one of the light chain variable region (LCVR) sequences selected from the group consisting of SEQ ID NOs: 10 and 30.

In another aspect, the disclosure provides an injection device or vessel comprising an antibody or antigen-binding fragment disclosed herein.

In another aspect, the disclosure provides a pharmaceutical composition comprising an isolated human antibody or antigen-binding fragment thereof that binds to human PDGF-B as described above or disclosed herein, and a pharmaceutically acceptable carrier or diluent; and, optionally, one or more additional therapeutic agents.

In some embodiments, the one or more additional therapeutic agents comprise an iron supplement.

In another aspect, the disclosure provides a method for preventing or treating pulmonary arterial hypertension (PAH) in a patient in need thereof, comprising administering an effective amount of an antibody or an antigen-binding fragment thereof that binds to human PDGF-B as disclosed herein; or a pharmaceutical composition comprising an isolated human antibody or antigen-binding fragment thereof that binds to human PDGF-B as disclosed herein to the patient.

In some embodiments, the antibody or antigen-binding fragment thereof is administered subcutaneously, intravenously, intradermally, orally, or intramuscularly.

In some embodiments, the PAH produces a condition selected from the group consisting of thickening of the pulmonary artery in the subject; decreasing stroke volume in the subject; decreasing right ventricle cardiac output in the subject; and decreasing survival time of the subject; and administration of the antibody, or antigen-binding fragment, treats the condition or reduces the severity of one or more symptoms of the condition.

In another aspect, the disclosure provides an antibody, or antigen-binding fragment thereof that binds to human PDGF-B as disclosed herein, for use in treating a patient with PAH.

In another aspect, the disclosure provides a composition comprising one or more antibodies or antigen-binding fragments that bind to human PDGF-B as disclosed herein, for use in treating PAH.

In another aspect, the disclosure provides use of the isolated antibody, or antigen-binding fragment thereof that binds to human PDGF-B as disclosed herein, in the manufacture of a medicament for treating a patient with PAH.

In some embodiments, the antibody, or antigen binding fragment thereof, described herein is capable of neutralizing PDGF-BB, PDGF-AB and/or PDGF-AB/BB and preventing PDGF driven calcium flux in a cell. In some embodiments, the antibody, or antigen binding fragment thereof, described herein is capable of neutralizing PDGF-BB and preventing PDGF driven calcium flux in a cell. In some embodiments, the antibody, or antigen binding fragment thereof, described herein is capable of neutralizing PDGF-AB and preventing PDGF driven calcium flux in a cell. In some embodiments, the antibody, or antigen binding fragment thereof, described herein is capable of neutralizing PDGF-AB/BB and preventing PDGF driven calcium flux in a cell.

In some embodiments, the antibody, or antigen binding fragment thereof, described herein is capable of neutralizing PDGF-BB, PDGF-AB and/or PDGF-AB/BB and preventing PDGF driven cellular proliferation. In some embodiments, the antibody, or antigen binding fragment thereof, described herein is capable of neutralizing PDGF-BB and preventing PDGF driven cellular proliferation. In some embodiments, the antibody, or antigen binding fragment thereof, described herein is capable of neutralizing PDGF-AB and preventing PDGF driven cellular proliferation. In some embodiments, the antibody, or antigen binding fragment thereof, described herein is capable of neutralizing PDGF-AB/BB and preventing PDGF driven cellular proliferation.

In some embodiments, the cell is a human cell. In some embodiments, the cell is selected from the group consisting of pulmonary artery smooth muscle cell and primary human lung fibroblast.

In some embodiments, the antibody, or antigen binding fragment thereof, described herein bind to the outside edge of β-sheet region of PDGF-BB. In some embodiments, the antibody, or antigen binding fragment thereof, described herein bind to the interstrand loops of PDGF-BB. In some embodiments, the antibody, or antigen binding fragment thereof, described herein bind to the outside edge of β-sheet region and the interstrand loops of PDGF-BB. In some embodiments, the antibody, or antigen binding fragment thereof, described herein bind to one or more residues of PDGF-BB selected from the group consisting of W40, R73, K80, K81, P82, F84, K86, and R56. In some embodiments, the antibody, or antigen binding fragment thereof, described herein binds to a W40 residue of PDGF-BB. In some embodiments, the antibody, or antigen binding fragment thereof, described herein binds to a R73 residue of PDGF-BB. In some embodiments, the antibody, or antigen binding fragment thereof, described herein binds to a K80 residue of PDGF-BB. In some embodiments, the antibody, or antigen binding fragment thereof, described herein binds to a K81 residue of PDGF-BB. In some embodiments, the antibody, or antigen binding fragment thereof, described herein binds to a P82 residue of PDGF-BB. In some embodiments, the antibody, or antigen binding fragment thereof, described herein binds to a F84 residue of PDGF-BB. In some embodiments, the antibody, or antigen binding fragment thereof, described herein binds to a K86 residue of PDGF-BB. In some embodiments, the antibody, or antigen binding fragment thereof, described herein binds to a R56 residue of PDGF-BB.

In some embodiments, the antibody, or antigen binding fragment thereof, described herein is internalized into a cell in a ligand dependent manner through a PDGF receptor. In some embodiments, the cell is a human cell. In some embodiments, the cell is selected from the group consisting of pulmonary artery smooth muscle cell and primary human lung fibroblast.

In some embodiments, the antibody, or antigen binding fragment thereof, described herein is capable of reducing right ventricular systolic pressure in a subject in need thereof. In some embodiments, the antibody, or antigen binding fragment thereof, described herein is capable of reducing right ventricular hypertrophy in a subject in need thereof. In some embodiments, the antibody, or antigen binding fragment thereof, described herein is capable of reducing right ventricular systolic pressure and right ventricular hypertrophy in a subject in need thereof.

Other embodiments will become apparent from a review of the ensuing detailed description.

BRIEF DESCRIPTION OF THE DRAWINGS

FIGS. 4A-4B are graphs depicting that 5 strong anti-PDGF-B antibodies were identified which blocked >70%; 3 anti-PDGF-B antibodies blocked both PDGF-BB and PDGF-AB with $IC_{50}$ value ranges for PDGF-BB of 0.23-1.8 nM; 2 anti-PDGF-B antibodies blocked only PDGF-BB with $IC_{50}$ value ranges of 0.55-0.64 nM; 6 moderate anti-PDGF-B antibodies blocked >45%; 2 anti-PDGF-B antibodies blocked both PDGF-BB and PDGF-AB with $IC_{50}$ value ranges for PDGF-BB of 2.8-13 nM; 4 anti-PDGF-B antibodies blocked only PDGF-BB with $IC_{50}$ value ranges of 0.64-2.8 nM; and 6 anti-PDGF-B antibodies were non-blockers. FIG. 4C is a table that summarizes the characterization of the anti-PDGF-B antibodies in Blocking ELISA with soluble PDGF-BB and PDGF-AB and plate-capture PDGFR-beta.

FIG. 5D is a graph depicting that 10 out of 17 anti-hPDGF-B antibodies inhibited 600 pM of mouse PDGF-BB with $IC_{50}$ values of 450 pM-6.4 nM with maximum inhibitions of 39-98%.

FIG. 8 is a Table depicting that commercial Monkey PDGF-BB showed specific binding to the anti-PDGF-B mAbs H4H13132P and H4H13145P.

FIG. 13A is a panel of graphs depicting that anti-PDGF-B at low does of 1 mg/kg s.c provided efficacy in clinically relevant endpoint (right ventricular pressure) of PAH.

FIG. 13B is a panel of graphs depicting the circulating PDGF-B levels and anti-PDGF-B concentration in Hy/Su mice at Day 42 post administration of the anti-PDGF-B antibody.

FIG. 17 is a schematic depicting the study design of evaluating the impact of chronic treatment of healthy C57BL adult mice with high doses of anti-PDGF-B antibodies in gastrointestinal (GI), lung, or brain vascular hyperpermeability.

FIG. 20 is a panel of graphs and images depicting that there was no significant change in vessel permeability in the small intestine by treatment of anti-PDGF-B and anti-PDGFRβ antibodies in mice.

FIG. 26 is a panel of graphs and images depicting that there was no significant change in vessel permeability in the brain by treatment of anti-PDGF-B and anti-PDGFRβ antibodies in healthy and Captopril treated mice.

DETAILED DESCRIPTION

Figure 1:
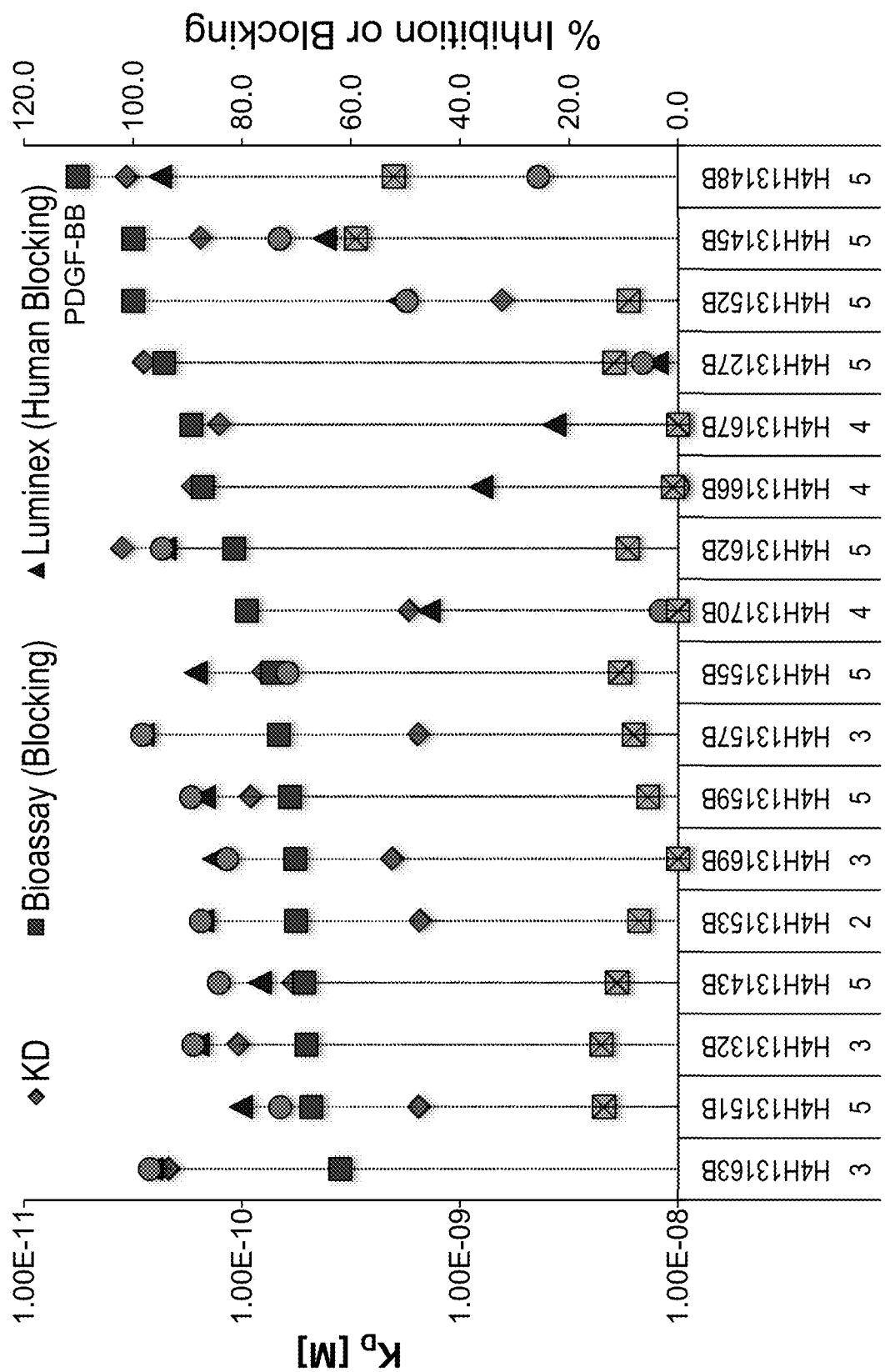
FIG. 1 is a graph depicting the screening results of the monoclonal anti-PDGF antibodies from the VI-3 mice.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The terms "PDGF-B," "PDGFB," and "Platelet-Derived Growth Factor B" refer, interchangeably, to the human PDGF-B protein having the amino acid sequence of SEQ ID NO: 41 (see also UniProt accession No. P01127). All references to proteins, polypeptides and protein fragments herein are intended to refer to the human version of the respective protein, polypeptide or protein fragment unless explicitly specified as being from a non-human species (e.g., "mouse PDGF-B," "monkey PDGF-B," etc.). The circulating and lung expression of PDGF-B, the potent mitogens for pulmonary smooth muscle cells and fibroblast, are increased in both patients displaying idiopathic PAH and the hypoxia/sugen PAH mouse model. The interactions of PDGF-B with PDGFRββ, PDGFRαβ, and PDGFRαα have been implicated in promoting pathological vascularization and pulmonary vascular remodeling. Mechanistically, targeting PDGF-B may provide enhanced efficacy beyond PDGFRβ by targeting signaling through PDGFRαα, PDGFRαβ and PDGFRββ that coordinate to promote abnormal vessel remodeling.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g., IgM) or antigen-binding fragments thereof. Each heavy chain is comprised of a heavy chain variable region ("HCVR" or "VH") and a heavy chain constant region (comprised of domains CH1, CH2 and CH3). Each light chain is comprised of a light chain variable region ("LCVR" or "VL") and a light chain constant region (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In certain embodiments, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (FASEB J. 1995, 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human PDGF-B monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments that comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes fully human anti-PDGF-B monoclonal antibodies comprising variants of any of the HCVR, LCVR, and/or CDR amino acid sequences disclosed herein having one or more conservative substitutions. For example, the present disclosure includes anti-PDGF-B antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "pulmonary hypertension" ("PH") is a term used to describe high blood pressure in the lungs from any cause. The terms "hypertension" or "high blood pressure," on the other hand, refer to high blood pressure in the arteries throughout the body.

The term "pulmonary arterial hypertension" ("PAH") refers to a progressive lung disorder which is characterized by sustained elevation of pulmonary artery pressure. Those patients with PAH typically have pulmonary artery pressure that is equal to or greater than 25 mm Hg with a pulmonary capillary or left atrial pressure equal to or less than 15 mm Hg. These pressures are typically measured in a subject at rest using right-heart catheterization. PAH, when untreated, leads to death (on average) within 2.8 years after being diagnosed.

The World Health Organization (WHO) has provided a clinical classification of PAH of five groups (Simonneau, et al. *J Am Coll Cardiol.* 2013; 62(25_S), the entire contents of which are incorporated herein by reference):

1. Pulmonary arterial hypertension (PAH)
   1.1. Idiopathic
   1.2. Heritable
      1.2.1. BMPR2
      1.2.2. ALK1, ENG, SMAD9, CAV1, KCNK3
      1.2.3. Unknown
   1.3. Drug- and toxin-induced
   1.4. Associated with:
      1.4.1. Connective tissue diseases
      1.4.2. HIV infection
      1.4.3. Portal Hypertension
      1.4.4. Congenital heart diseases
      1.4.5. Schistosomiasis
1'. Pulmonary veno-occlusive disease (PVOD) and/or pulmonary capillary hemangiomatosis (PCH)
1". Persistent pulmonary hypertension of the newborn (PPHN)
2. Pulmonary hypertension due to left heart disease
   2.1. Left ventricular systolic dysfunction
   2.2. Left ventricular diastolic dysfunction
   2.3. Valvular disease
   2.4. Congenital/acquired left heart inflow/outflow tract obstruction and congenital cardiomyopathies
3. Pulmonary hypertension due to lung disease and/or hypoxia
   3.1. Chronic obstructive pulmonary disease
   3.2. Interstitial lung disease
   3.3. Other pulmonary diseases with mixed restrictive and obstructive pattern
   3.4. Sleep-disordered breathing
   3.5. Alveolar hypoventilation disorders
   3.6. Chronic exposure to high altitude
   3.7. Developmental abnormalities
4. Chronic thromboembolic pulmonary hypertension (CTEPH)
5. Pulmonary hypertension with unclear multifactorial mechanisms
   5.1. Hematologic disorders: chronic hemolytic anemia, myeloproliferative disorders, splenectomy
   5.2. Systemic disorders: sarcoidosis, pulmonary histiocytosis, lymphangioleimyomatosis
   5.3. Metabolic disorders: glycogen storage disease, Gaucher disease, thyroid disorders
   5.4. Others: tumoral obstruction, fibrosing mediastinitis, chronic renal failure on dialysis, segmental PH.

In one embodiment, a subject that would benefit from the methods of the present disclosure is a subject having Group I (WHO) PAH.

PAH at baseline (e.g., when diagnosed) can be mild, moderate or severe, as measured, for example, by the WHO functional class, which is a measure of disease severity in patients with PAH. The WHO functional classification is an adaptation of the New York Heart Association (NYHA) system and is routinely used to qualitatively assess activity tolerance, for example, in monitoring disease progression and response to treatment (Rubin (2004) *Chest* 126:7-10). There are four functional classes recognized in the WHO system:

Class I: pulmonary hypertension without resulting limitation of physical activity; ordinary physical activity does not cause undue dyspnea or fatigue, chest pain or near syncope;

Class II: pulmonary hypertension resulting in slight limitation of physical activity; patient comfortable at rest; ordinary physical activity causes undue dyspnea or fatigue, chest pain or near syncope;

Class III: pulmonary hypertension resulting in marked limitation of physical activity; patient comfortable at rest; less than ordinary activity causes undue dyspnea or fatigue, chest pain or near syncope; and Class IV: pulmonary hypertension resulting in inability to carry out any physical activity without symptoms; patient manifests signs of right-heart failure; dyspnea and/or fatigue may be present even at rest; discomfort is increased by any physical activity.

In one embodiment, a subject that would benefit from the methods of the present disclosure is a subject having, at baseline, PAH e.g., Group I (WHO) PAH) of WHO Class I. In another embodiment, a subject that would benefit from the methods of the present disclosure is a subject having, at baseline, PAH (e.g., Group I (WHO) PAH) of WHO Class II. In another embodiment, a subject that would benefit from the methods of the present disclosure is a subject having, at baseline, PAH e.g., Group I (WHO) PAH) of WHO Class III.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose).

In one embodiment, the subject is a human, such as a human being treated or assessed for PAH e.g., Group I (WHO) PAH; a human at risk for PAH e.g., Group I (WHO) PAH; a human having PAH e.g., Group I (WHO) PAH; and/or human being treated for PAH e.g., Group I (WHO) PA), as described herein.

As used herein, the terms "treating" or "treatment" refer to a beneficial or desired result including, but not limited to, alleviation or amelioration of one or more symptoms associated with PAH e.g., Group I (WHO) PAH). "Treatment" can also mean slowing the course of the disease or reducing the development of a symptom of disease, reducing the severity of later-developing disease, or prolonging survival as compared to expected survival in the absence of treatment. For example, the reduction in the development of a symptom associated with such a disease, disorder or condition (e.g., by at least about 10% on a clinically accepted scale for that disease or disorder), or the exhibition of delayed symptoms delayed (e.g., by days, weeks, months or years) is considered effective treatment.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies that bind specifically to PDGF-B have been identified by surface plasmon resonance, e.g., BIACORE™. Moreover, multi-specific antibodies that bind to one domain in PDGF-B and one or more additional antigens or a bi-specific that binds to two different regions of PDGF-B are nonetheless considered antibodies that "specifically bind", as used herein.

The term "high affinity" antibody refers to those mAbs having a binding affinity to PDGF-B, expressed as $K_D$, of at least $10^{-7}$ M; preferably $10^{-8}$M; more preferably $10^{-9}$M, even more preferably $10^{-10}$ M, even more preferably $10^{-11}$ M, as measured by surface plasmon resonance, e.g., BIACORE™ or solution-affinity ELISA.

By the term "slow off rate", "Koff" or "kd" is meant to describe an antibody that dissociates from PDGF-B with a rate constant of $1\times10^{-3}$ s$^{-1}$ or less, preferably $1\times10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to PDGF-B.

In specific embodiments, antibody or antibody fragments of the disclosure may be conjugated to a therapeutic moiety ("immunoconjugate"), such as an antibiotic, a second anti-PDGF-B antibody, or an antibody to a cytokine such as IL-1, IL-6, or TGF-β, or any other therapeutic moiety useful for treating pulmonary arterial hypertension.

An "isolated antibody", as used herein, is intended to refer to an antibody that is substantially free of other antibodies (Abs) having different antigenic specificities (e.g., an isolated antibody that specifically binds PDGF-B, or a fragment thereof, is substantially free of Abs that specifically bind antigens other than PDGF-B).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25: 3389-3402, each of which is herein incorporated by reference.

In specific embodiments, the antibody or antibody fragment for use in the method of the disclosure may be mono-specific, bi-specific, or multi-specific. Multi-specific antibodies may be specific for different epitopes of one target polypeptide or may contain antigen-binding domains specific for epitopes of more than one target polypeptide.

By the phrase "Therapeutically effective amount," as used herein, is intended to include the amount of an anti-PDGF-B antibody, or antigen-binding fragment thereof, that, when administered to a subject having PAH e.g., Group I (WHO) PAH, is sufficient to effect treatment of the disease (e.g., by diminishing, ameliorating or maintaining the existing disease or one or more symptoms of disease) or manage the disease. The "therapeutically effective amount" may vary depending on the anti-PDGF-B antibody, or antigen-binding fragment thereof, how the anti-PDGF-B antibody, or antigen-binding fragment thereof, is administered, the disease and its severity and the history, age, weight, family history, genetic makeup, stage of PAH, the types of preceding or concomitant treatments, if any, and other individual characteristics of the patient to be treated.

A "therapeutically effective amount" is also intended to include the amount of an anti-PDGF-B antibody, or antigen-binding fragment thereof, that, when administered to a subject is sufficient to ameliorate the disease or one or more symptoms of the disease. Ameliorating the disease includes slowing the course of the disease or reducing the severity of later-developing disease.

A "therapeutically-effective amount" also includes an amount of an anti-PDGF-B antibody, or antigen-binding fragment thereof, that produces some desired local or systemic effect at a reasonable benefit/risk ratio applicable to any treatment. Anti-PDGF-B antibodies, or antigen-binding fragments thereof, employed in the methods of the present disclosure may be administered in a sufficient amount to produce a reasonable benefit/risk ratio applicable to such treatment.

General Description

Platelet-derived growth factors (PDGFs) are potent mitogens that exist as five different dimeric configurations composed of four different isoform subunits: A, B, C and D. The five dimeric forms of the PDGFs are AA, BB, AB, CC and DD, which are formed by disulfide linkage of the corresponding individual PDGF monomers. PDGF ligands exert their biological effects through their interactions with PDGF receptors (PDGFRs). PDGFRs are single-pass, transmembrane, tyrosine kinase receptors composed of heterodimeric or homodimeric associations of an alpha (α) receptor chain (PDGFR-alpha) and/or a beta (β) receptor chain (PDGF-B). Thus, active PDGFRs may consist of αα, ββ or β receptor chain pairings. PDGFRs share a common domain structure, including five extracellular immunoglobulin (Ig) loops, a transmembrane domain, and a split intracellular tyrosine kinase (TK) domain. The interaction between dimeric PDGF ligands and PDGFRs leads to receptor chain dimerization, receptor autophosphorylation and intracellular signal transduction. It has been demonstrated in vitro that ββ receptors are activated by PDGF-BB and -DD, while αβ receptors are activated by PDGF-BB, -CC, -DD and -AB, and αα receptors are activated by PDGF-AA, -BB, -CC and -AB (see Andrae et al. (2008) Genes Dev 22(10): 1276-1312).

The antibodies described herein demonstrate specific binding to PDGF-B and in some embodiments, may be useful for treating patients suffering from pulmonary arterial hypertension. They may be used alone or as adjunct therapy with other therapeutic moieties or modalities known in the art for treating pulmonary arterial hypertension, such as, but not limited to, iron supplementation through iron supplements, dietary changes to promote serum iron and/or intravenous delivery of iron, blood transfusion, and iron promoting medications. They may be used in conjunction with additional antibodies specific for antigens other than PDGF-B or may combined with other types of treatments.

In some embodiments, the antibodies described herein may be useful in preventing, treating or managing pulmonary arterial hypertension.

In certain embodiments, the antibodies of the disclosure are obtained from mice immunized with a primary immunogen, such as a native, full length human PDGF-B (SEQ ID NO: 41) or PDGF-B fragments, followed by immunization with a secondary immunogen, or with an immunogenically active fragment of PDGF-B.

The immunogen may be an immunogenic fragment of PDGF-B or DNA encoding the fragment thereof. The immunogen may be PDGF-B coupled to a histidine tag and/or to a fragment of Fc region of an antibody.

The amino acid sequence of full length human PDGF-B is shown as SEQ ID NO: 41.

In certain embodiments, antibodies that bind specifically to PDGF-B may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of PDGF-B-specific antibodies. In certain embodiments, any one or more of the above-noted regions of PDGF-B, or fragments thereof may be used for preparing monospecific, bispecific, or multi-specific antibodies.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to PDGF-B. An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single-domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H$1; (ii) $V_H$-$C_H$2; (iii) $V_H$ (iv) $V_H$-$C_H$1-$C_H$2; (v) $V_H$-$C_H$1-$C_H$2-$C_H$3; (vi) $V_H$-$C_H$2-$C_H$3; (vii) $V_H$-CL; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$ In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

The present disclosure includes anti-PDGF-B antibodies and antigen-binding fragments having immunoglobulin chains that include the amino acid sequences set forth herein as well as variants having cellular and/or in vitro post-translational modifications. For example, the present disclosure includes antibodies and antigen-binding fragments thereof that specifically bind to PDGF-B comprising heavy and/or light chain amino acid sequences set forth herein (e.g., CDR-H1, CDR-H2, CDR-H3, CDR-L1, CDR-L2 and/or CDR-L3) as well as antibodies and fragments wherein one or more amino acid residues is glycosylated, one or more Asn residues is deamidated, one or more residues (e.g., Met, Trp and/or His) is oxidized, the N-terminal Gln is pyroglutamate (pyroE) and/or the C-terminal Lysine is missing.

The present disclosure includes recombinant methods for making anti-PDGF-B antibodies or antigen-binding fragments thereof, or an immunoglobulin chain thereof, comprising (i) introducing one or more polynucleotides encoding a light and/or a heavy immunoglobulin chain of said antibody or antigen-binding fragment (e.g., a heavy chain or $V_H$ thereof or immunoglobulin comprising the HCDR1, HCDR2 and HCDR3 thereof and/or a light chain or $V_L$ thereof or immunoglobulin comprising the LCDR1, LCDR2 and LCDR3 thereof), for example, wherein the polynucleotide is in a vector and/or is operably linked to a promoter; (ii) culturing the host cell (e.g., Chinese hamster ovary (CHO) cell or *Pichia* cell or *Pichia pastoris* cell) under condition favorable to expression of the polynucleotide(s) and, (iii) optionally, isolating the antibody or fragment or chain from the host cell and/or medium in which the host cell is grown. When making an antibody or antigen-binding fragment comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antibody or antigen-binding fragment molecule. The methods include those wherein only a heavy immunoglobulin chain or only a light immunoglobulin chain (e.g., any of those discussed herein including mature fragments and/or variable domains thereof) is expressed. Such chains are useful, for example, as intermediates in the expression of an antibody or antigen-binding fragment that includes such a chain. The present disclosure includes the products of such expression methods (e.g., antibodies, antigen-binding fragments, $V_H$s, or $V_L$s).

Preparation of Human Antibodies

Methods for generating human antibodies in transgenic mice are known in the art. Any such known methods can be used in the context of the present disclosure to make human antibodies that specifically bind to PDGF-B.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to PDGF-B are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high-affinity chimeric antibodies are isolated having a human variable region and a mouse constant region. The antibodies are characterized and selected for desirable characteristics, including affinity, selectivity, epitope, etc. The mouse constant regions are replaced with a desired human constant region to generate the fully human antibody of the disclosure, for example wild type or modified IgG1 or IgG4. While the constant region selected may vary according to specific use, high affinity antigen-binding and target specificity characteristics reside in the variable region.

In general, the antibodies of the instant disclosure possess very high affinities, typically possessing $K_D$ of from about $10^{-12}$ through about $10^{-7}$ M, when measured by binding to antigen either immobilized on solid phase or in solution phase. The mouse constant regions are replaced with desired human constant regions to generate the fully human antibodies of the disclosure. While the constant region selected may vary according to specific use, high affinity antigen-binding and target specificity characteristics reside in the variable region.

Bioequivalents

The anti-PDGF-B antibodies and antibody fragments of the present disclosure encompass proteins having amino acid sequences that vary from those of the described antibodies, but that retain the ability to bind PDGF-B. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment of the disclosure.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-PDGF-B Antibodies Comprising Fc Variants

According to certain embodiments of the present disclosure, anti-PDGF-B antibodies are provided comprising an Fc domain comprising one or more mutations which enhance or diminish antibody binding to the FcRn receptor, e.g., at acidic pH as compared to neutral pH. For example, the present disclosure includes anti-PDGF-B antibodies comprising a mutation in the $C_H2$ or a CH3 region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal.

All possible combinations of the foregoing Fc domain mutations, and other mutations within the antibody variable domains disclosed herein, are contemplated within the scope of the present disclosure.

The present disclosure also includes anti-PDGF-B antibodies comprising a chimeric heavy chain constant ($C_H$) region, wherein the chimeric $C_H$ region comprises segments derived from the $C_H$ regions of more than one immunoglobulin isotype. For example, the antibodies of the disclosure may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the disclosure comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

Biological Characteristics of the Antibodies

In general, the antibodies of the present disclosure may function by binding to PDGF-B. In some embodiments, the antibodies of the present disclosure may bind to another antigen (cross-reactive antibodies).

In certain embodiments, the antibodies of the present disclosure may be bi-specific antibodies. The bi-specific antibodies of the disclosure may bind one epitope in one domain and may also bind one epitope in a second domain of PDGF-B. In certain embodiments, the bi-specific antibodies of the disclosure may bind two different epitopes in the same domain.

In one embodiment, the disclosure provides a fully human monoclonal antibody or antigen-binding fragment thereof that binds to PDGF-B, wherein the antibody or fragment thereof exhibits one or more of the following characteristics: (i) comprises a HCVR having an amino acid sequence selected from the group consisting of SEQ ID NO: 2 and 22, or a substantially similar sequence thereof having at least 90%, at least 95%, at least 98% or at least 99% sequence identity; (ii) comprises a LCVR having an amino acid sequence selected from the group consisting of SEQ ID NO: 10 and 30, or a substantially similar sequence thereof having at least 90%, at least 95%, at least 98% or at least 99% sequence identity; (iii) comprises a HCDR3 domain having an amino acid sequence selected from the group consisting of SEQ ID NO: 8 and 28, or a substantially similar sequence thereof having at least 90%, at least 95%, at least 98% or at least 99% sequence identity; and a LCDR3 domain having an amino acid sequence selected from the group consisting of SEQ ID NO: 16 and 36, or a substantially similar sequence thereof having at least 90%, at least 95%, at least 98% or at least 99% sequence identity; (iv) comprises a HCDR1 domain having an amino acid sequence selected from the group consisting of SEQ ID NO: 4 and 24, or a substantially similar sequence thereof having at least 90%, at least 95%, at least 98% or at least 99% sequence identity; a HCDR2 domain having an amino acid sequence selected from the group consisting of SEQ ID NO: 6 and 26, or a substantially similar sequence thereof having at least 90%, at least 95%, at least 98% or at least 99% sequence identity; a LCDR1 domain having an amino acid sequence selected from the group consisting of SEQ ID NO: 12 and 32, or a substantially similar sequence thereof having at least 90%, at least 95%, at least 98% or at least 99% sequence identity; and a LCDR2 domain having an amino acid sequence selected from the group consisting of SEQ ID NO: 14 and 34, or a substantially similar sequence thereof having at least 90%, at least 95%, at least 98% or at least 99% sequence identity; and (v) binds to PDGF-B with a $K_D$ equal to or less than $10^{-7}$.

Certain anti-PDGF-B antibodies of the present disclosure are able to bind to and neutralize the activity of PDGF-B, as determined by in vitro or in vivo assays. The ability of the antibodies to bind to and neutralize the activity of PDGF-B may be measured using any standard method known to those skilled in the art, including binding assays, or activity assays, as described herein.

The peptides may be modified to include addition or substitution of certain residues for tagging or for purposes of conjugation to carrier molecules, such as, KLH. For example, a cysteine may be added at either the N-terminal or C-terminal end of a peptide, or a linker sequence may be added to prepare the peptide for conjugation to, for example, KLH for immunization.

The antibodies specific for PDGF-B may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

Epitope Mapping and Related Technologies

The present disclosure includes anti-PDGF-B antibodies which interact with one or more amino acids found within one or more regions of PDGF-B. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned regions of the PDGF-B molecule (e.g. a linear epitope in a domain). Alternatively, the epitope may consist of a plurality of non-contiguous amino acids (or amino acid sequences) located within either or both of the aforementioned regions of the PDGF-B molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in *Antibodies*, Harlow and Lane (Cold Spring Harbor Press, Cold Spring Harbor, NY). Other methods include alanine scanning mutational analysis, peptide blot analysis (Reineke (2004) Methods Mol Biol 248:443-63), peptide cleavage analysis, crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the peptides containing the deuterium-labeled residues that contain specific amino acids with which the antibody interacts. See, e.g., Ehring (1999) *Analytical Biochemistry* 267(2):252-259; Engen and Smith (2001) *Anal. Chem.* 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

In certain embodiments, the anti-PDGF-B antibodies or antigen-binding fragments thereof bind an epitope within any one or more of the regions exemplified in human PDGF-B, as exemplified in SEQ ID NO: 41, or to a fragment thereof.

The present disclosure includes human anti-PDGF-B antibodies that bind to the same epitope, or a portion of the epitope, as any of the specific exemplary antibodies described herein, or an antibody having the CDR sequences of any of the exemplary antibodies described herein. Likewise, the present disclosure also includes anti-PDGF-B antibodies that compete for binding to PDGF-B or a PDGF-B fragment with any of the specific exemplary antibodies described herein, or an antibody having the CDR sequences of any of the exemplary antibodies described herein.

One can easily determine whether an antibody binds to the same epitope as, or competes for binding with, a reference anti-PDGF-B antibody by using routine methods known in the art. For example, to determine if a test antibody binds to the same epitope as a reference anti-PDGF-B antibody of the disclosure, the reference antibody is allowed to bind to a PDGF-B protein or peptide under saturating conditions. Next, the ability of a test antibody to bind to the PDGF-B molecule is assessed. If the test antibody is able to bind to PDGF-B following saturation binding with the reference anti-PDGF-B antibody, it can be concluded that the test antibody binds to a different epitope than the reference anti-PDGF-B antibody. On the other hand, if the test antibody is not able to bind to the PDGF-B protein following saturation binding with the reference anti-PDGF-B antibody, then the test antibody may bind to the same epitope as the epitope bound by the reference anti-PDGF-B antibody of the disclosure.

To determine if an antibody competes for binding with a reference anti-PDGF-B antibody, the above-described binding methodology is performed in two orientations: In a first orientation, the reference antibody is allowed to bind to a PDGF-B protein under saturating conditions followed by assessment of binding of the test antibody to the PDGF-B molecule. In a second orientation, the test antibody is allowed to bind to a PDGF-B molecule under saturating conditions followed by assessment of binding of the reference antibody to the PDGF-B molecule. If, in both orientations, only the first (saturating) antibody is capable of binding to the PDGF-B molecule, then it is concluded that the test antibody and the reference antibody compete for binding to PDGF-B. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The disclosure encompasses a human anti-PDGF-B monoclonal antibody conjugated to a therapeutic moiety ("immunoconjugate"), such as an agent that is capable of reducing the severity of pulmonary arterial hypertension, or to ameliorate at least one symptom associated with pulmonary arterial hypertension. As used herein, the term "immunoconjugate" refers to an antibody that is chemically or biologically linked to a radioactive agent, a cytokine, an interferon, a target or reporter moiety, an enzyme, a toxin, or a therapeutic agent. The antibody may be linked to the radioactive agent, cytokine, interferon, target or reporter moiety, enzyme, toxin, or therapeutic agent at any location along the molecule so long as it is able to bind its target. An example of immunoconjugate is an antibody drug conjugate. In some embodiments, the agent may be a second different antibody to PDGF-B, or to a cytokine such as IL-1, IL-6, or a chemokine such as TGF-β. The type of therapeutic moiety that may be conjugated to the anti-PDGF-B antibody will take into account the condition to be treated and the desired therapeutic effect to be achieved. Examples of suitable agents for forming immunoconjugates are known in the art; see for example, WO 05/103081. The preparation of immunoconjugates and immunotoxins is generally well known in the art (see, e.g., U.S. Pat. No. 4,340,535). Immunoconjugates are described in detail, for example, in U.S. Pat. Nos. 7,250,492, 7,420,040 and 7,411,046, each of which is incorporated herein in their entirety.

Multi-Specific Antibodies

The antibodies of the present disclosure may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, the present disclosure includes bi-specific antibodies wherein one arm of an immunoglobulin is specific for the N-terminal region of PDGF-B, or a fragment thereof, and the other arm of the immunoglobulin is specific for the C-terminal region of PDGF-B, or a second therapeutic target, or is conjugated to a therapeutic moiety. An exemplary bi-specific antibody format that can be used in the context of the present disclosure involves the use of a first immunoglobulin (Ig) $C_{H3}$ domain and a second Ig $C_{H3}$ domain, wherein the first and second Ig $C_{H3}$ domains differ from one another by at least one amino acid, and wherein at least one amino acid difference reduces binding of the bi-specific antibody to PDGF-B as compared to a bi-specific antibody lacking the amino acid difference. Variations on the bi-specific antibody format described above are contemplated within the scope of the present disclosure.

Other exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The disclosure provides therapeutic compositions comprising the anti-PDGF-B antibodies or antigen-binding fragments thereof as discussed herein. The therapeutic compositions in accordance with the disclosure can be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN®), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When the antibody of the present disclosure is used for preventing or treating pulmonary arterial hypertension, it is advantageous to intravenously administer the antibody of the present disclosure normally at a single dose of about 0.1 to about 100 mg/kg body weight, more preferably about 5 to about 100, about 10 to about 90, or about 20 to about 70 mg/kg body weight. Depending on the severity of the condition, the frequency and the duration of the treatment can be adjusted. In certain embodiments, the antibody or antigen-binding fragment thereof of the disclosure can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present disclosure is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles for drug delivery have also been described in, for example, U.S. Pat. Nos. 8,277,812, 8,258,256, 8,257,740, 8,246,995, 8,236,330, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but certainly are not limited to AUTOPEN® (Owen Mumford, Inc., Woodstock, UK), DISETRONIC™ pen (Disetronic Medical Systems, Burghdorf, Switzerland), HUMALOG MIX 75/25™ pen, HUMALOG® pen, HUMALIN 70/30™ pen (Eli Lilly and Co., Indianapolis, IN), NOVOPEN® I, II and III (Novo Nordisk, Copenhagen, Denmark), NOVOPEN JUNIOR™ (Novo Nordisk, Copenhagen, Denmark), BD pen (Becton Dickinson, Franklin Lakes, NJ), OPTIPEN®, OPTIPEN® PRO, OPTIPEN® STARLET, and OPTICLIK™ (Sanofi-aventis, Frankfurt, Germany), to name only a few. Examples of disposable pen delivery devices having applications in subcutaneous delivery of a pharmaceutical composition of the present disclosure include, but certainly are not limited to the SOLOSTAR® pen (Sanofi-aventis), the FLEXPEN® (Novo Nordisk), and the KWIKPEN® (HUMALOG®), the SURECLICK® Autoinjector), the PENLET (Haselmeier, Stuttgart, Germany), the EPIPEN® (Mylan® and the HUMIRA® Pen (Abbott Labs, Abbott Park, IL), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms. The present disclosure includes an injection device (e.g., a pre-filled syringe or pre-filled auto-injector) or a vial (e.g., a glass or plastic vial) comprising an antibody or antigen-binding fragment of the present disclosure or pharmaceutical composition thereof which includes a pharmaceutically acceptable carrier.

Therapeutic Uses of the Antibodies

In certain embodiments of the disclosure, the present antibodies are useful for treating pulmonary arterial hypertension, or at least one symptom associated with pulmonary arterial hypertension. The antibodies of the disclosure are also contemplated for prophylactic use in patients at risk for developing pulmonary arterial hypertension. These patients include the elderly, or patients immunocompromised due to illness or treatment with immunosuppressive therapeutics. It is contemplated that the antibodies of the disclosure may be used alone, or in conjunction with a second agent, or third agent for treating pulmonary arterial hypertension, or for alleviating at least one symptom or complication associated with pulmonary arterial hypertension. The second or third agents may be delivered concurrently with the antibodies of the disclosure, or they may be administered separately, either before or after the antibodies of the disclosure. A patient that may receive an antibody or antigen-binding fragment of the disclosure or a pharmaceutical composition thereof includes, for example, an animal such as a mammal such as a human (e.g., an elderly human, for example, 65 years of age or older), rabbit, mouse, rat, cow, pig, dog, primate, horse or sheep.

In a further embodiment of the disclosure the present antibodies are used for the preparation of a pharmaceutical composition for treating patients suffering from pulmonary arterial hypertension.

Combination Therapies

The present disclosure includes compositions and therapeutic formulations comprising any of the anti-PDGF-B antibodies described herein in combination with one or more additional therapeutically active components, and methods of treatment comprising administering such combinations to subjects in need thereof.

The anti-PDGF-B antibodies of the present disclosure may be co-formulated with and/or administered in combination with, e.g., a VEGF antagonist, e.g., a "VEGF-trap" such as aflibercept or other VEGF-inhibiting fusion protein as set forth in U.S. Pat. No. 7,087,411, an anti-VEGF antibody or antigen binding fragment thereof (e.g., bevacizumab, ranibizumab), a small molecule kinase inhibitor of VEGF receptor (e.g., sunitinib, sorafenib or pazopanib), or an anti-VEGF receptor antibody. The anti-PDGF-B antibody may also be combined with a PDGF ligand antagonist (e.g., an anti-PDGF-BB antibody, an anti-PDGF-DD antibody, an anti-PDGF-CC antibody, an anti-PDGF-AB antibody, or other PDGF ligand antagonist such as an aptamer [e.g., an anti-PDGF-B aptamer such as Fovista™, Ophthotech Corp., Princeton, NJ], an antisense molecule, a ribozyme, an siRNA, a peptibody, a nanobody or an antibody fragment directed against a PDGF ligand). In other embodiments, the anti-PDGF-B antibodies of the present disclosure may be co-formulated with and/or administered in combination with an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist specific for EGFRvlll (e.g., an antibody that specifically binds EGFRvlll), a cMET anagonist (e.g., an anti-cMET antibody), an IGF1 R antagonist (e.g., an anti-IGF1 R antibody), or a B-raf inhibitor (e.g., vemurafenib, sorafenib, GDC-0879, PLX-4720). In certain instances, the anti-PDGF-B antibodies of the present disclosure are combined, co-formulated and/or administered in combination with a PDGFR-alpha inhibitor (e.g., an anti-PDGFR-alpha antibody), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1 H685P), etc. Other agents that may be beneficially administered in combination with the anti-PDGF-B antibodies of the disclosure include cytokine inhibitors, including small-molecule cytokine inhibitors and antibodies that bind to cytokines such as IL-1, IL-2, IL-3, IL-4, IL-5, IL-6, IL-8, IL-9, IL-, IL-12, IL-13, IL-17, IL-18, or to their respective receptors.

The anti-PDGF-B antibodies of the disclosure may also be administered and/or co-formulated in combination with antivirals, antibiotics, analgesics, corticosteroids, steroids, oxygen, antioxidants, metal chelators, IFN-gamma, and/or NSAIDs. The anti-PDGF-B antibodies of the disclosure may also be administered as part of a treatment regimen that also includes radiation treatment and/or conventional chemotherapy (e.g., in the context of methods of treating cancer or inhibiting tumor growth).

Any of the aforementioned additional therapeutically active components may be administered in combination with any of the anti-PDGF-B antibodies of the present disclosure for the treatment of any disease or disorder in which administration of an anti-PDGFR-beta antibody is beneficial, including, e.g., any of the eye diseases, fibrotic diseases, vascular diseases and/or cancers mentioned herein. For example, in the context of treating an eye disease (e.g., wet AMD, diabetic retinopathy, CRVO, or any of the other eye diseases described herein), an anti-PDGF-B antibody of the present disclosure may be co-formulated with, and/or administered in combination with a VEGF antagonist, e.g., a "VEGF-trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab).

In exemplary embodiments in which an anti-PDGF-B antibody of the disclosure is administered in combination with a VEGF antagonist (e.g., a VEGF trap such as aflibercept), including administration of co-formulations comprising an anti-PDGF-B antibody and a VEGF antagonist, the individual components may be administered to a subject and/or co-formulated using a variety of dosage combinations. For example, the anti-PDGF-B antibody may be administered to a subject and/or contained in a co-formulation in an amount selected from the group consisting of 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.5 mg, 2.0 mg, 2.5 mg, 3.0 mg, 3.5 mg, 4.0 mg, 4.5 mg, 5.0 mg, and 5.5 mg; and the VEGF antagonist (e.g., a VEGF trap such as aflibercept) may be administered to the subject and/or contained in a co-formulation in an amount selected from the group consisting of 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg and 3.0 mg. Exemplary anti-PDGF-B antibody/aflibercept dosage combinations of the present disclosure include, e.g.: (i) 0.2 mg anti-PDGF-B antibody+2 mg aflibercept; (ii) 0.5 mg anti-PDGF-B antibody+2 mg aflibercept; (iii) 1 mg anti-PDGF-B antibody+2 mg aflibercept; (iv) 3 mg anti-PDGF-B antibody+2 mg aflibercept; and (v) 4 mg anti-PDGFR-beta antibody+2 mg aflibercept. The combinations/co-formulations may be administered to a subject according to any of the administration regimens disclosed elsewhere herein, including, e.g., once every week, once every 2 weeks, once every 3 weeks, once every month, once every 2 months, once every 3 months, once every 4 months, once every 5 months, once every 6 months, etc.

The additional therapeutically active component(s) may be administered to a subject prior to administration of an anti-PDGF-B antibody of the present disclosure. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-PDGF-B antibody of the present disclosure. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-PDGF-B antibody.

"Concurrent" administration, for purposes of the present disclosure, includes, e.g., administration of an anti-PDGF-B antibody and an additional therapeutically active component to a subject in a single dosage form (e.g., co-formulated), or in separate dosage forms administered to the subject within about 30 minutes or less of each other. If administered in separate dosage forms, each dosage form may be administered via the same route (e.g., both the anti-PDGFR-beta antibody and the additional therapeutically active component may be administered intravitreally, subcutaneously, etc.); alternatively, each dosage form may be administered via a different route (e.g., the anti-PDGF-B antibody may be administered Intravitreally, and the additional therapeutically active component may be administered systemically). In any event, administering the components in a single dosage from, in separate dosage forms by the same route, or in separate dosage forms by different routes are all considered "concurrent administration," for purposes of the present disclosure. For purposes of the present disclosure, administration of an anti-PDGF-B antibody "prior to", "concurrent with," or "after" (as those terms are defined herein above) administration of an additional therapeutically active component is considered administration of an anti-PDGF-B antibody "in combination with" an additional therapeutically active component).

The present disclosure includes pharmaceutical compositions in which an anti-PDGFR-beta antibody of the present disclosure is co-formulated with one or more of the additional therapeutically active component(s) as described elsewhere herein.

The present disclosure also includes additional therapeutic compositions comprising a combination of a PDGF antagonist and a VEGF antagonist. PDGF antagonists according to this aspect of the disclosure include PDGF receptor antagonists as well as PDGF ligand antagonists. Likewise, VEGF antagonists according to this aspect of the disclosure include VEGF receptor antagonists as well as VEGF ligand antagonists.

The additional therapeutically active component(s) may be administered prior to, concurrent with, or after the administration of the anti-PDGF-B antibody of the present disclosure. For purposes of the present disclosure, such administration regimens are considered the administration of an anti-PDGF-B antibody "in combination with" one or more additional therapeutically active component(s).

Diagnostic Uses of the Antibodies

The anti-PDGF-B antibodies of the present disclosure may also be used to detect and/or measure PDGF-B in a sample, e.g., for diagnostic purposes. Exemplary diagnostic assays for PDGF-B may comprise, e.g., contacting a sample, obtained from a patient, with an anti-PDGF-B antibody of the disclosure, wherein the anti-PDGF-B antibody is labeled with a detectable label or reporter molecule or used as a capture ligand to selectively isolate PDGF-B from patient samples. Alternatively, an unlabeled anti-PDGF-B antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure PDGF-B in a sample include enzyme-linked immunosorbent assay (ELISA), radioimmunoassay (RIA), and fluorescence-activated cell sorting (FACS).

Samples that can be used in PDGF-B diagnostic assays according to the present disclosure include any tissue or fluid sample obtainable from a patient, which contains detectable quantities of either PDGF-B, or fragments thereof, under normal or pathological conditions. Generally, levels of PDGF-B in a particular sample obtained from a healthy patient (e.g., a patient not afflicted with pulmonary arterial hypertension) will be measured to initially establish a baseline, or standard, level of PDGF-B. This baseline level of PDGF-B can then be compared against the levels of PDGF-B measured in samples obtained from individuals suspected of having pulmonary arterial hypertension related condition, or symptoms associated with such condition.

The antibodies specific for PDGF-B may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In some embodiments, the label may be detectable label such as a radionuclide, a fluorescent dye or a MRI-detectable label. Detectable labels may be linked to the antibodies wherein such antibodies may be used in imaging assays.

Methods of Treatment

The present disclosure provides methods for treating a subject having pulmonary arterial hypertension. The methods generally include administering to the subject a therapeutically effective amount of an anti-PDGF-B antibody, or antigen-binding fragment thereof.

In some aspects, administration of the anti-PDGF-B antibody, or antigen-binding fragment thereof, inhibits thickening of the pulmonary artery in the subject, e.g., inhibit further thickening of the pulmonary artery in the subject from baseline, e.g., at diagnosis. The thickening of the pulmonary artery may be determined by, for example, chest CT (such as, unenhanced axial 10 mm CT sections), and used to calculate main pulmonary artery diameter (mPA). The main pulmonary artery diameter in normal subjects is about 2.4 cm to about 3.0 cm. Main pulmonary artery diameter in subjects with pulmonary arterial hypertension is about 3.1 cm to about 3.8 cm, or greater. See, e.g., Edwards, et al. (1998) *Br J Radiol* 71(850):1018-20.

In other aspects, administration of the anti-PDGF-B antibody, or antigen-binding fragment thereof, increases stroke volume and/or stroke volume to end systolic volume ratio ("SV/ESV") in the subject. "Stroke volume" ("SV") is the volume of blood pumped from the right or left ventricle per single contraction. Stroke volume may be calculated using measurements of ventricle volumes from an echocardiogram and calculated by subtracting the volume of the blood in the ventricle at the end of a beat (called "end-systolic volume," "EDV") from the volume of blood just prior to the beat (called "end-diastolic volume," "ESV"). Stroke volume may also be calculated, e.g., as cardiac out put measured by thermodilution during right heart catheterization divided by heart rate or as EDV minus ESV and indexed for body surface area. The term stroke volume can apply to each of the two ventricles of the heart. The stroke volumes for each ventricle are generally equal, both being approximately 70 mL in a healthy subjects. The SV/ESV for healthy subjects is about 0.9 to about 2.2 and the SV/ESV for subjects having PAH is about 0.2 to about 0.9. See, e.g. Brewis, et al. (2016) *Int J Cardiol* 218:206-211.

In yet other aspects, administration of the anti-PDGF-B antibody, or antigen-binding fragment thereof, increases right ventricle cardiac output and/or cardiac index (CI) in the subject. "Cardiac output" ("CO") is defined as the amount of blood pumped by a ventricle in unit time. "Cardiac index" ("CI") is a haemodynamic parameter that relates the cardiac output (CO) from left ventricle in one minute to "body surface area" ("BSA"), thus relating heart performance to the size of the individual. Echocardiographic techniques and radionuclide imaging techniques can be used to estimate real-time changes in ventricular dimensions, thus computing stroke volume, which when multiplied by heart rate, gives cardiac output, and BSA may be calculated using any one of the formulas known to one of ordinary skill in the art including, for example, the Du Bois formula (Verbraecken, J, et al. (2006) *Metabolism—Clin Exper* 55(4):515-24) or the Mosteller formula (Mosteller (1987) *N Engl J Med* 317: 1098). Subjects that do not have PAH have a cardiac output in the range of about 4.0-8.0 L/min and a cardiac index of about 2.6 to about 4.2 L/minute per square meter. Subjects that have PAH have a cardiac index of about 1.9 to about 2.3 L/minute per square meter (Ryan and Archer (2016) *Circ Res* 115:176-188).

Administration of the anti-PDGF-B antibody, or antigen-binding fragment thereof, to a subject having PAH in the methods of the present disclosure may improve other hemodynamic measurements in a subject having PAH, such as, for example, right atrium pressure, pulmonary artery pressure, pulmonary capillary wedge pressure in the presence of end expiratory pressure, systemic artery pressure, heart beat, pulmonary vascular resistance, and/or systemic vascular resistance. Methods and devices for measuring right atrium pressure, pulmonary artery pressure, pulmonary capillary wedge pressure in the presence of end expiratory pressure, systemic artery pressure, heart beat, pulmonary vascular resistance, and/or systemic vascular resistance are known to one of ordinary skill in the art.

Subjects that do not have PAH have a right atrium pressure of about 1 mm Hg to about 5 mm Hg; subjects that have PAH have a right atrium pressure of about 11 mm Hg to about 13 mm Hg.

Subjects that do not have PAH have a pulmonary artery pressure of about 9 mm Hg to about 20 mm Hg; subjects that have PAH have a pulmonary artery pressure of about 57 mm Hg to about 61 mm Hg.

Subjects that do not have PAH have a pulmonary capillary wedge pressure in the presence of end expiratory pressure of about 4 mm Hg to about 12 mm Hg; subjects that have PAH have a pulmonary capillary wedge pressure in the presence of end expiratory pressure of about 9 mm Hg to about 11 mm Hg.

Subjects that do not have PAH have a systemic artery pressure of about 90 mm Hg to about 96 mm Hg; subjects that have PAH have a systemic artery pressure of about 87 mm Hg to about 91 mm Hg.

Subjects that do not have PAH have a heartbeat of about 60 beats per minute (bpm) to about 90 bpm; subjects that have PAH have a systemic artery pressure of about 84 bpm 88 bpm.

Subjects that do not have PAH have a pulmonary vascular resistance of about 20 dynes s/cm$^5$ to about 130 dynes s/cm$^5$ (or about 0.25 to about 1.625 wood units) subjects that have PAH have a pulmonary vascular resistance of about 1200 dynes s/cm$^5$ to about 1360 dynes s/cm$^5$ (or about 15 to about 17 wood units).

Subjects that do not have PAH have a systemic vascular resistance of about 700 dynes s/cm$^5$ to about 1600 dynes s/cm$^5$ (or about 9 to about 20 wood units) subjects that have PAH have a systemic vascular resistance of about 1840 dynes s/cm$^5$ to about 2000 dynes s/cm$^5$ (or about 23 to about 25 wood units).

The methods of the present disclosure may also improve other clinical parameters, such as pulmonary function, in the subject being treated. For example, during or following a treatment period a subject may have an increased exercise capacity or activity, as measured by, for example, a test of 6-minute walking distance (6 MWD) or measure of activity, or lowering Borg dyspnea index (BDI).

The methods of the present disclosure may also improve one or more quality of life parameters versus baseline, for example an increase in score on at least one of the SF-36® health survey functional scales; an improvement versus baseline in the severity of the condition, for example by movement to a lower WHO functional class; and/or an increased longevity.

Any suitable measure of exercise capacity can be used to determine whether a subject has an increased exercise capacity or activity. One suitable measure is a 6-minute walk test (6MWT), which measures how far the subject can walk in 6 minutes, i.e., the 6-minute walk distance (6MWD). Another suitable measure is the Borg dyspnea index (BDI), which is a numerical scale for assessing perceived dyspnea (breathing discomfort). It measures the degree of breathlessness after completion of the 6-minute walk test (6MWT), where a BDI of 0 indicates no breathlessness and 10 indicates maximum breathlessness. In one embodiment, the methods of the disclosure provide to the subject an increase from baseline in the 6MWD by at least about 10 minutes, e.g., about 10, 15, 20, or about 30 minutes. In another embodiment, following a 6MWT the methods of the disclosure provide to the subject a lower from baseline BDI by at least about 0.5 to about 1.0 index points.

Any suitable measure quality of life may be used. For example, the SF-36® health survey provides a self-reporting, multi-item scale measuring eight health parameters: physical functioning, role limitations due to physical health problems, bodily pain, general health, vitality (energy and fatigue), social functioning, role limitations due to emotional problems, and mental health (psychological distress and psychological well-being). The survey also provides a physical component summary and a mental component summary. In one embodiment, the methods of the disclosure provide to the subject an improvement versus baseline in at least one of the SF-36 physical health related parameters (physical health, role-physical, bodily pain and/or general health) and/or in at least one of the SF-36 mental health related parameters (vitality, social functioning, role-emotional and/or mental health). Such an improvement can take the form of an increase of at least 1, for example at least 2 or at least 3 points, on the scale for any one or more parameters.

The methods of the present disclosure may also improve the prognosis of the subject being treated. For example, the methods of the disclosure may provide to the subject a reduction in probability of a clinical worsening event during the treatment period, and/or a reduction from baseline in serum brain natriuretic peptide (BNP) or NT pro-BNP or its N-terminal prohormone, NT-pro-BNP concentration, wherein, at baseline, time from first diagnosis of the condition in the subject is not greater than about 2 years.

Time from first diagnosis, in various aspects, can be, for example, not greater than about 1.5 years, not greater than about 1 year, not greater than about 0.75 year, or not greater than about 0.5 year. A clinical worsening event (CWE) includes death, lung transplantation, hospitalization for the PAH, atrial septostomy, initiation of additional pulmonary hypertension therapy or a combination thereof. Time to clinical worsening of PAH is defined as the time from initiation of treatment to the first occurrence of a CWE.

In one embodiment, the methods of the disclosure provide a reduction from baseline of at least about 15%, for example at least about 25%, at least about 50% or at least about 75%, in BNP or NT-pro-BNP concentration.

In one embodiment, the methods of the disclosure provide a reduction of at least about 25%, for example at least about 50%, at least about 75%> or at least about 80%, in probability of death, lung transplantation, hospitalization for pulmonary arterial hypertension, atrial septostomy and/or initiation of additional pulmonary hypertension therapy during the treatment period.

The methods of the present disclosure may also prolong the life (extend survival time) of a subject having PAH, from a time of initiation of treatment by, for example, at least about 30 days.

The therapeutically effective amount of an anti-PDGF-B antibody, or antigen-binding fragment thereof, for use in the methods of the disclosure may be from about 0.05 mg to about 600 mg; e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, or about 1000 mg, of the respective antibody.

The amount of anti-PDGF-B antibody, or antigen-binding fragment thereof, contained within an individual dose may be expressed in terms of milligrams of antibody per kilogram of patient body weight (i.e., mg/kg). For example, an anti-PDGF-B antibody, or antigen-binding fragment thereof, may be administered to a patient at a dose of about 0.0001 to about 50 mg/kg of patient body weight (e.g. 0.1 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 10.5 mg/kg, 11.0 mg/kg, 11.5 mg/kg, 12.0 mg/kg, 12.5 mg/kg, 13.0 mg/kg, 13.5 mg/kg, 14.0 mg/kg, 14.5 mg/kg, 15.0 mg/kg, 15.5 mg/kg, 16.0 mg/kg, 16.5 mg/kg, 17.0 mg/kg, 17.5 mg/kg, 18.0 mg/kg, 18.5 mg/kg, 19.0 mg/kg, 19.5 mg/kg, 20.0 mg/kg, etc.).

Multiple doses of an anti-PDGF-B antibody, or antigen-binding fragment thereof, or a pharmaceutical composition comprising an anti-PDGF-B antibody, or antigen-binding fragment thereof, may be administered to a subject over a defined time course. The methods according to this aspect of the disclosure comprise sequentially administering to a subject multiple doses of an active ingredient of the disclosure. As used herein, "sequentially administering" means that each dose of an active ingredient is administered to the subject at a different point in time, e.g., on different days separated by a predetermined interval (e.g., hours, days, weeks or months). The present disclosure includes methods which comprise sequentially administering to the patient a single initial dose of an active ingredient, followed by one or more secondary doses of the active ingredient, and optionally followed by one or more tertiary doses of the active ingredient.

The terms "initial dose," "secondary doses," and "tertiary doses," refer to the temporal sequence of administration of an anti-PDGF-B antibody, or antigen-binding fragment thereof, or of a combination therapy of the disclosure. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-PDGF-B antibody, or antigen-binding fragment thereof, but may differ from one another in terms of frequency of administration. In certain embodiments, however, the amount of anti-PDGF-B antibody, or antigen-binding fragment thereof, contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of an anti-PDGF-B antibody, or antigen-binding fragment thereof, which is administered to a patient prior to the administration of the very next dose in the sequence with no intervening doses.

The methods according to this aspect of the disclosure may comprise administering to a patient any number of secondary and/or tertiary doses. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician, depending on the needs of the individual patient following clinical examination.

In some embodiments, an anti-PDGF-B antibody, or antigen-binding fragment thereof, may be administered as a monotherapy (i.e., as the only therapeutic agent). In other embodiments, an anti-PDGF-B antibody, or antigen-binding fragment thereof, may be administered in combination with one or more additional therapeutic agents.

In the combination methods which comprise administering an anti-PDGF-B antibody, or antigen-binding fragment thereof, and at least one additional therapeutic agent to the subject, the antibody and the additional therapeutic agent may be administered to the subject at the same or substantially the same time, e.g., in a single therapeutic dosage, or in two separate dosages which are administered simultaneously or within less than about 5 minutes of one another. Alternatively, the antibody and the additional therapeutic agent may be administered to the subject sequentially, e.g., in separate therapeutic dosages separated in time from one another by more than about 5 minutes.

Accordingly, in one embodiment, the methods further comprise administering a therapeutically effective amount of at least one therapeutic agent selected from the group consisting of an anticoagulant, a diuretic, a cardiac glycoside, a calcium channel blocker, a vasodilator, a prostacyclin analogue, an endothelium antagonist, a phosphodiesterase inhibitor, an endopeptidase inhibitor, a lipid lowering agent, and a thromboxane inhibitor. In one embodiment, the methods of the disclosure further comprise administering a therapeutically effective amount of at least one or more additional therapeutic antibody or antibodies, or antigen-binding fragment or fragments thereof. In one embodiment, the one or more additional antibody or antibodies are selected from the group consisting of an anti-Grem 1 antibody or antibodies, an anti-PDGFRβ antibody or antibodies, an anti-TLR4 antibody or antibodies, an anti-TLR2 antibody or antibodies, an anti-EDN1 antibody or antibodies, and an anti-ASIC1 antibody or antibodies.

Examples of suitable anticoagulants include, but are not limited to, e.g. warfarin useful in the treatment of patients with pulmonary hypertension having an increased risk of thrombosis and thromboembolism.

Examples of suitable calcium channel blockers include, but are not limited to, diltiazem, felodipine, amlodipine and nifedipine.

Suitable vasodilators include, but are not limited to, e.g. prostacyclin, epoprostenol, treprostinil and nitric oxide (NO).

Suitable exemplary phosphodiesterase inhibitors include, but are not limited to, particularly phospho-diesterase V inhibitors such as e.g. tadalafil, sildenafil and vardenafil.

Examples of suitable endothelin antagonists include, but are not limited to, e.g. bosentan and sitaxentan.

Suitable prostacyclin analogues include, but are not limited to, e.g. ilomedin, treprostinil and epoprostenol.

Suitable lipid lowering agents include, but are not limited to, e.g. HMG CoA reductase inhibitors such as simvastatin, pravastatin, atorvastatin, lovastatin, itavastatin, fluvastatin, pitavastatin, rosuvastatin, ZD-4522 and cerivastatin Diuretics suitable for use in the combination therapies of the disclosure include, but are not limited to, e.g. chlorthalidon, indapamid, bendro-flumethiazid, metolazon, cyclopenthiazid, polythiazid, mefrusid, ximapid, chlorothiazid and hydrochlorothiazid.

Examples of other therapeutics agents include, but are not limited to, e.g. ACE inhibitors such as enalapril, ramipril, captopril, cilazapril, trandolapril, fosinopril, quinapril, moexipril, lisinopril and perindopril, or ATII inhibitors such as losartan, candesartan, irbesartan, embusartan, valsartan and telmisartan, or iloprost, betaprost, L-arginine, omapatrilat, oxygen, and/or digoxin.

The methods may also include the combined use of kinase inhibitors (e.g., BMS-354825, canertinib, erlotinib, gefitinib, imatinib, lapatinib, lestaurtinib, lonafarnib, pegaptanib, pelitinib, semaxanib, tandutinib, tipifarnib, vatalanib, lonidamine, fasudil, leflunomide, bortezomib, imatinib, erlotinib and glivec) and/or elastase inhibitors.

The additional therapeutically active component(s) may be administered to a subject prior to administration of an anti-PDGF-B antibody. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-PDGF-B antibody, or antigen-binding fragment thereof. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component.

In yet other embodiments, the additional therapeutically active component(s) may be administered to a subject concurrent with administration of anti-PDGF-B antibody, or antigen-binding fragment thereof, of the present disclosure. "Concurrent" administration, for purposes of the present disclosure, includes, e.g., administration of an anti-PDGF-B antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-PDGF-B antibody and the additional therapeutically active component may be administered intravenously, subcutaneously, intravitreally, etc.); alternatively, each dosage form may be administered via a different route (e.g., the anti-PDGF-B antibody may be administered locally (e.g., intravitreally) and the additional therapeutically active component may be administered systemically). In any event, administering the components in a single dosage from, in separate dosage forms by the same route, or in separate dosage forms by different routes are all considered "concurrent administration," for purposes of the present disclosure. For purposes of the present disclosure, administration of an anti-PDGF-B antibody "prior to," "concurrent with," or "after" (as those terms are defined herein above) administration of an additional therapeutically active component is considered administration of an anti-PDGF-B antibody, or antigen-binding fragment thereof, "in combination with" an additional therapeutically active component).

EXAMPLES

The following examples are put forth so as to provide those of ordinary skill in the art with a complete disclosure and description of how to make and use the methods and compositions of the invention, and are not intended to limit the scope of what the inventors regard as their invention. Unless indicated otherwise, parts are parts by weight, molecular weight is average molecular weight, temperature is in degrees Celsius, and pressure is at or near atmospheric.

The terms REGN13335 and H4H13145P are used interchangeably herein. Further, the terms REGN15171 and H4H13132P are used interchangeably herein.

Example 1. Screening and In-Vitro Characterization of Anti-PDGF Antibodies

Adam6/VI-3, ULC1633 and ULC1635 mice were utilized for the isolation and primary screening of the anti-PDGF-B antibodies. The considerations included requiring monkey crossers, and mouse crossers, and required the blocking of PDGF-BB and PDGF-AB signaling. The crossing to DD was considered to be highly unlikely, and further no cross reactivity to PDGF AA was expected. The AF-220-NA goat a-human PDGFBB polyclonal neutralizing antibody was used as the control/comparator antibody.

PES sorted B-cells were isolated from 12 mice. Adam6/VI-3, ULC1633 and ULC1635 mice were used for sorting antigen biotin-hPDGFBB or mPDGFBB, and 6387 B-cells were collected. Eleven plates of B-cells were processed (3614 B-cells) and VH was only amplified for ULC mice. A total of 1056 PCR pairs were cloned into hIgG1 BST plasmids. Primary screening for Ag+ samples was performed by ELISA. A total of 854 Ag+ (81%) samples were identified (>1000 MFI to hPDFGBB (Peprotech)). Secondary screening was performed on the Ag+ samples by use of blocking ELISA, blocking Luminex, Biacore, and Bioassay. Mouse crossers were analyzed by use of mouse Biacore and Bioassay. The screening results of the monoclonal antibodies from the VI-3 mice are summarized in FIG. 1 and Table 1 below.

TABLE 1

Screening results of the monoclonal antibodies from the VI-3 mice.

| Antibody | Strain | Bin | $K_D$ [M] | $t_{1/2}$ (min) | Blocking Bioassay (%) | Blocking Luminex (h) (%) | % Blocking Luminex (m) (%) | Blocking ELISA (h) (%) |
|---|---|---|---|---|---|---|---|---|
| H4H13163B | Adam6/VI3 | 3 | 4.60E−11 | ≥116 | 61.9 | 96.7 | 96.9 | −7.2 |
| H4H13151B | Adam6/VI3 | 5 | 6.49E−10 | 2.8 | 67.3 | 80.2 | 73.0 | 13.6 |
| H4H13132B | Adam6/VI3 | 3 | 9.59E−11 | ≥116 | 68.2 | 88.1 | 88.8 | 14.1 |
| H4H13143B | Adam6/VI3 | 5 | 1.71E−10 | 20.3 | 68.6 | 76.7 | 84.2 | 11.3 |
| H4H13153B | Adam6/VI3 | 2 | 6.55E−10 | 1.8 | 70.0 | 87.3 | 87.4 | 7.1 |
| H4H13169B | Adam6/VI3 | 3 | 4.86E−10 | 3.3 | 70.2 | 85.1 | 82.7 | 0.0 |
| H4H13159B | Adam6/VI3 | 5 | 1.10E−10 | 26.5 | 71.2 | 87.0 | 89.3 | 5.5 |
| H4H13157B | Adam6/VI3 | 3 | 6.45E−10 | 3.6 | 73.2 | 98.3 | 98.3 | 8.2 |
| H4H13155B | Adam6/VI3 | 5 | 1.25E−10 | 36.1 | 74.4 | 88.5 | 71.6 | 10.7 |
| H4H13170B | Adam6/VI3 | 4 | 5.82E−10 | 18.5 | 79.0 | 45.8 | 3.1 | 0.0 |
| H4H13162B | Adam6/VI3 | 5 | 2.81E−11 | ≥116 | 81.4 | 94.2 | 94.7 | 9.3 |
| H4H13166B | Adam6/VI3 | 4 | 5.97E−11 | ≥116 | 87.1 | 36.1 | 0.0 | 0.9 |
| H4H13167B | Adam6/VI3 | 4 | 7.87E−11 | ≥116 | 89.2 | 22.8 | 0.0 | 0.0 |
| H4H13127B | Adam6/VI3 | 5 | 3.54E−11 | ≥116 | 94.3 | 3.9 | 6.5 | 11.8 |
| H4H13152B | Adam6/VI3 | 5 | 1.56E−09 | 3.7 | 100.0 | 51.2 | 49.8 | 9.1 |
| H4H13145B | Adam6/VI3 | 5 | 6.43E−11 | ≥116 | 100.0 | 64.8 | 73.1 | 59.1 |
| H4H13148B | Adam6/VI3 | 5 | 2.94E−11 | ≥116 | 110.2 | 95.1 | 25.6 | 52.2 |

Figure 2:
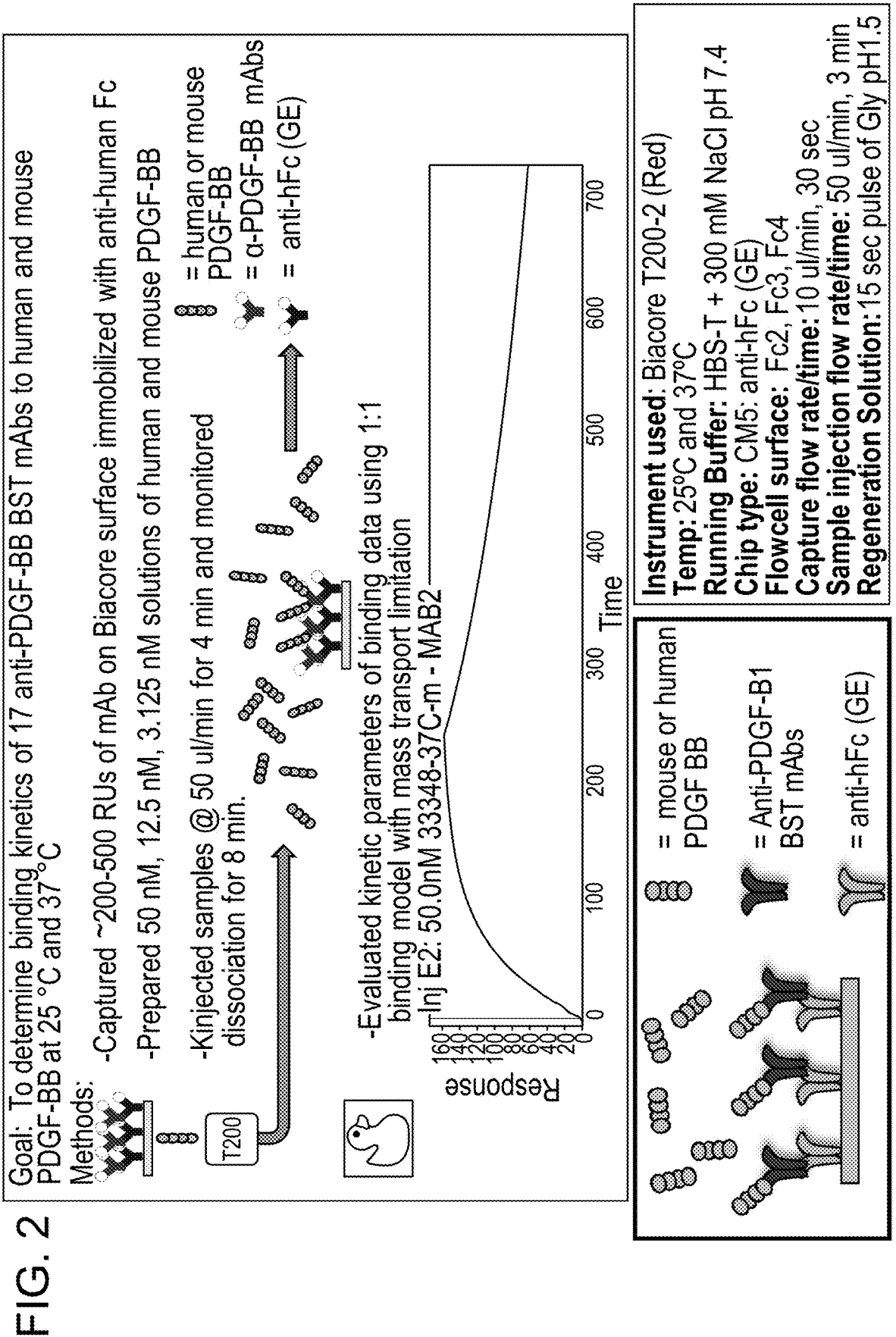
FIG. 2 is a schematic depicting the study performed for determining the binding Kinetics of 17 anti-PDGF-B antibodies at 25° C. and 37° C.

The equilibrium dissociation constants ($K_D$ values) for human and mouse PDGF-B binding to purified anti-PDGF-B monoclonal antibodies of this disclosure were determined using a real-time surface plasmon resonance (SPR) biosensor instrument, MASS-1. All binding studies were performed in 10 mM HEPES, 300 mM NaCl, 3 mM EDTA, 1 μg/mL Heparin, and 0.05% v/v Surfactant Tween-20, pH 7.4 (HBS-T) running buffer at 25° C. and 37° C. (FIG. 2). The HCA sensor surface was first derivatized by amine coupling the monoclonal mouse anti-human Fc antibody (GE, #BR100839) and anti-PDGF-B monoclonal antibodies were individually captured. Different concentrations of human PDGF-B (hPDGF-B; 50 nM, 12.5 nM, 3.125 nM) or mouse PDGF-B (mPDGF-B; 50 nM, 12.5 nM, 3.125 nM) prepared in HBS-EHT running buffer were injected over the captured anti-PDGF-B monoclonal antibody for 4 minutes at a flow rate of 50 μL/minute, while the dissociation of PDGF-B reagent bound to captured anti-PDGF-B monoclonal antibody was monitored for 10 minutes in HBS-T running buffer. Kinetic association ($k_a$) and dissociation ($k_d$) rate constants were determined by fitting the real-time binding sensorgrams to a 1:1 binding model with mass transport limitation using Scrubber 2.0c software. Binding dissociation equilibrium constant ($K_D$) and dissociative half-life (t½) for different anti-PDGF-B monoclonal antibodies were calculated from the kinetic rate constants as:

$$K_D(M) = \frac{kd}{ka}, \text{ and } t1/2 \text{ (min)} = \frac{\ln(2)}{60 * kd}$$

Binding kinetic parameters for hPDGF-B or mPDGF-B binding to different anti-PDGF-B monoclonal antibodies of this disclosure at 25° C. and 37° C. are shown in Tables 2-4.

TABLE 2

Affinity and $t_{1/2}$ of 17 anti-PDGF-B mAbs - comparison between human and mouse antibodies.

| *-mAbs were sorted based on their monomeric human PDGF BB binding affinities @ 37° C. | | Human | | | | Mouse | | | |
|---|---|---|---|---|---|---|---|---|---|
| | | 25° C. | | 37° C. | | 25° C. | | 37° C. | |
| Ab PID | Strain | $K_D$ (mol/l) | $t_{1/2}$ (min) | $K_D$* (mol/l) | $t_{1/2}$ (min) | $K_D$ (mol/l) | $t_{1/2}$ (min) | $K_D$* (mol/l) | $t_{1/2}$ (min) |
| H4H13127P | | 1.93E−12 | ≥1155 | 1.31E−12 | ≥1155 | NB | NB | NB | NB |
| H4H13145P | | 2.79E−12 | ≥1155 | 1.36E−12 | ≥1155 | 2.30E−12 | ≥1155 | 9.54E−13 | ≥1155 |
| H4H13132P | | 2.26E−12 | ≥1155 | 1.84E−12 | ≥1155 | 1.93E−12 | ≥1155 | 8.67E−11 | ≥1155 |
| H4H13167P | | 5.53E−12 | ≥1155 | 2.75E−12 | ≥1155 | NB | NB | NB | NB |
| H4H13148P | | 7.14E−11 | 12.5 | 8.99E−11 | 17 | 3.60E−10 | 2.8 | 2.43E−10 | 3.0 |
| H4H13169P | | 6.24E−10 | 1.6 | 1.33E−10 | 5 | 5.84E−10 | 2.2 | 2.22E−10 | 3.7 |
| H4H13166P | | 1.59E−10 | 16.9 | 2.24E−10 | 8 | NB | NB | NB | NB |
| H4H13143P | | 1.32E−09 | 0.7 | 2.46E−10 | 3 | 1.24E−09 | 0.8 | 8.61E−11 | 5.0 |
| H4H13163P | | 5.84E−10 | 2.4 | 2.47E−10 | 4 | 7.61E−10 | 2.0 | 1.93E−10 | 4.2 |
| H4H13159P | | 3.10E−10 | 3.6 | 2.62E−10 | 4 | 3.94E−10 | 2.8 | 3.52E−10 | 3.8 |
| H4H13151P | | 1.04E−09 | 1.8 | 2.99E−10 | 3 | 1.22E−09 | 1.3 | 3.35E−10 | 2.4 |
| H4H13157P | | 8.44E−10 | 1.0 | 3.15E−10 | 2 | 2.49E−09 | 6.6 | 6.68E−10 | 1.8 |
| H4H13162P | | 1.21E−10 | 11.5 | 3.20E−10 | 6 | 3.42E−10 | 5.9 | 1.74E−10 | 6.3 |
| H4H13155P | | 1.05E−09 | 1.3 | 4.42E−10 | 2 | 1.85E−09 | 0.7 | 4.04E−10 | 1.3 |
| H4H13170P | | 1.74E−09 | 0.6 | 7.89E−10 | 0.9 | 7.25E−10 | 1.0 | 8.81E−10 | 0.8 |
| H4H13152P | | 2.21E−09 | 0.5 | 1.02E−09 | 0.8 | 1.63E−09 | 0.8 | 5.08E−10 | 0.9 |
| H4H13153P | | NB | NB | NB | NB | NB | NB | NB | NB |
| buffer | | NB | NB | NB | NB | NB | NB | NB | NB |

NB; no binding was observed under the current experimental conditions.

TABLE 3

Binding kinetics of human PDGF BB at 25° C. and 37° C.

| *-mAbs were sorted based on their monomeric human PDGF BB binding affinities @ 37° C. | | 25° C. | | | | | | |
|---|---|---|---|---|---|---|---|---|
| | | α-PDGF BB inAb Captured | | Human PDGF BB - 50 nM Bound | $k_a$ | $k_d$ | $K_D$ | $t_{1/2}$ |
| Ab PID | Strain | (RU) | (SE) | (RU) | (l/mol*s) | (1/s) | (mol/l) | (min) |
| H4H13127P | | 149 | 14 | 49 | 5.19E+06 | ≥1.00E−05 | 1.93E−12 | ≥1155 |
| H4H13145P | | 188 | 7 | 46 | 3.59E+06 | ≥1.00E−05 | 2.79E−12 | ≥1155 |
| H4H13132P | | 217 | 9 | 52 | 4.43E+06 | ≥1.00E−05 | 2.26E−12 | ≥1155 |
| H4H13167P | | 179 | 7 | 51 | 1.81E+06 | ≥1.00E−05 | 5.53E−12 | ≥1155 |
| H4H13148P | | 229 | 2 | 59 | 1.29E+07 | 9.22E−04 | 7.14E−11 | 12.5 |
| H4H13169P | | 130 | 1 | 29 | 1.13E+07 | 7.08E−03 | 6.24E−10 | 1.6 |
| H4H13166P | | 229 | 3 | 61 | 4.30E+06 | 6.82E−04 | 1.59E−10 | 16.9 |
| H4H13143P | | 159 | 1 | 30 | 1.25E+07 | 1.65E−02 | 1.32E−09 | 0.7 |
| H4H13163P | | 158 | 3 | 32 | 8.30E+06 | 4.85E−03 | 5.84E−10 | 2.4 |
| H4H13159P | | 234 | 0.4 | 39 | 1.05E+07 | 3.25E−03 | 3.10E−10 | 3.6 |
| H4H13151P | | 180 | 4 | 40 | 6.33E+06 | 6.56E−03 | 1.04E−09 | 1.8 |
| H4H13157P | | 134 | 3 | 20 | 1.31E+07 | 1.11E−02 | 8.44E−10 | 1.0 |
| H4H13162P | | 135 | 1 | 38 | 8.29E+06 | 1.00E−03 | 1.21E−10 | 11.5 |
| H4H13155P | | 269 | 1 | 50 | 8.61E+06 | 9.01E−03 | 1.05E−09 | 1.3 |

TABLE 3-continued

Binding kinetics of human PDGF BB at 25° C. and 37° C.

| Ab PID | Strain (RU) | (SE) | Bound (RU) | $k_a$ (l/mol*s) | $k_d$ (1/s) | $K_D$ (mol/l) | $t_{1/2}$ (min) |
|---|---|---|---|---|---|---|---|
| H4H13170P | 197 | 1 | 31 | 1.19E+07 | 2.08E−02 | 1.74E−09 | 0.6 |
| H4H13152P | 149 | 4 | 18 | 1.13E+07 | 2.49E−02 | 2.21E−09 | 0.5 |
| H4H13153P | 199 | 1 | 5 | NB | NB | NB | NB |
| buffer | 3 | 0.2 | 4 | NB | NB | NB | NB |

*-mAbs were sorted based on their monomeric human PDGF BB binding affinities @ 37° C.

37° C.

| Ab PID | α-PDGF BB mAb Captured (RU) | (SE) | Human PDGF BB - 50 nM Bound (RU) | $k_a$ (l/mol*s) | $k_d$ (1/s) | $K_D$* (mol/l) | $t_{1/2}$ (min) |
|---|---|---|---|---|---|---|---|
| H4H13127P | 208 | 14 | 62 | 7.65E+06 | ≥1.00E−05 | 1.31E−12 | ≥1155 |
| H4H13145P | 226 | 15 | 58 | 7.35E+06 | ≥1.00E−05 | 1.36E−12 | ≥1155 |
| H4H13132P | 291 | 5 | 70 | 5.45E+06 | ≥1.00E−05 | 1.84E−12 | ≥1155 |
| H4H13167P | 235 | 17 | 70 | 3.63E+06 | ≥1.00E−05 | 2.75E−12 | ≥1155 |
| H4H13148P | 336 | 3 | 83 | 7.70E+06 | 6.92E−04 | 8.99E−11 | 17 |
| H4H13169P | 190 | 3 | 39 | 1.62E+07 | 2.15E−03 | 1.33E−10 | 5 |
| H4H13166P | 318 | 3 | 81 | 6.31E+06 | 1.42E−03 | 2.24E−10 | 8 |
| H4H13143P | 241 | 0.1 | 37 | 1.69E+07 | 4.15E−03 | 2.46E−10 | 3 |
| H4H13163P | 222 | 1 | 38 | 1.07E+07 | 2.65E−03 | 2.47E−10 | 4 |
| H4H13159P | 331 | 0.5 | 61 | 1.04E+07 | 2.71E−03 | 2.62E−10 | 4 |
| H4H13151P | 251 | 1 | 46 | 1.18E+07 | 3.52E−03 | 2.99E−10 | 3 |
| H4H13157P | 199 | 3 | 29 | 2.07E+07 | 6.54E−03 | 3.15E−10 | 2 |
| H4H13162P | 199 | 1 | 50 | 5.83E+06 | 1.86E−03 | 3.20E−10 | 6 |
| H4H13155P | 346 | 0.8 | 56 | 1.07E+07 | 4.72E−03 | 4.42E−10 | 2 |
| H4H13170P | 275 | 0.3 | 38 | 1.68E+07 | 1.33E−02 | 7.89E−10 | 0.9 |
| H4H13152P | 215 | 5 | 25 | 1.44E+07 | 1.47E−02 | 1.02E−09 | 0.8 |
| H4H13153P | 286 | 0.5 | 7 | NB | NB | NB | NB |
| buffer | 10 | 0.3 | 6 | NB | NB | NB | NB |

NB; no binding was observed under the current experimental conditions.

TABLE 4

Binding kinetics of mouse PDGF BB at 25° C. and 37° C.

25° C.

| Ab PID | α-PDGF-B mAb Captured (RU) | (SE) | Mouse PDGF BB - 50 nM Bound (RU) | $k_a$ (l/mol*s) | $k_d$ (1/s) | $K_D$ (mol/l) | $t_{1/2}$ (min) |
|---|---|---|---|---|---|---|---|
| H4H13127P | 140 | 8 | 1 | NB | NB | NB | NB |
| H4H13145P | 167 | 2 | 37 | 4.34E+06 | ≥1.00E−05 | 2.30E−12 | ≥1155 |
| H4H13132P | 206 | 1 | 43 | 5.18E+06 | ≥1.00E−05 | 1.93E−12 | ≥1155 |
| H4H13167P | 182 | 6 | 1 | NB | NB | NB | NB |
| H4H13148P | 252 | 5 | 39 | 1.14E+07 | 4.12E−03 | 3.60E−10 | 2.8 |
| H4H13169P | 132 | 1 | 26 | 9.12E+06 | 5.33E−03 | 5.84E−10 | 2.2 |
| H4H13166P | 238 | 9 | 2 | NB | NB | NB | NB |
| H4H13143P | 156 | 1 | 30 | 1.22E+07 | 1.52E−02 | 1.24E−09 | 0.8 |
| H4H13163P | 155 | 1 | 28 | 7.54E+06 | 5.74E−03 | 7.61E−10 | 2.0 |
| H4H13159P | 235 | 0.5 | 38 | 1.06E+07 | 4.17E−03 | 3.94E−10 | 2.8 |
| H4H13151P | 178 | 4 | 36 | 7.26E+06 | 8.87E−03 | 1.22E−09 | 1.3 |
| H4H13157P | 142 | 4 | 19 | 7.03E+05 | 1.75E−03 | 2.49E−09 | 6.6 |
| H4H13162P | 142 | 6 | 36 | 5.72E+06 | 1.96E−03 | 3.42E−10 | 5.9 |
| H4H13155P | 269 | 0.2 | 38 | 9.20E+06 | 1.70E−02 | 1.85E−09 | 0.7 |
| H4H13170P | 197 | 1 | 31 | 1.65E+07 | 1.20E−02 | 7.25E−10 | 1.0 |
| H4H13152P | 158 | 2 | 15 | 9.17E+06 | 1.49E−02 | 1.63E−09 | 0.8 |
| H4H13153P | 201 | 1 | 2 | NB | NB | NB | NB |
| buffer | 3 | 0.2 | 4 | NB | NB | NB | NB |

TABLE 4-continued

Binding kinetics of mouse PDGF BB at 25° C. and 37° C.

| | | 37° C. | | | | | |
|---|---|---|---|---|---|---|---|
| *-mAbs were sorted based on their monomeric human PDGF BB binding affinities @ 37° C. | | α-PDGF-B mAb Captured | Mouse PDGF BB - 50 nM Bound | $k_a$ | $k_d$ | $K_D$* | $t_{1/2}$ |
| Ab PID | Strain | (RU) | (SE) | (RU) | (l/mol*s) | (1/s) | (mol/l) | (min) |
| H4H13127P | | 201 | 8 | 4 | NB | NB | NB | NB |
| H4H13145P | | 207 | 4 | 46 | 1.05E+07 | ≥1.00E−05 | 9.54E−13 | ≥1155 |
| H4H13132P | | 291 | 3 | 65 | 1.15E+05 | ≥1.00E−05 | 8.67E−11 | ≥1155 |
| H4H13167P | | 221 | 4 | 1 | NB | NB | NB | NB |
| H4H13148P | | 341 | 1 | 57 | 1.57E+07 | 3.82E−03 | 2.43E−10 | 3.0 |
| H4H13169P | | 192 | 2 | 36 | 1.41E+07 | 3.14E−03 | 2.22E−10 | 3.7 |
| H4H13166P | | 320 | 1 | 4 | NB | NB | NB | NB |
| H4H13143P | | 242 | 1 | 38 | 2.68E+07 | 2.31E−03 | 8.61E−11 | 5.0 |
| H4H13163P | | 225 | 2 | 35 | 1.43E+07 | 2.77E−03 | 1.93E−10 | 4.2 |
| H4H13159P | | 331 | 1 | 56 | 8.62E+06 | 3.03E−03 | 3.52E−10 | 3.8 |
| H4H13151P | | 250 | 1 | 41 | 1.41E+07 | 4.72E−03 | 3.35E−10 | 2.4 |
| H4H13157P | | 208 | 2 | 28 | 9.55E+06 | 6.38E−03 | 6.68E−10 | 1.8 |
| H4H13162P | | 201 | 1 | 46 | 1.05E+07 | 1.84E−03 | 1.74E−10 | 6.3 |
| H4H13155P | | 348 | 1 | 44 | 2.13E+07 | 8.61E−03 | 4.04E−10 | 1.3 |
| H4H13170P | | 275 | 0.3 | 33 | 1.65E+07 | 1.45E−02 | 8.81E−10 | 0.8 |
| H4H13152P | | 229 | 4 | 23 | 2.46E+07 | 1.25E−02 | 5.08E−10 | 0.9 |
| H4H13153P | | 290 | 1 | 4 | NB | NB | NB | NB |
| buffer | | 10 | 0.1 | 1 | NB | NB | NB | NB |

NB: no binding was observed under the current experimental conditions.

The binding kinetic parameters for hPDGF-B or mPDGF-B binding to exemplary anti-PDGF-B monoclonal antibodies of this disclosure at 37° C. are shown in Tables 5-6.

TABLE 5

Bia-core Binding Affinity and $t_{1/2}$ at 37° C. for H4H13132P.

| Human PDGF BB - 50 nM Bound 37° C. | | Mouse PDGF BB - 50 nM Bound 37° C. | | Cynomolgus Monkey PDGF-BB - 30 nM Bound 37° C. | |
|---|---|---|---|---|---|
| $K_D$* (mol/l) | $t_{1/2}$ (min) | $K_D$* (mol/l) | $t_{1/2}$ (min) | $K_D$* (mol/l) | $t_{1/2}$ (min) |
| 1.84E−12 | ≥1155 | 8.67E−11 | ≥1155 | 9.67E−12 | 277.2 |

TABLE 6

Bia-core Binding Affinity and $t_{1/2}$ at 37° C. for H4H13145P.

| Human PDGF BB - 50 nM Bound 37° C. | | Mouse PDGF BB - 50 nM Bound 37° C. | | Cynomolgus Monkey PDGF-BB - 30 nM Bound 37° C. | |
|---|---|---|---|---|---|
| $K_D$* (mol/l) | $t_{1/2}$ (min) | $K_D$* (mol/l) | $t_{1/2}$ (min) | $K_D$* (mol/l) | $t_{1/2}$ (min) |
| 1.36E−12 | ≥1155 | 9.54E−13 | ≥1155 | 1.61E−11 | 769.7 |

These binding data demonstrate that anti-PDGF-B-mAbs (e.g., H4H13132P and H4H13145P) can specifically binds to human, cyno monkey, rat and mouse PDGF-BB at pM concentrations.

Example 2. Heavy and Light Chain Variable Region Amino Acid Sequences

Table 7 sets forth the heavy and light chain variable region amino acid sequence pairs of selected antibodies specific for PDGF-B and their corresponding antibody identifiers. Antibodies are typically referred to herein according to the following nomenclature: Fc prefix (e.g. "H4H"), followed by a numerical identifier (e.g., "3132" as shown in Table 7), followed by a "P" suffix. Thus, according to this nomenclature, an antibody may be referred to as, e.g., "H4H13132P". The H4H prefix on the antibody designations used herein indicates the particular Fc region of the antibody. For example, an "H4H" antibody has a human IgG4 Fc.

TABLE 7

| Antibody Designation | SEQ ID NOs: | | | | | | | | |
|---|---|---|---|---|---|---|---|---|---|
| | HCVR | HCDR1 | HCDR2 | HCDR3 | LCVR | LCDR1 | LCDR2 | LCDR3 | HC | LC |
| H4H13145P (REGN13335) | 2 | 4 | 6 | 8 | 10 | 12 | 14 | 16 | 18 | 20 |

TABLE 7-continued

| Antibody | SEQ ID NOs: | | | | | | | | | |
|---|---|---|---|---|---|---|---|---|---|---|
| Designation | HCVR | HCDR1 | HCDR2 | HCDR3 | LCVR | LCDR1 | LCDR2 | LCDR3 | HC | LC |
| H4H13132P (REGN15171) | 22 | 24 | 26 | 28 | 30 | 32 | 34 | 36 | 38 | 40 |

Figure 3A:
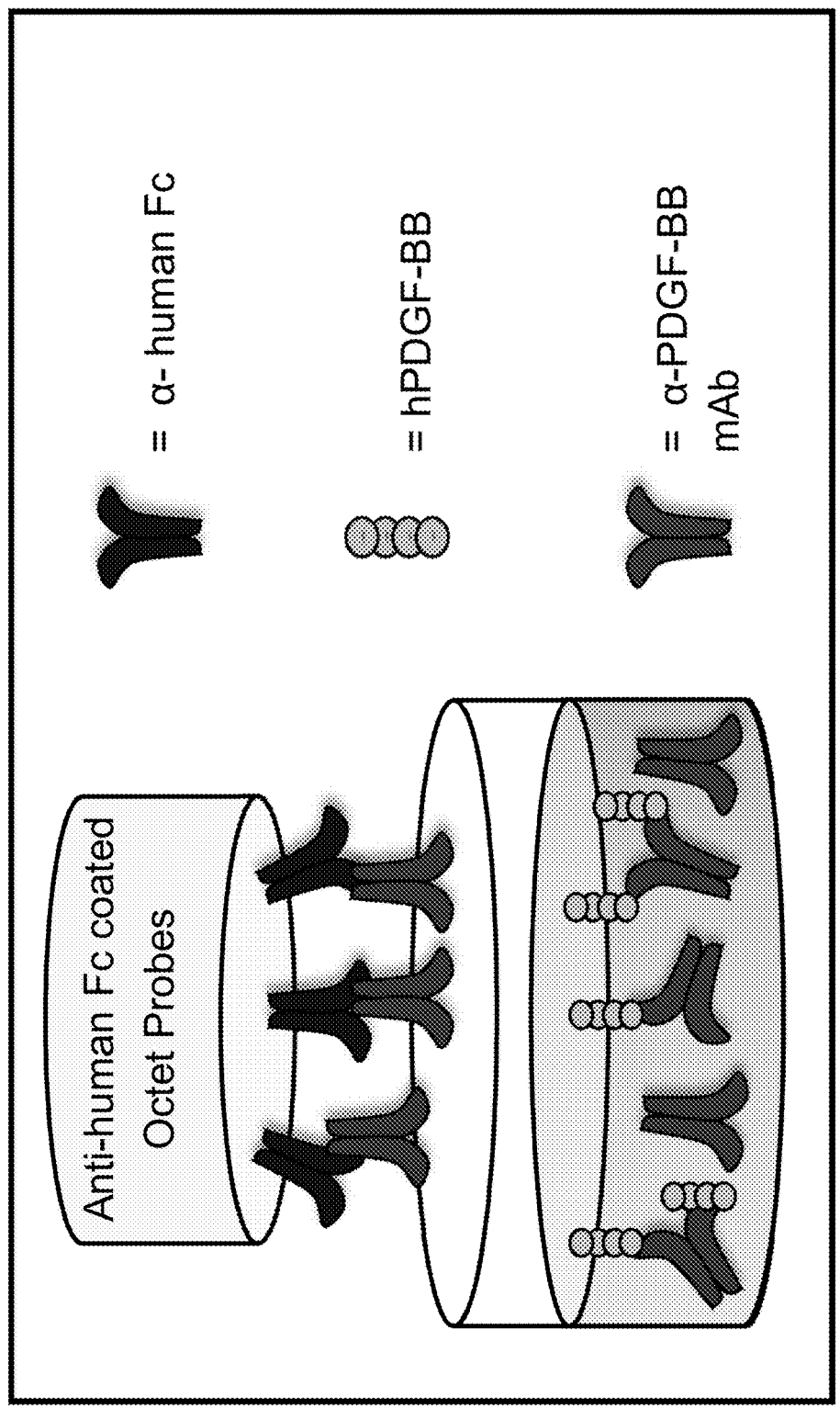
FIG. 3A is a schematic depicting the cross-competition study between purified anti-PDGF-BB monoclonal antibodies.

Example 3. Cross-Competition Between Purified Anti-PDGF-BB Monoclonal Antibodies In order to determine the cross-competition between purified anti-PDGF-BB monoclonal antibodies (mAbs), approximately 1.2-1.6 nM of anti-human PDGF-BB mAbs are captured by dipping α-hFc coated Octet biosensors in wells containing 50 μg/mL of anti-human PDGF-BB mAbs for 3 minutes (FIG. 3A). H4H hFc (iso-type control) were used as negative controls. The unoccupied α-hFc Octet sensors were saturated by dipping in wells containing blocking mAb solution (200 μg/mL of H4H human Fc (iso-type control) 1) for 4 minutes, and 100 nM of human PDGF-BB (R&D) was pre-incubated with 1 uM of anti-PDGF-BB mAbs for at least 2 hours. The blocking mAb saturated Octet biosensors were dipped in wells containing the pre-mix of anti-PDGF-BB mAb and human PDGF-BB for 4 minutes. At the end of each cycle, the α-hFc Octet sensors were regenerated in 10 mM HCl. During the analysis, the self-self background binding signal caused due to the binding to mAb to the capture surface is subtracted from the entire column. The binding response of mAb-1 was compared and the competing and non-competing mAbs were binned based on their respective mAb-1 binding response.

Figure 3B:
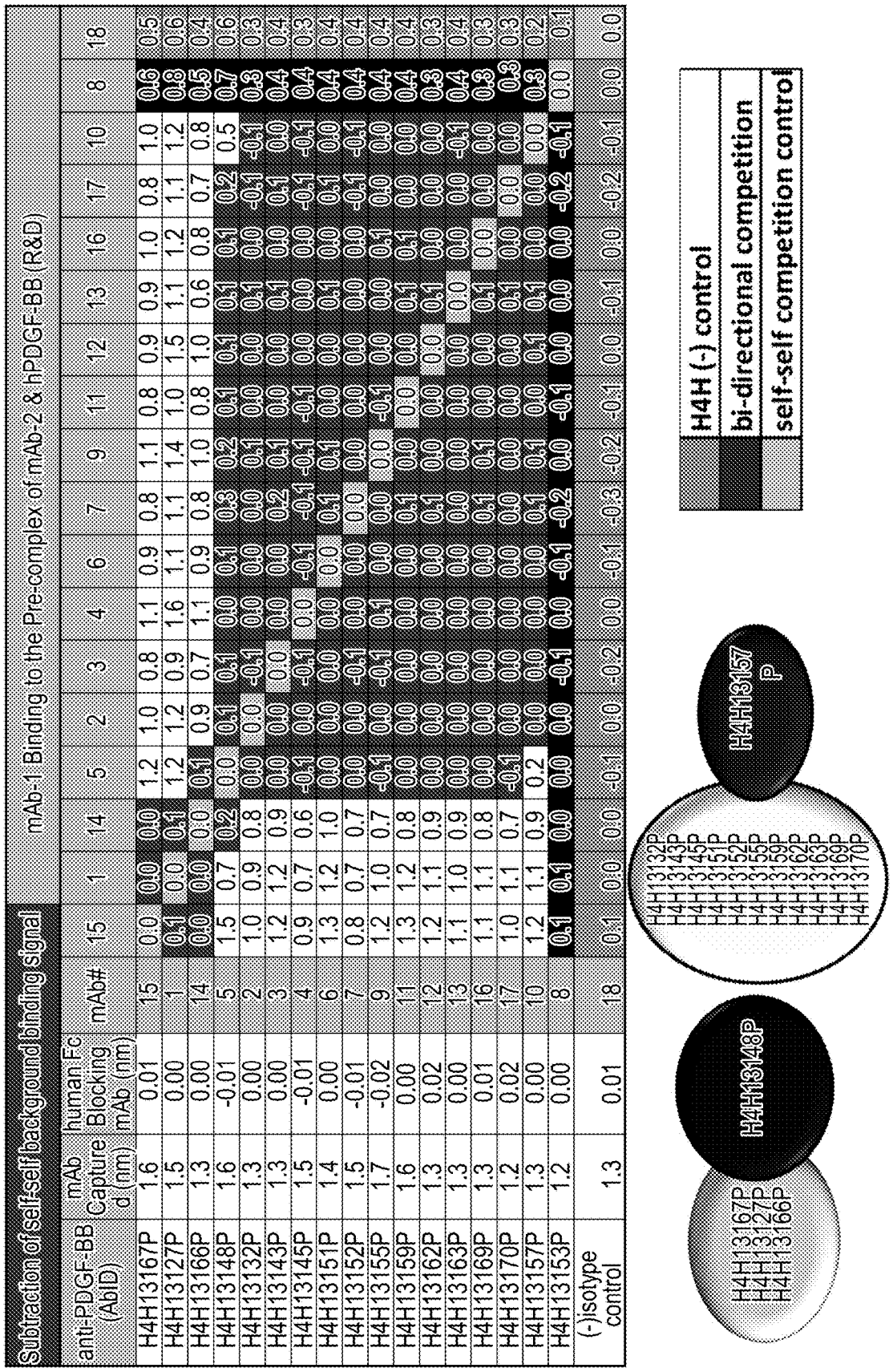
FIG. 3B is a matrix showing the results of an antibody cross-competition assay in which a first anti-PDGF-B antibody (mAb-1) was applied to a human PDGF-BB-coated sensor tip, followed by treatment with a second anti-PDGF-B antibody (mAb-2). Binding responses for each antibody combination tested are depicted.
Figure 4B:
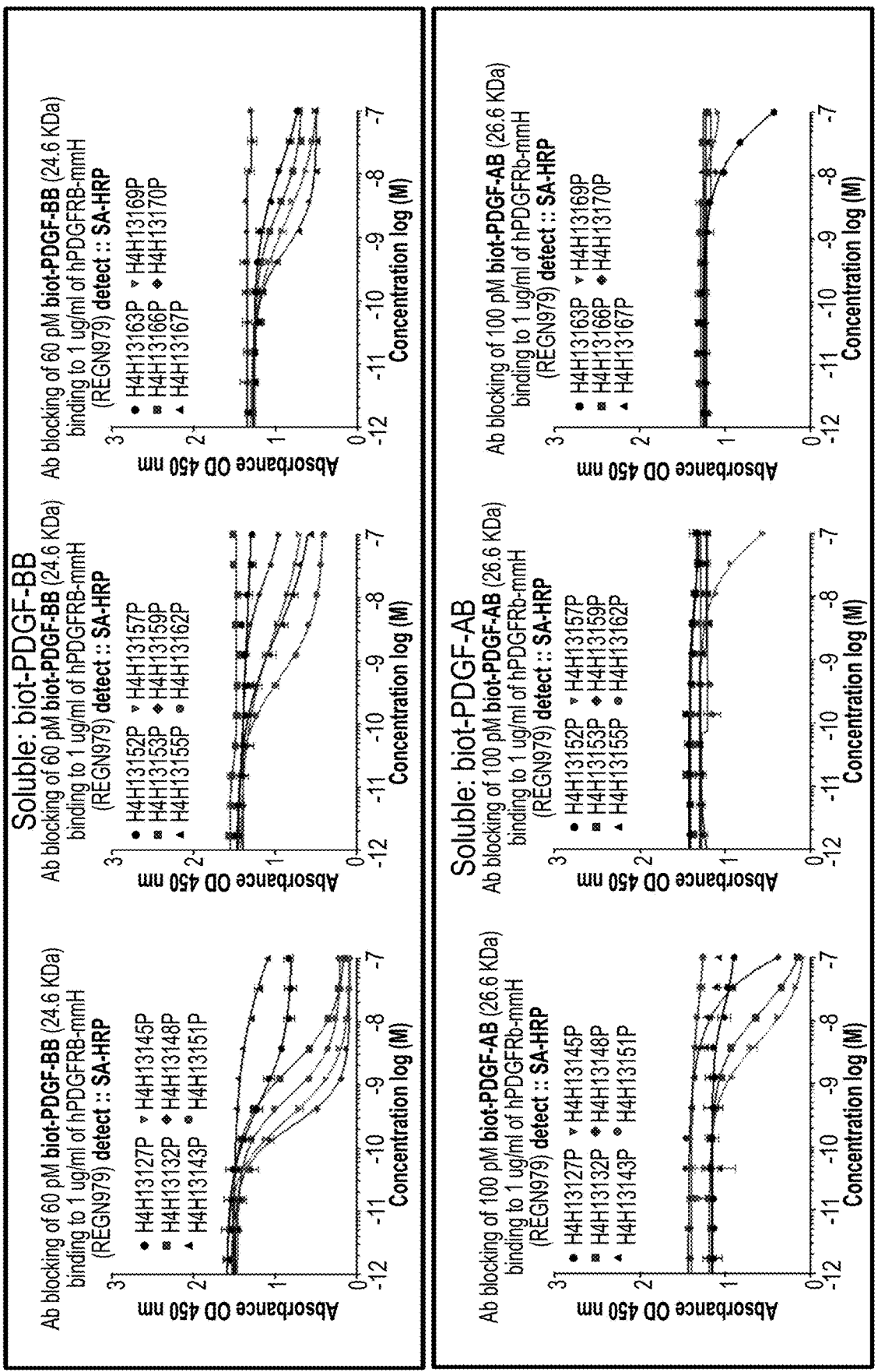

The cross-competition study was performed on the Octet HTX instrument at 25° C., using the running buffer of HBST+0.1 mg/mL BSA. The sensor type was anti-His, the capture flow rate/time was 1000 rpm, for 3 minutes, and the sample inject flow rate/time was 1000 rpm for varied times. FIG. 3B depicts the matrix showing the results of the binding responses of the antibody cross-competition assay. The affinity of the purified antibodies ranges from 0.002 nM to 2 nM.

Example 4. Characterization of Anti-PDGF-B Antibodies by Use of ELISA

The anti-PDGF-B antibodies were characterized in two blocking ELISA formats: blocking PDGF-BB and PDGF-AB binding to plate-captured PDGFR-B. In order to perform the study, 1 ug/ml of human PDGFR-beta-mmH (REGN 979 lot #01-100326) were coated on plates overnight at 4° C.

Pre-bind: 12 point 3 fold serial dilution of Abs from 100 nM+100 pM final conc. biot-PDGF-AB (R&D, 222-AB) or 60 pM final conc. biot-PDGF-BB (R&D, 220-BB). 1 hour at RT. Detect: 1:10,000 SA-HRP.

As depicted in FIGS. 4A-C, 5 strong anti-PDGF-B antibodies were identified which blocked >70%; 3 anti-PDGF-B antibodies blocked both PDGF-BB and PDGF-AB with $IC_{50}$ value ranges for PDGF-BB of 0.23-1.8 nM; 2 anti-PDGF-B antibodies blocked only PDGF-BB with $IC_{50}$ value ranges of 0.55-0.64 nM; 6 moderate anti-PDGF-B antibodies blocked >45%; 2 anti-PDGF-B antibodies blocked both PDGF-BB and PDGF-AB with $IC_{50}$ value ranges for PDGF-BB of 2.8-13 nM; 4 anti-PDGF-B antibodies blocked only PDGF-BB with $IC_{50}$ value ranges of 0.64-2.8 nM; and 6 anti-PDGF-B antibodies were non-blockers.

Example 5. Anti PDGF-B Antibodies Inhibit Human PDGF-BB

In order to determine the activity of the anti PDGF-B antibodies, bioassays were performed using PDGF-BB. For performing the bioassay, 20,000 HEK293/SRE-Luc/hPDGFR3 single cell sorted cells/well were plated in 0.1% FCS Optimem overnight. Dose Response was determined for human PDGF BB (Peprotech, Cat #100-14B, lot #111004, E. coli derived), with 1:3 serial dilutions starting at 100 nM. Inhibition was determined for anti-PDGF-B, anti-PDGFRb (REGN2176, 08-R120731), and purified antibodies (1:3 serial dilution starting at 100 nM) were added to the cells with human PDGF-BB at 500 pM. Plates were incubated for 5.5 hours at 37° C. and luminescence was measured using One-Glo (Promega).

Figure 5A:
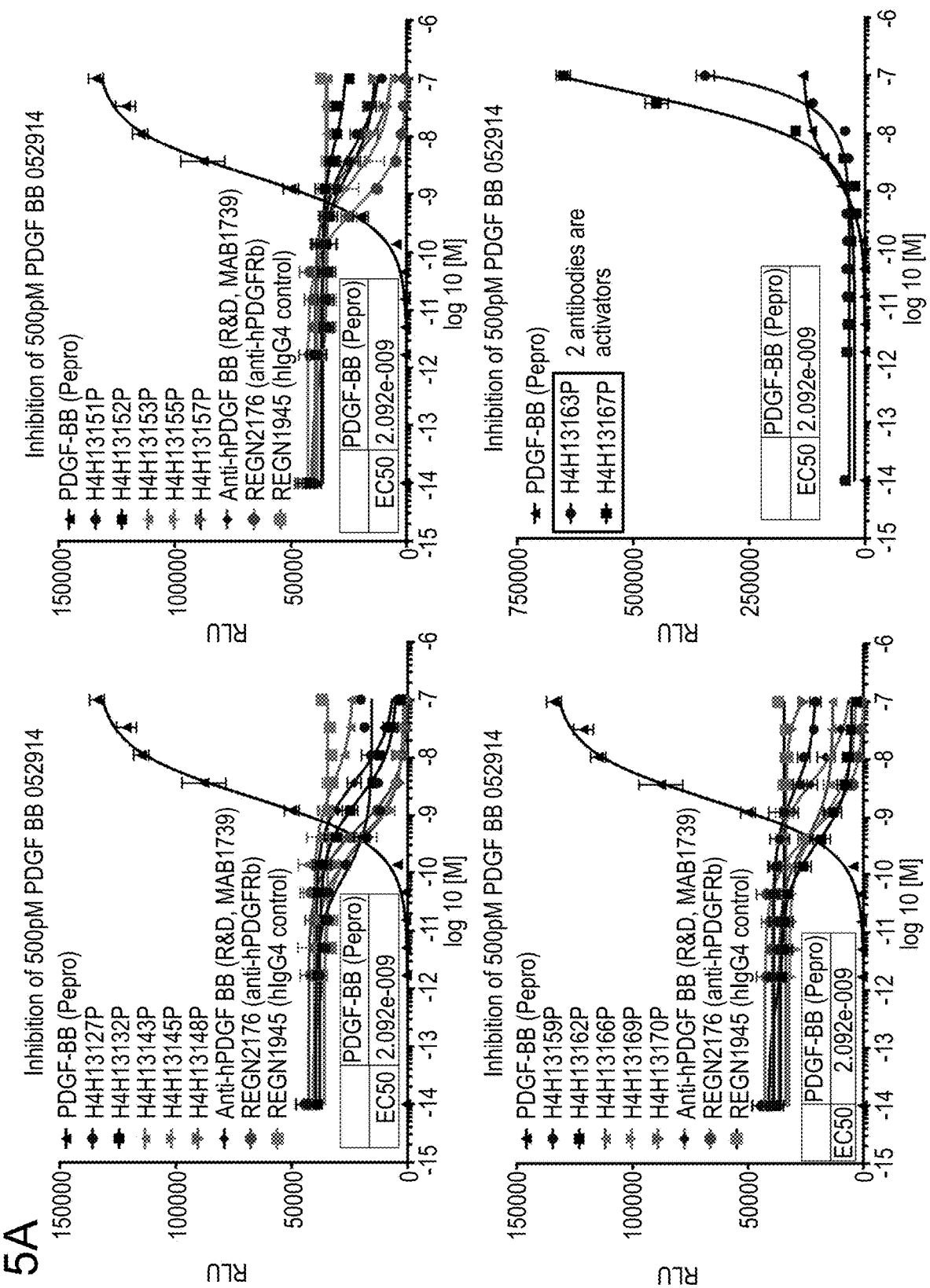
FIG. 5A is a graph depicting that 13 out of 17 anti-hPDGF-B antibodies inhibited 500 pM of hPDGF BB with $IC_{50}$ values of 88 pM-7.2 nM with maximum inhibitions of 42-99%. Further, as depicted in FIG. 5B is a graph depicting that two anti-PDGF-B antibodies activated with human PDGF-BB.
Figure 5C:
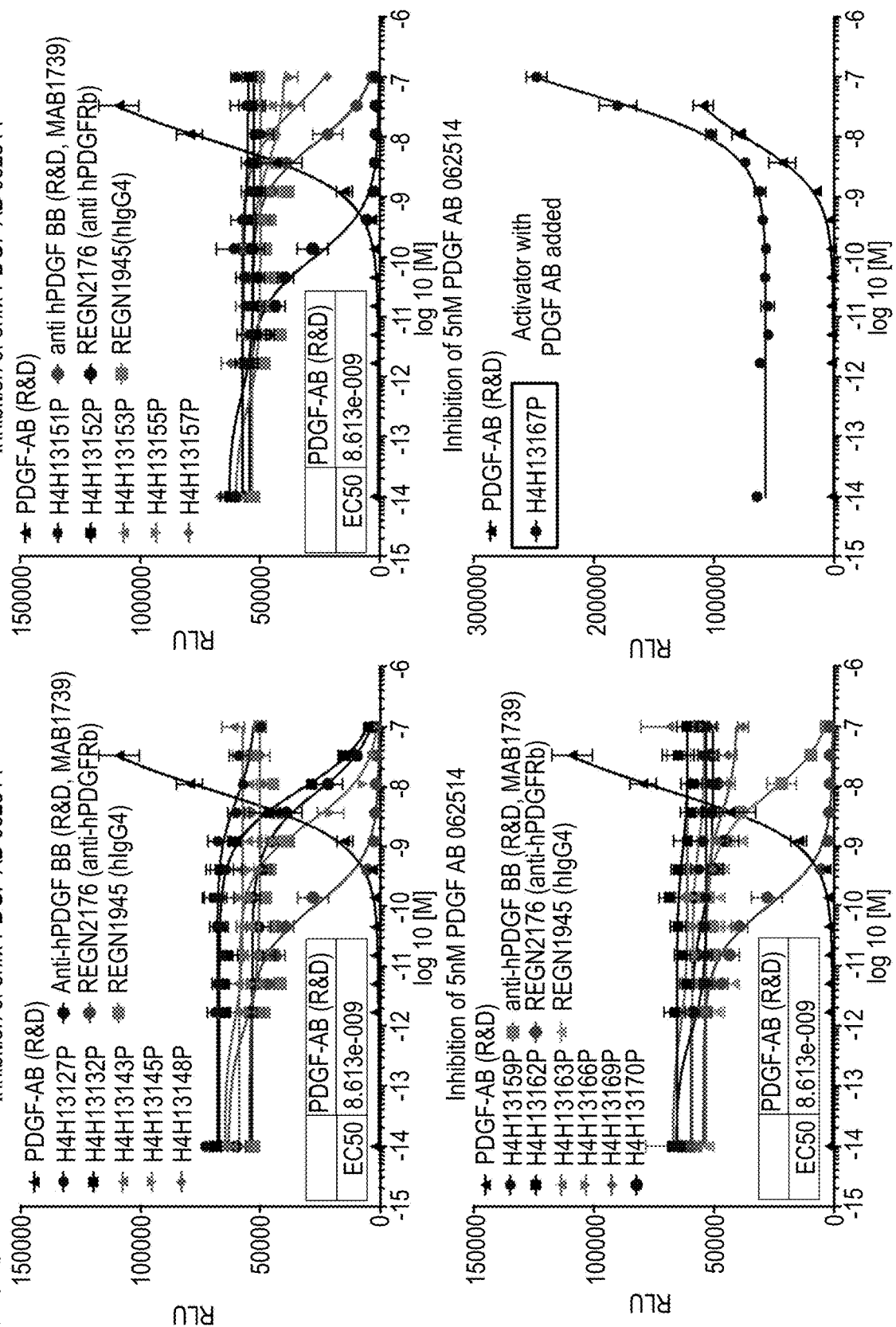
FIG. 5C is a graph depicting that 8 out of 17 anti-hPDGF-B antibodies inhibited 5 nM of human PDGF-AB with $IC_{50}$ values of 99 pM->50 nM with maximum inhibitions of 32-99%. H4H13132P and H4H13145P blocked to baseline with $IC_{50}$ values of 8.8 and 2.6 nM. Lastly.

As depicted in FIG. 5A, 13 out of 17 anti-hPDGF-B antibodies inhibited 500 pM of hPDGF BB with $IC_{50}$ values of 88 pM-7.2 nM with maximum inhibitions of 42-99%. Further, as depicted in FIG. 5B two anti-PDGF-B antibodies activated with human PDGF-BB. FIG. 5C depicts the 8 out of 17 anti-hPDGF-B antibodies which inhibited 5 nM of human PDGF-AB with $IC_{50}$ values of 99 pM->50 nM with maximum inhibitions of 32-99%. H4H13132P and H4H13145P blocked to baseline with $IC_{50}$ values of 8.8 and 2.6 nM. Lastly, FIG. 5D depicts the 10 out of 17 anti-hPDGF-B antibodies, which inhibited 600 pM of mouse PDGF-BB with $IC_{50}$ values of 450 pM-6.4 nM with maximum inhibitions of 39-98%. These results demonstrate that 6 anti-PDGF-B antibodies exhibit full inhibition of human PDGF-BB with $IC_{50}$ values of 310 pM-2 nM. In particular, H4H131.45P inhibits all 3 ligands, hPDGF BB, hPDGF AB, and mPDGF BB, to baseline. The inhibition of PDGF-B activation by use of exemplary anti-hPDGF-B antibodies in HEK293/SRE-ludhPDGFRβ cells are summarized in Tables 8-9 below.

TABLE 8

Inhibition of PDGF-B activation by H4H13132P in HEK293/SRE-luc/hPDGFRβ cells

| Human PDGF-BB EC50 - 2.1E–09 500 pM hPDGF BB | | Human PDGF-AB EC50 - 8.6E–09 5 nM hPDGFAB | | Mouse PDGF-BB EC50 - 9.3E–10 600 pM mPDGFBB | | Monkey PDGF-BB EC50 - 6.4E–11 500 pM mfPDGFBB | |
|---|---|---|---|---|---|---|---|
| IC50 | (%) Inhibition | IC50 | (%) Inhibition | IC50 | (%) Inhibition | IC51 | (%) Inhibition |
| 1.9E–9 | 94 | 8.8E–09 | 95 | 1.5E–9 | 87 | 8.9E–9 | 98.5 |

H4H13132P exhibits greater than 87% inhibition with $IC_{50}$ values of 1.9-9.0 nM against hPDGF-BB, hPDGF-AB, mPDGF-BB, and cynoPDGF-BB.

TABLE 9

Inhibition of PDGF-B activation by H4H13145P in HEK293/SRE-luc/hPDGFRβ cells

| Human PDGF-BB EC50 - 2.1E–09 500 pM hPDGF BB | | Human PDGF-AB EC50 - 8.6E–09 5 nM hPDGFAB | | Mouse PDGF-BB EC50 - 9.3E–10 600 pM mPDGFBB | | Monkey PDGF-BB EC50 - 6.4E–11 500 pM mfPDGFBB | |
|---|---|---|---|---|---|---|---|
| IC50 | (%) Inhibition | IC50 | (%) Inhibition | IC50 | (%) Inhibition | IC51 | (%) Inhibition |
| 4.6E–10 | 99 | 2.6E–09 | 99 | 4.5E–10 | 98 | 3.2E–10 | 99 |

H4H13145P exhibits complete inhibition with $IC_{50}$ values of 0.5-3 nM against hPDGF-BB, hPDGF-AB, mPDGF-BB, and cynoPDGF-BB.

Example 6. Analysis of Complexes Formed Between Recombinant Human PDGF-BB and Anti-PDGF-B Monoclonal Antibodies (mAbs)

Size exclusion chromatography coupled to multi-angle laser light scattering (SEC-MALLS) was used to assess the relative size distribution of complexes formed between recombinant human PDGF-BB (Peprotech) and several anti-PDGF lead mAbs. Five mM PDGF-BB+ 5 mM mAb (Equimolar Ratios) were prepared in 1×PBS, pH 7.4 for each anti-PDGF-B mAb tested and allowed to incubated at room temperature for 3 hour prior to fractionation of total protein by SEC-MALLS. Under the SEC-MALLS conditions, 100 mg (total protein) of each sample was injected in duplicate onto a GE Healthcare Superose 6 10/300 GL column in 1λ PBS, pH 7.4 (mobile phase) with a run time of 90 minutes per injection.

Figure 6A:
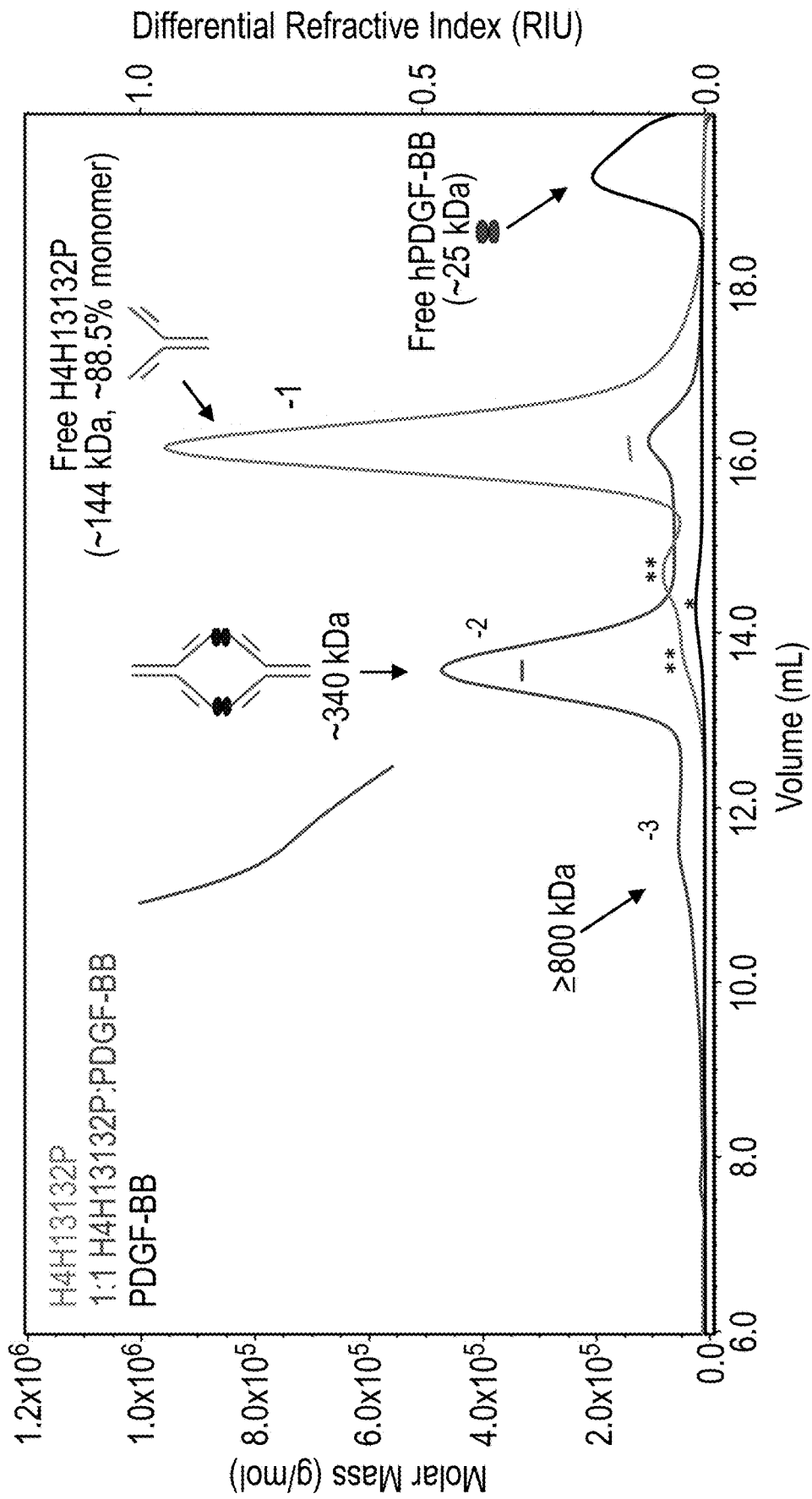
FIGS. 6A, 6B and 6C are graphs depicting the chromatograms from samples forming the most distinct 2:2 mAb:human-PDGF-BB species with no detectable higher order complexes observed.
Figure 6B:
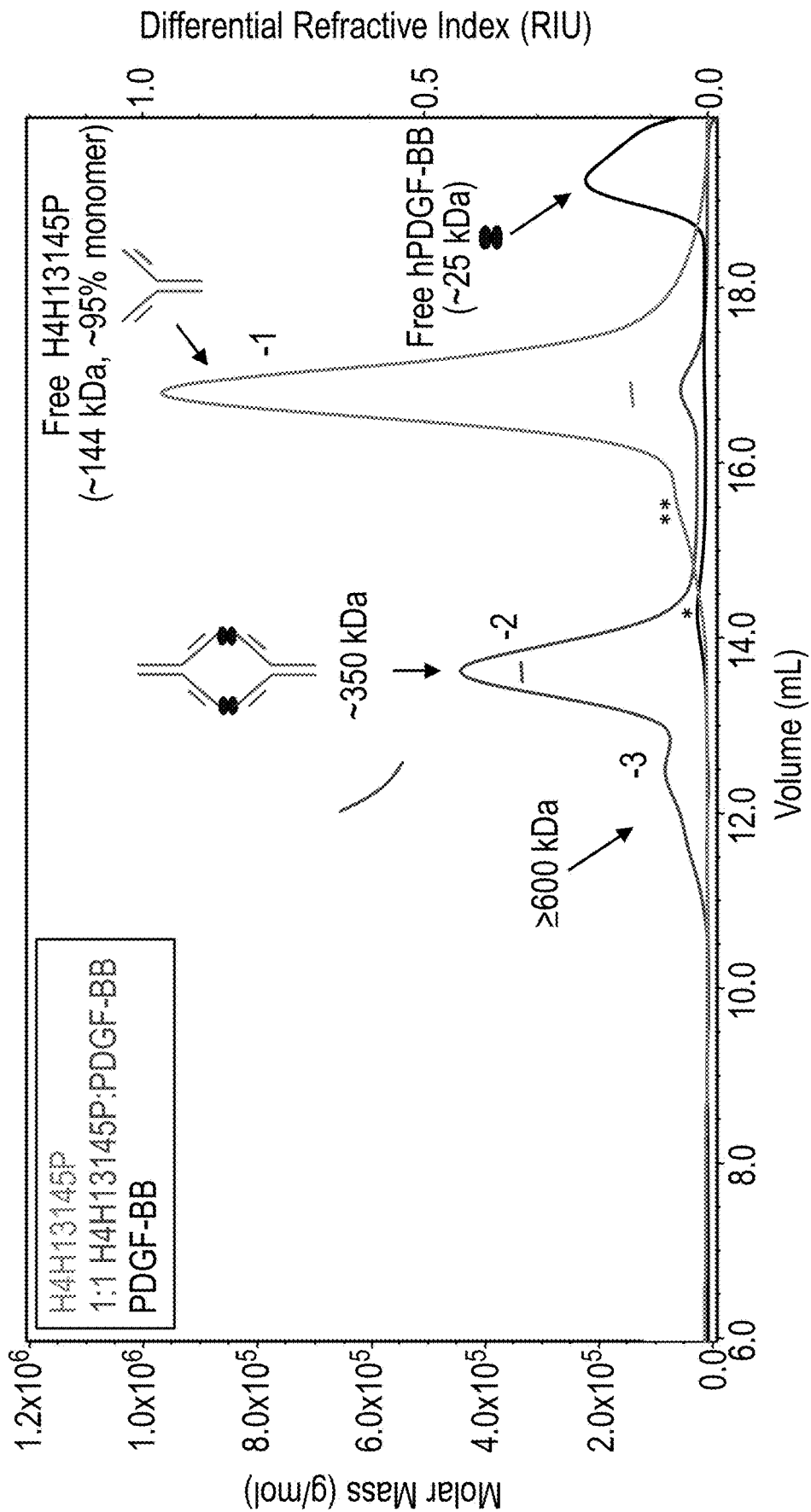
Figure 6C:
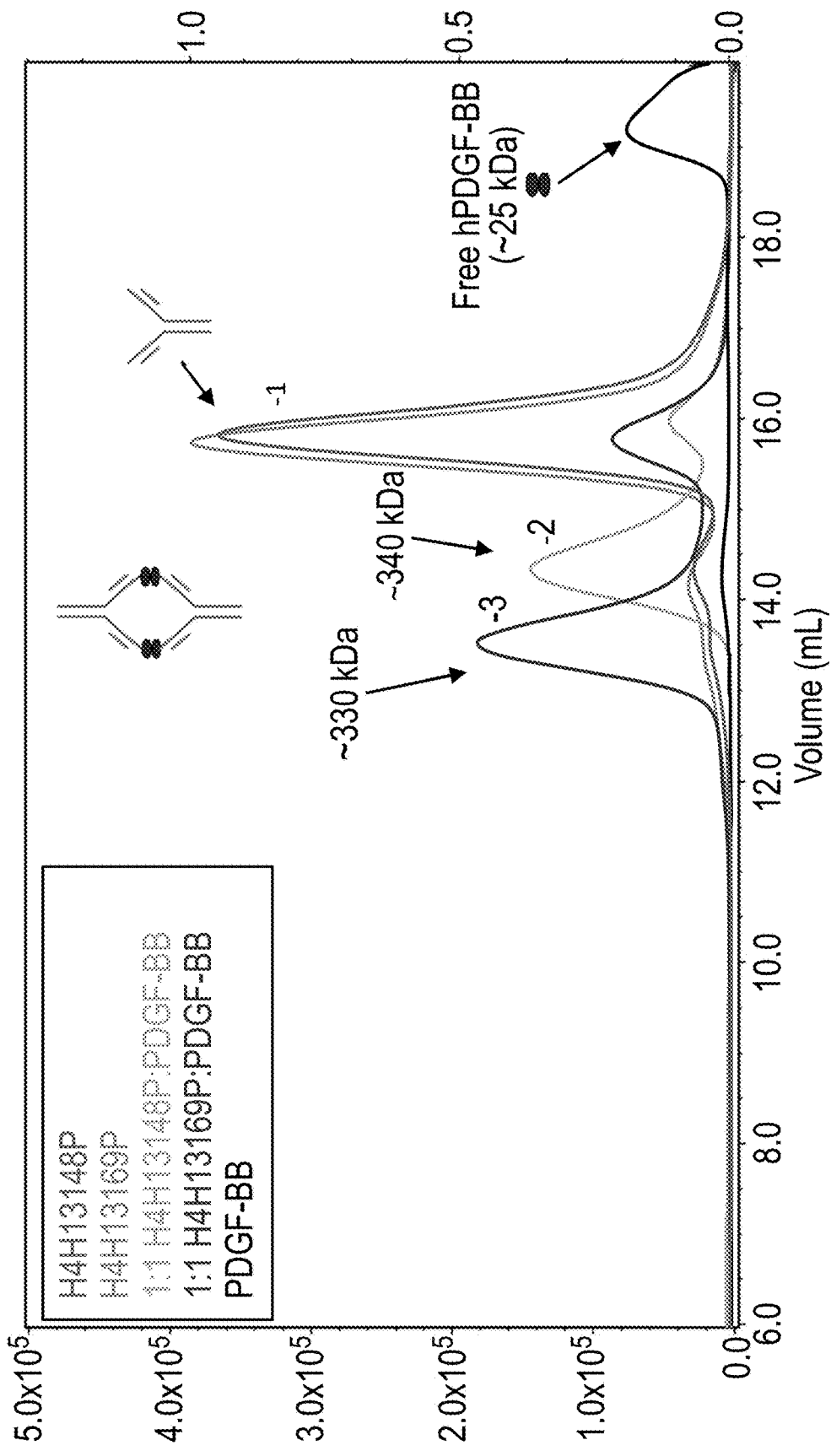

H4H13145P (Peak 1) largely formed a distinct complex (Peak 2) with human PDGF-BB consistent with a 2:2 mAb:human-PDGF-BB species (FIG. 6A). Further, H4H13145P (Peak 1) largely formed a distinct complex (Peak 2) with human PDGF-BB Consistent with a 2:2 mAb:human-PDGF-BB species (FIG. 6B). FIG. 6C depicts the overlaid chromatograms from samples forming the most distinct 2:2 mAb:human-PDGF-BB species with no detectable higher order complexes observed.

In general, most anti-PDGF mAbs appeared to form a largely distinct complex with human PDGF-BB, consistent with a 2:2 mAb:hPDGF-BB species, with little to no higher order complexes ("paper doll") observed. A minor amount of higher order complexes larger than a 2:2 mAb:hPDGF-BB species was observed in samples H4H13132P, H4H13145P, and H4H13162P; however it is unclear whether these complexes formed as a result of the interaction of hPDGF-BB with the monomeric form of the antibody or with antibody multimers (HMW species) that were present at varying amounts in each mAb sample. Alternatively, the higher order complexes in these sample may be due to interaction of the monomeric antibody with a minor amount of multimeric hPDGF-BB, which was also detected. Samples H4H13148P and H4H13169P appeared to form the most distinct 2:2 mAb:hPDGF-BB species with no detectable higher order complexes present. Interestingly, although the complexes formed by these two samples had similar calculated molar masses, the complexes formed by H4H13148P eluted significantly later than the equivalent H4H13169P complexes suggesting that the molecular shape (hydrodynamic radius) of the complexes formed by H4H13148P is more compact in nature. A broad distribution of complexes<the putative molar mass of a 2:2 mAb: hPDGF-BB complex was observed in the H4H13155P sample which may indicate that the complexes formed with hPDGF-BB in solution were dissociating during the fractionation process or that the sample did not reach equilibrium under the experimental conditions tested.

Figure 7:
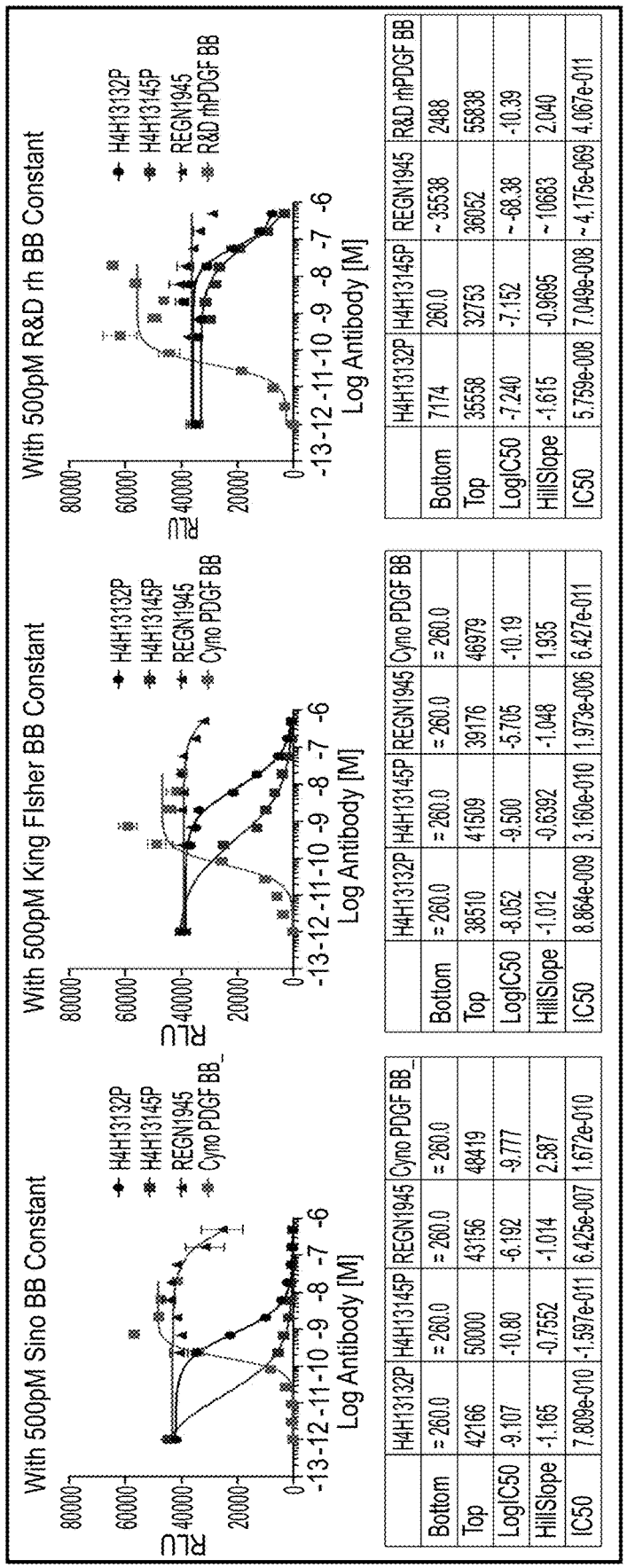
FIG. 7 is a graph depicting that H4H13145P is more potent than H4H13132P against both human and cynomolgus PDGF-BB proteins.

Example 7. Cynomolgus PDGF-BB Protein Bioassay Validation of Anti-PDGF-B Monoclonal Antibodies—H4H13132P and H4H13145P Cynomolgus monkey PDGF-BB was obtained from KingFisher and Sino Biological as Fc-fusion. HEK293/SRE-Luc/mfPDGFBB-ecto/hPDGFRb-cyto cells p2 were seeded onto 96 well plates, and the cells were added at 80 ul/well of the $2.5 \times 10^5$ cells/ml (20,000 cells/well) overnight at 37° C., 5% $CO_2$. Dose response of PDGF-BBs, was determined at 1 to 3 dilutions starting from 20 nM. For determining the inhibition, 1:3 serially diluted Abs were analyzed, starting from 500 nM with 500 pM PDGF-BB as constant. The plates were incubated at 37° C., 5% $CO_2$ for 5.5 hours. The plates were removed from the incubator and equilibrated at room temperature (RT) for approximately 30 minutes. 100 ul of One-glo substrate (equilibrated to RT) was added to all wells of the plates, and mixed on plate shaker at RT for 10 minutes. Luminescence was measured by using the SpectraMaxi3X (PerkinElmer™). As depicted in FIG. 7, in this assay system, H4H13145P was identified to be more potent than H4H13132P against both human and cynomolgus PDGF-BB proteins.

The following assays were used to determine the potency of anti-PDGF-B antibodies to block cynomolgus PDGF-BB induced signaling in cells with expression of the extracellular domain of monkey PDGFRβ.

Luciferase Bioassay

The engineered cell line, HEK293/SRE-Luc/mfPDGFRβ-ecto/hPDGFRb-cyto cells (ACL7804) was used to assay the ability of H4H13145P and H4H13132P to neutralize luciferase expression driven by cynomolgus PDGF-BB. Cells were seeded into 96 well plates using assay medium (0.5% bovine serum albumin, 1% penicillin-streptomycin-glutamine in DMEM media) and serum starved overnight (37° C., 5.0% $CO_2$).

Generation of Dose Response Curves

A dose response curve for cynomolgus PDGF-BB was determined by adding the ligand diluted in assay medium to the HEK293/SRE-Luc/mfPDGFRβ-ecto/hPDGFRb-cyto cells at concentrations ranging from 3 pM to 20 nM. Each concentration was tested in duplicate and wells with no ligand added served as negative controls. Following addition of cynomolgus PDGF-BB, cells were incubated for 5.5 hours at 37° C., 5.0% $CO_2$ and then equilibrated to room temperature for 30 minutes. An equal volume of ONE-Glo luciferase substrate was added to each well and the plate was incubated at room temperature for an additional 5 minutes. Relative light units (RLU) were measured on a SpectraMaxi3X plate reader and the values were analyzed by a four-parameter logistic equation over a 10-point dose response curve (GraphPad Prism).

Generation of Inhibition Curves

H4H13145P and H4H13132P were tested for inhibition of cynomolgus PDGF-BB mediated mfPDGFRβ signaling in the HEK293/SRE-Luc/mfPDGFRβ-ecto/hPDGFRb-cyto cell line. H4H13145P, H4H13132P, or negative control antibody (REGN1945) was added in duplicate to cells at concentrations ranging from 228 pM to 500 nM followed by the addition cynomolgus PDGF-BB at 500 pM. Plates were incubated at 37° C., 5.0% $CO_2$ for 5.5 hours and equilibrated to room temperature for 30 minutes. An equal volume of ONE-Glo luciferase substrate was added to each well and the plate was incubated at room temperature for a further 5 minutes. Relative light units (RLU) were measured on a SpectraMaxi3X plate reader and the values were analyzed by a four-parameter logistic equation over a 10-point dose response curve (GraphPad Prism).

Results

Blockade of Ligand Mediated Cynomolgus PDGF-BB Mediated mfPDGFRβ Signaling

The concentrations of Sino Biologics cynomolgus PDGF-BB Fc tag required to stimulate mfPDGFRβ signaling to 50% of the maximum activity level (the $EC_{50}$) in the HEK293/SRE-Luc/mfPDGFRβ-ecto/hPDGFRb-cyto cell line was 167 pM (FIG. 7) The concentration of antibody required to reduce PDGF-BB signaling to 50% of maximal activity (the $IC_{50}$) in the presence of a fixed concentration of cynomolgus PDGF-BB was determined for H4H13132P, H4h13145P, and an isotype control antibody, REGN1945 (an antibody raised against feline Fel d 1, with no binding to mfPDGFRβ). As shown in FIG. 7, H4H13132P and H4H13145P effectively blocked cynomolgus PDGF-BB signaling induced by a fixed concentration of 500 pM cynomolgus PDGF-BB with an $IC_{50}$ value of 781 pM and 16 pM, respectively. In contrast, the IgG4 isotype control antibody, REGN1945, was ineffective at blocking cynomolgus PDGF-BB signaling induced by cynomolgus PDGF-BB.

Example 8. Biacore Binding Validation of Commercial Monkey PDGF-BB Reagents to Anti-PDGF-B Monoclonal Antibodies—H4H13132P and H4H13145P In order to determine the binding kinetics of commercial monkey PDGF-BB (Kingfisher, Sino biological) to anti-PDGF-B mAbs H4H13132P and H4H13145P, approximately 250-350 RU of anti-PDGF-B mAbs were captured with negative control (REGN1945) on an anti-hFc HCA Chip for the MASS-2 at 25° C. 90 nM of human and monkey PDGF-BB were prepared, and serially diluted 3-fold. The sample was injected at 25 uL/minute for 3 minutes and the dissociation was monitored for 10 minutes. The kinetics parameters were evaluated by fitting the real time data using 1:1 binding model with mass transport limitation. As depicted in FIG. 8, commercial Monkey PDGF-BB showed specific binding to the anti-PDGF-B mAbs H4H13132P and H4H13145P.

Example 9. Western Blot Detection of mAb Binding Epitopes on PDGF-BB

A key to understanding the varying performance of antibodies is to determine the binding sites, or epitopes, they recognize. Epitopes are generally divided in two categories, linear epitopes, where a stretch of continuous amino acids are sufficient for binding and conformational epitopes where key amino acid residues are brought together by protein folding. Linear epitopes might be preferred for applications in which the protein target is wholly or partially denatured during the sample preparation prior to the immuno assay, such as in Western blot (WB). Accordingly, Western blot analysis of PDGF-BB with H4H13145P and H4H13132P was performed to determine if these mAbs bind to linear epitopes.

Human recombinant PDGF-BB dimer protein (CF) from R&D system 1 µg was resolved with SDS PAGE 5-20% gradient gel under reducing (R) and non-reducing (NR) conditions. The following steps were used for detecting PDGF-BB bands in both R and NR condition with PDGF-BB mAb H4H13145P and commercial anti-PDGF-BB ab (R&D anti-human PDGF-BB ab: Human PDGF-BB Antibody AF-220-NA). For non-specific blocking: PVDF membranes were blocked in 5% BSA, for 1 hour at room temperature. For primary Ab blotting: the PVDF membrane (1) PDGF-BB mAb H4H13145P or (2) R&D anti-PDGF-BB mAb at 1.0 ug/ml dilution in 5% BSA TBST overnight at 4 C. The membrane was washed in TBST washing buffer for 10 minutes (three times) at room temperature. Secondary antibody incubation comprised incubating the membrane in HRP-conjugated anti-mouse secondary Ab in 5% BSA TBST, for 1 hour at room temperature. Membrane washing comprised use of TBST buffer for 10 minutes (three times) at room temperature. The signal was developed with Pierce™ Western Blot Signal Enhancer.

Figure 9:
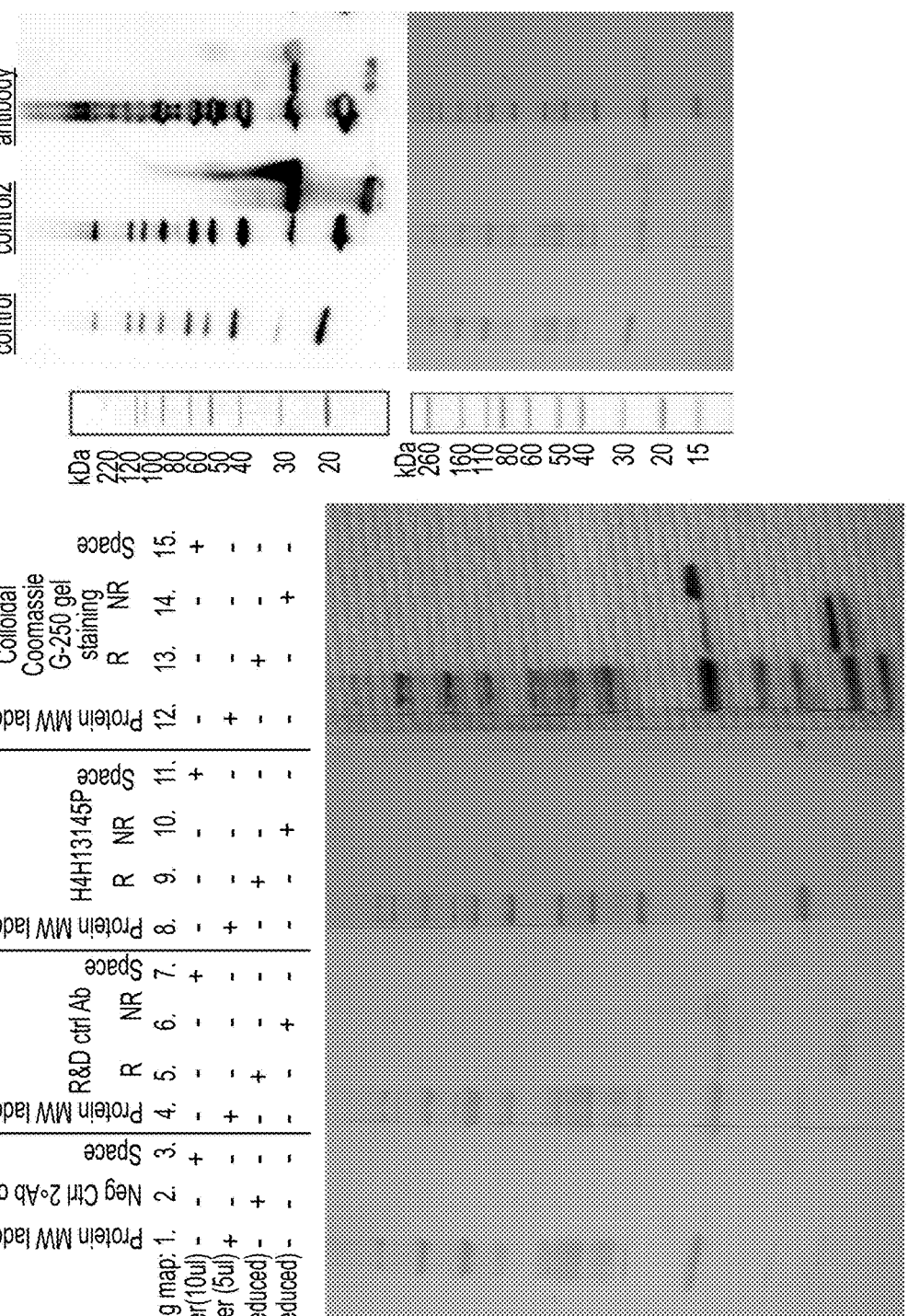
FIG. 9 depicts a western blot analysis of antibody binding epitopes, which confirmed that H4H13145P binds to linear epitopes of human rPDGF-BB.

One µg/lane of Recombinant Human PDGF-BB was resolved with SDS-PAGE under reducing (R) and non-reducing (NR) conditions and visualized by silver staining, showing single bands at 13 kDa and 28 kDa, respectively. FIG. 9 depicts that the western blot analysis of antibody binding epitopes confirmed that H4H13145P binds to linear epitopes of human rPDGF-BB.

Example 10. Pre-Clinical Experimental PAH Efficacy Assessment of H4H13145P

PDGF-B blockade via lead mAb (H4H13145P) provided robust therapeutic benefit in multiple models of PAH (mouse+rat). These effects were more impressive than any treatments or benchmark to date including SOC. These results demonstrate that an anti-PDGF-B antibody would provide an effective non-vasodilator PAH therapy.

To evaluate the effect of the anti-PDGF-B antibody, H4H13145P, in pulmonary arterial hypertension, separate studies were performed using a chronic hypoxia-induced pulmonary arterial hypertension mouse model and a monocrotaline rat model.

The PAH models are summarized in Table 10 below.

TABLE 10

PAH Preclinical Models

| Model | Species | Induction | Mechanism of action | Human Relevance | Limitations |
|---|---|---|---|---|---|
| Hypoxia/ Sugen5416 | Mouse | 4-8 weeks continuous exposure to 10% $O_2$ with weekly Sugen s.c. injection | Hypoxia s VEGFR2 inhibition Selection of apoptotic resistant endothelial cells | Relevant to hypoxia in humans Moderate pulmonary blood pressure change Observed vessel pruning phenotype | Compensatory right heart hypertrophy No plexiform lesions No media vessel wall thickening |
| MCT | Rat | 4-6 weeks, (single subQ injection of MCT (40-60 mg/kg) | Metabolite injures endothelium, Mechanism is unclear | ↑Right heart pressure Right heart hypertrophy (Fulton's Index) Progressive PAH and heart failure Intimal hyperplasia, medial hypertrophy, and adventitial thickening | MCT syndrome consisting of pulmonary interstitial edema, myocarditis, and hepatic veno-oclusive disease that is uncharacteristic of severe human PAH; Death from cardiac or renal dysfunction; |
| Hypoxia/ Sugen5416* | Rat | 3 weeks continuous exposure to 10% $O_2$ with weekly Sugen injection → 3 weeks normoxic condition | Same as in Hypoxia/Sugen mice | Progressive to right heart failure Predictably severe PAH caused by angio-obliterative lesions Intimal hyperplasia, medial hypertrophy, and adventitial thickening | Sugen inhibits other RTKs: PDGFRb, c-KIT, MET, FLT3 and RET |

The following materials and methods were used for these studies.

Materials and Methods
Mice

Pulmonary arterial hypertension (PAH) is characterized by pulmonary vascular remodeling that leads to a progressive increase in vascular resistance. Elevated pulmonary pressures induce compensatory right ventricular hypertrophy and eventual failure. Platelet-derived growth factor-B (PDGF-B) is a potent mitogen that is a member of the platelet-derived growth factor (PDGF) family. PDGF-B/PDGFRβ signaling has been shown to be a central signaling pathway regulating pathologic pulmonary arterial vessel remodeling. This study is to compare efficacy of anti-PDGF-B and anti-PDGFRβ antibodies in hypoxia/sugen PAH mice when dosed therapeutically.

For the first study, 14 to 16 weeks old male humanized PDGFRβ$^{hu-hu}$ mice, (MAID #1639) were used. Mice were separated into treatment groups by weight such that starting body weights were similar among different groups. Cages were selected to either remain at ~21% $O_2$ (normobaric normoxia) or placed into 10% $O_2$ (normobaric hypoxia) chamber (a modified 6' Semi-Rigid Isolator unit, Charles River) that maintained low $O_2$ levels with adjustment of $N_2$ flow to a steady intake of room air. Mice in hypoxia chamber were given VEGF receptor inhibitor Sugen5146 at 20 mg/kg subcutaneously once a week for 6 weeks. The mice were administered antibodies starting on day 21 for 3 weeks as outlined in Table 11. By the end of week 6, right ventricular systolic pressure (RVSP) was measured by right heart catheterization and RV hypertrophy was calculated by Fulton index as the weight ratio of RV and (LV+septum).

For the second study (Study 2), 12 to 14 weeks old male C57/BL mice, (Taconic) were used for the studies. Mice were separated into treatment groups by weight such that starting body weights were similar among different groups. Cages were selected to either remain at ~21% $O_2$ (normobaric normoxia) or placed into 10% $O_2$ (normobaric hypoxia) chamber (a modified 6' Semi-Rigid Isolator unit, Charles River) that maintained low $O_2$ levels with adjustment of $N_2$ flow to a steady intake of room air. Mice in hypoxia chamber were given VEGF receptor inhibitor Sugen5146 at 20 mg/kg subcutaneously once a week for 6 weeks. The mice were administered antibodies starting on day 21 for 3 weeks as outlined in Table 12. By the end of week 6, right ventricular systolic pressure (RVSP) was measured by right heart catheterization and RV hypertrophy was calculated by Fulton index as the weight ratio of RV and (LV+septum). Mice serum were collected at day 42 for human antibody IgG assessment.

Right Heart Catheterization and Right Ventricular Systolic Pressure

Mice were anesthetized with isoflurane and were kept at approximately 37° C. using a heated platform (Heated Hard Pad 1, Braintree Scientific) and circulating heated water pump (T/Pump Classic, Gaymar Industries). The neck area for each mouse was prepared for surgery by depilating over the right common Carotid artery and right Jugular vein. An incision was made, and the right Jugular vein was isolated with care as to not damage the Carotid artery and/or the Vagus nerve. A piece of 5-0 silk suture was placed under the isolated Jugular vein to allow for retraction of the vessel cranially, then a 30-guage needle was used to introduce a hole into the Jugular vein. A pressure catheter (Micro-tip catheter transducer SPR-1000, Millar Instruments, Inc.) was inserted into the opening of the Jugular vein and advanced past the right atrium into the right ventricle. The catheter was connected to pressure/volume instrument (MPVS-300, Millar Instruments, Inc.) that measured heart rate as well as both diastolic and systolic right ventricular pressures. These parameters were digitally acquired using a data acquisition system (PowerLab 4/35, AD Instruments). LabChart Pro 7.0 software (AD Instruments) was used to analyze right ventricular pressures. Readings were quantified from a 60 second interval of the pressure tracing (following a 2 minute period of recording to allow for pressure stabilization). The parameters analyzed were right ventricular systolic pressures (RVSP), heart rate (HR) and rate of right ventricular pressure rise (dP/dt max).

Right Heart Hypertrophy Assessment

After the in vivo hemodynamic measurements, animals were euthanized by exsanguinations under anesthesia and then RV free wall, left ventricle (LV) and septum tissue were harvested and weighted. RV hypertrophy was calculated by Fulton index as the weight ratio of RV and (LV+septum). Then, RV tissue was saved frozen (−80° C.) for biochemical analyses. Hematocrit was obtained for each mouse immediately after euthanasia.

Serum Human IgG assessment

Serum PDGF-B antibody human IgG is captured on a Gyrolab Bioaffy™ 200 CD by a biotinylated mouse anti-human IgG1/IgG4 monoclonal antibody (REGN2567) diluted in Glycerol and detected by an Alexa Fluor 647-Conjugated mouse anti-human kappa antibody diluted in Glycerol. The serum samples are proceeded as described below: 1) Dilute serum samples 1:50 in dilution buffer; dilute standards to a starting concentration of 2 µg/mL using dilution buffer for a total of 8 points standards. 2) Dilute biotinylated mouse anti-human IgG1/IgG4 to 100 ug/mL in washing. 3) Dilute Alexa Fluor 647-Conjugated mouse anti-human kappa antibody to 10 ug/mL in washing buffer. 4) Centrifuge capture and detection antibody at 15,000 RCF for 5 minutes. 5) Further dilute detect antibody (use the top layer of the centrifuged detect antibody only) to final concentration of 0.5 ug/mL in detection buffer. 6) Using GYROS generated plate map, load samples, standards, wash buffers, and capture and detect antibodies on to 96 well PCR plate.

Statistical Analyses

Quantitative data are expressed as mean±standard deviation. Statistical analyses performed between two groups were analyzed by t-test. Comparison of the time-course was analyzed by Two-ways analysis of variance (ANOVA) Comparison of treatment effect of multiple drug treatment groups was analyzed by one-way ANOVA. Prism software was used for all statistical analyses. A p-value <0.05 was considered statistically significant.

The dosing schedules for Study 1 are provided in Table 11.

TABLE 11

Therapeutic dosing and treatment protocol for each group in chronic hypoxia mouse model studies

| Group | Condition | Treatment | REGN# | Dosage | Frequency | Route | Starting day | Number of mice/group |
|---|---|---|---|---|---|---|---|---|
| 1 | Normobaric normoxia | Saline | N/A | 5 mL/kg | 2x/week | SC | 21 | 15 |
| 2 | Normobaric 10% hypoxia/Sugen5416 6 weeks | Isotype control antibody | REGN1945 | 25 mg/kg | 2x/week | SC | 21 | 15 |
| 3 | Normobaric 10% hypoxia/Sugen5416 6 weeks | Anti-PDGF-B antibody | H4H13145P | 25 mg/kg | 2x/week | SC | 21 | 15 |
| 4 | Normobaric 10% hypoxia/Sugen5416 6 weeks | Anti-PDGFRβ antibody | REGN2176 | 25 mg/kg | 2x/week | SC | 21 | 15 |

The dosing schedules for Study 2 are provided in Table 12.

TABLE 12

Therapeutic dosing and treatment protocol for each group in chronic hypoxia mouse model studies

| Group | Condition | Treatment | REGN# | Dosage | Frequency | Route | Starting day | Number of mice/group |
|---|---|---|---|---|---|---|---|---|
| 1 | Normobaric normoxia | Saline | N/A | 5 mL/kg | 2x/week | SC | 21 | 10 |
| 2 | Normobaric 10% hypoxia/Sugen5416 6 weeks | Isotype control antibody | REGN1945 | 25 mg/kg | 2x/week | SC | 21 | 12 |

TABLE 12-continued

Therapeutic dosing and treatment protocol for each group in chronic hypoxia mouse model studies

| Group | Condition | Treatment | REGN# | Dosage | Frequency | Route | Starting day | Number of mice/group |
|---|---|---|---|---|---|---|---|---|
| 3 | Normobaric 10% hypoxia/Sugen5416 6 weeks | Anti-PDGF-B antibody | H4H13145P | 1 mg/kg | 2x/week | SC | 21 | 12 |
| 4 | Normobaric 10% hypoxia/Sugen5416 6 weeks | Anti-PDGF-B antibody | H4H13145P | 3 mg/kg | 2x/week | SC | 21 | 12 |
| 5 | Normobaric 10% hypoxia/Sugen5416 6 weeks | Anti-PDGF-B antibody | H4H13145P | 10 mg/kg | 2x/week | SC | 21 | 12 |
| 6 | Normobaric 10% hypoxia/Sugen5416 6 weeks | Anti-PDGF-B antibody | H4H13145P | 25 mg/kg | 2x/week | SC | 21 | 12 |

Ultrasound Assessment and Analysis

On the last day of each study, pulmonary artery size and right ventricular function and dimensions were assessed in each mouse using a high frequency ultrasound system (Vevo 2100, VisualSonics). For the assessment, mice were anesthetized (with 1.5% isoflurane at a rate of 1.0 cc/mL of medical grade air) and their temperature was monitored with a rectal temperature probe and held at approximately 37° C. with a heated platform (MouseMonitorS, Indus Instruments) and a warming lamp. Both brightness-mode (B-mode) and motion-mode (M-mode) imaging were used. B-mode imaging of the mouse heart in cross-section was used to determine pulmonary artery cross-sectional area (PA CSA) at the level of the pulmonary valve. M-mode imaging was used to determine the pulsed wave velocity time integral (VTI), which is derived from the area under the curve of representative Doppler tracings of blood flow through the pulmonary artery. Right ventricular stroke volume (RV SV) was calculated from the product of PA CSA and VTI. Right ventricular cardiac output (RV CO) was calculated from the product of SV and heart rate (HR). M-mode imaging was used to determine right ventricular free wall (RVFW) thickness during diastole and systole. Animals were returned to their home cages before right ventricular pressure assessment.

Right Ventricular Pressure Assessment

Right ventricular pressure was subsequently assessed for all treatment groups. Mice were anesthetized with isoflurane and were kept at approximately 37° C. using a heated platform (Heated Hard Pad 1, Braintree Scientific) and circulating heated water pump (T/Pump Classic, Gaymar Industries). The neck area for each mouse was prepared for surgery by depilating over the right common carotid artery and right jugular vein. An incision was made and the right jugular vein was isolated with care as to not damage the carotid artery and/or the vagus nerve. A piece of 5-0 silk suture was placed under the isolated jugular vein to allow for retraction of the vessel cranially, then a 30-guage needle was used to introduce a hole into the jugular vein. A pressure catheter (Micro-tip catheter transducer SPR-1000, Millar Instruments, Inc.) was inserted into the opening of the jugular vein and advanced past the right atrium into the right ventricle. The catheter was connected to pressure/volume instrument (MPVS-300, Millar Instruments, Inc.) that measured heart rate as well as both diastolic and systolic right ventricular pressures. These parameters were digitally acquired using a data acquisition system (PowerLab 4/35, ADInstruments). LabChart Pro 7.0 software (ADInstruments) was used to analyze right ventricular pressures.

Readings were quantified from a 60 second interval of the pressure tracing (following a 2 minute period of recording to allow for pressure stabilization). The parameters analyzed were right ventricular systolic pressures (RVSP), heart rate (HR) and rate of right ventricular pressure rise (dP/dt max).
Serum/tissue collection and assessment of right ventricular hypertrophy Following completion of right ventricular pressure measurement, the catheter was removed and each animal was sacrificed. The abdomen was opened and blood was drawn from the Vena Cava for hematocrit assessment and serum collection. The thoracic cavity was then opened and the middle lobe of the right lung was ligated with 5-0 silk suture, excised, placed in RNA later (Sigma-Aldrich, cat #R0901) and frozen 24 hours later at −80° C. The heart was excised from each animal, and the right ventricle (RV) was carefully cut away from the left ventricle and septum (LV+S). Both pieces of heart tissue were separately weighed on a microbalance (AJ000, Mettler) to calculate the index of RV hypertrophy [RV/(LV+S); Fulton Index].

Half of the animals from each treatment group had the lungs perfused at 20-25 mmHg with phosphate buffered solution (PBS, pH 7.4), then fixed with 10% neutral-buffered formalin (NBF). Lungs remained in 10% NBF for 24 hours before being placed into 70% ethanol for at least 48 hours, before tissue processing and paraffin embedding. For animals that did not undergo perfusion-fixation of the lung, the right inferior lobe was ligated with 5-0 silk suture before being excised, weighed and frozen in liquid $N_2$.

Rats

Six to seven weeks old male Sprague Dawley rats were used. Rats were separated into treatment groups such that body weights were similar among different groups. In study 1, one day prior of monocrotaline injection, rats in antibody treatment groups were subcutaneously administered either anti-PDGF-B antibody or isotype control IgG at 25 mg/kg 2 times a week for 28 days. Standard of care group was orally administered macitentan at 30 mg/kg daily for 28 days. At day one, rats were subcutaneously administered either 40 mg/kg of monocrotaline or 5 mL/kg of saline. By the end of day 28, right ventricular systolic pressure (RVSP) was measured by right heart catheterization and RV hypertrophy was calculated by Fulton index as the weight ratio of RV and (LV+septum). In study 2, rats were subcutaneously administered either 60 mg/kg of monocrotaline or 5 mL/kg of saline. Starting at day 14, rats in antibody treatment groups were subcutaneously administered either anti-PDGF-B antibody or isotype control IgG at 25 mg/kg 2 times a week for 21 days. Body weight change from day 0-35 were used for general toxicity assessment and animal mortality was calculated by day 35.

The dosing schedules for Study 1 are provided in Table 13.

TABLE 13

4 weeks Monocrotaline PAH Rats with Preventive Drug Treatment

| Group | Condition | Treatment | REGN# | Dosage | Frequency | Route | Starting day | Number of rat/ group |
|---|---|---|---|---|---|---|---|---|
| 1 | Saline | Saline | N/A | 5 mL/kg | once at day 1 | SC | N/A | 10 |
| 2 | Monocrotaline (40 mg/kg) + Isotype control IgG | Isotype control antibody | REGN1945 | 25 mg/kg | 2x/week | SC | −1 | 12 |
| 3 | Monocrotaline (40 mg/kg) + Anti-PDGF-B | Anti-PDGF-B antibody | H4H13145P | 25 mg/kg | 2x/week | SC | −1 | 12 |
| 4 | Monocrotaline (40 mg/kg) + Macitentan | Macitentan | N/A | 30 mg/kg | daily | P.O. | −1 | 12 |

The dosing schedules for Study 2 are provided in Table 14.

TABLE 14

5 weeks Monocrotaline Severe PAH Rats Survival with Therapeutic Drug Treatment

| Group | Condition | Treatment | REGN# | Dosage | Frequency | Route | Starting day | Number of Rat/ group |
|---|---|---|---|---|---|---|---|---|
| 1 | Saline | Saline | N/A | 5 mL/kg | once at day 1 | SC | N/A | 10 |
| 2 | Monocrotaline (60 mg/kg) + Isotype control IgG | Isotype control antibody | REGN1945 | 25 mg/kg | 2x/week | SC | 14 | 12 |
| 3 | Monocrotaline (60 mg/kg) + Anti-PDGF-B | Anti-PDGF-B antibody | H4H13145P | 25 mg/kg | 2x/week | SC | 14 | 12 |

Right Heart Catheterization and Right Ventricular Systolic Pressure

Rats were anesthetized with isoflurane and were kept at approximately 37° C. using a heated platform (Heated Hard Pad 1, Braintree Scientific) and circulating heated water pump (T/Pump Classic, Gaymar Industries). The neck area for each rat was prepared for surgery by depilating over the right common Carotid artery and right Jugular vein. An incision was made and the right Jugular vein was isolated with care as to not damage the Carotid artery and/or the Vagus nerve. A piece of 5-0 silk suture was placed under the isolated Jugular vein to allow for retraction of the vessel cranially, then a 23-guage needle was used to introduce a hole into the Jugular vein. A pressure catheter (Micro-tip catheter transducer SPR-1000, Millar Instruments, Inc.) was inserted into the opening of the Jugular vein and advanced past the right atrium into the right ventricle. The catheter was connected to pressure/volume instrument (MPVS-300, Millar Instruments, Inc.) that measured heart rate as well as both diastolic and systolic right ventricular pressures. These parameters were digitally acquired using a data acquisition system (PowerLab 4/35, AD Instruments). LabChart Pro 7.0 software (AD Instruments) was used to analyze right ventricular pressures. Readings were quantified from a 60 second interval of the pressure tracing (following a 2 minute period of recording to allow for pressure stabilization). The parameters analyzed were right ventricular systolic pressures (RVSP), heart rate (HR) and rate of right ventricular pressure rise (dP/dt max).

Right Heart Hypertrophy Assessment

After the in vivo hemodynamic measurements, animals were euthanized by exsanguinations under anesthesia and then RV free wall, left ventricle (LV) and septum tissue were harvested and weighted. RV hypertrophy was calculated by Fulton index as the weight ratio of RV and (LV+septum). Then, RV tissue was saved frozen (−80° C.) for biochemical analyses.

Statistical Analyses

Quantitative data are expressed as mean±standard deviation. Statistical analyses performed between two groups were analyzed by t-test. Comparison of the time-course was analyzed by Two-ways analysis of variance (ANOVA) Comparison of treatment effect of multiple drug treatment groups was analyzed by one-way ANOVA. Prism software was used for all statistical analyses. A p-value <0.05 was considered statistically significant.

Results

Anti-PDGF-B Provided Superior Efficacy in Two Clinically Relevant Endpoints of PAH when Compared Directly with Anti-PDGFRβ

Body Weight Change in Hypoxia/Sugen Mice

Figure 10:
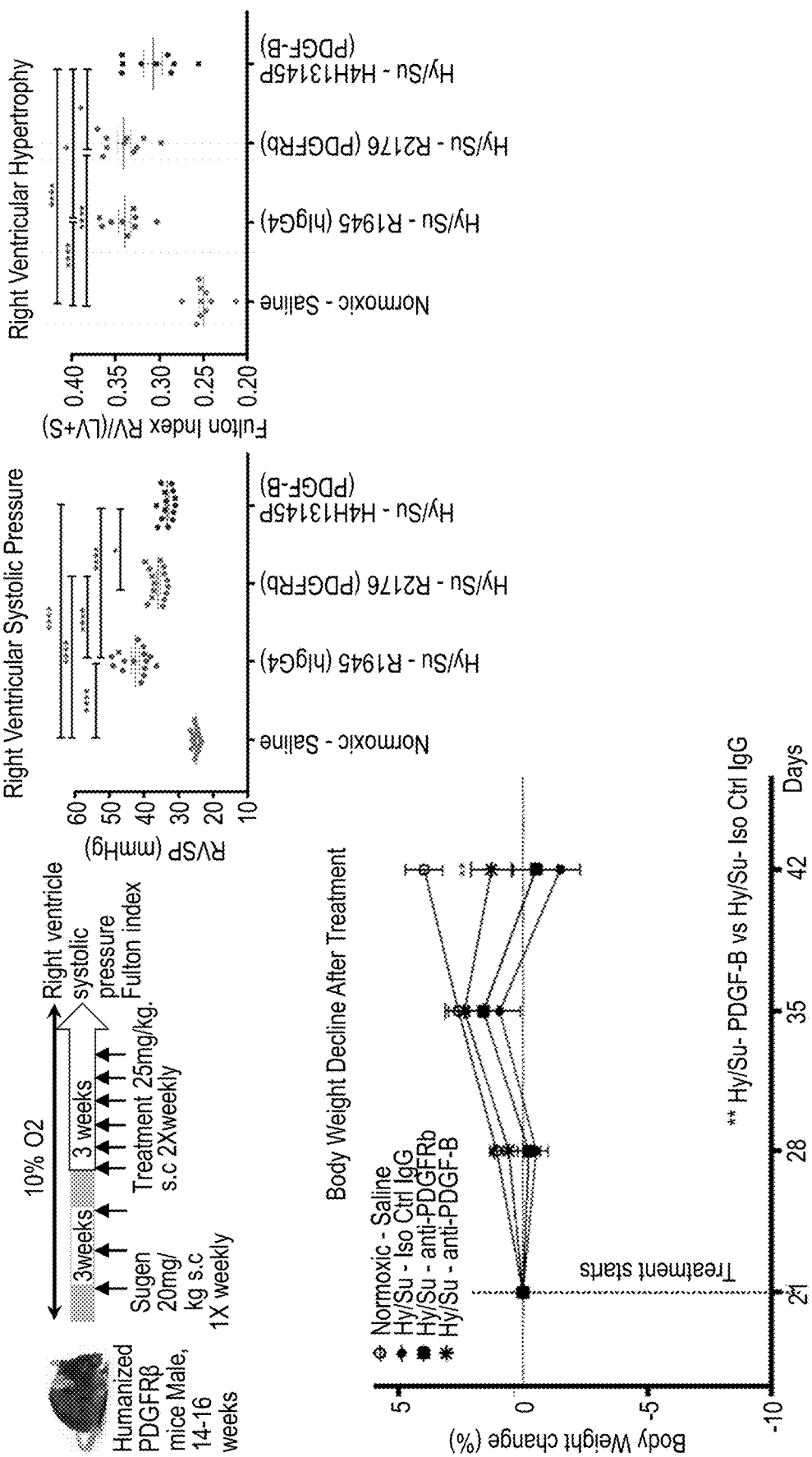
FIG. 10 is a panel of graphs depicting that anti-PDGF-B provided superior efficacy in two clinically relevant endpoints (right ventricular pressure and hypertrophy) of PAH when compared directly with anti-PDGFR-β.

Mice exposed to hypoxia displayed slower body weight growth in 6 weeks in comparison with animal under normoxia. The anti-PDGF-B antibody treatment significantly attenuated the body weight loss compared with isotype control hIgG4 treatment group. The anti-PDGFRβ antibody treatment did not show any impact in body weight change caused by hypoxia exposure (FIG. 10). Significant difference was found at the day 42 time point only between Hy/Su+Isotype Control IgG and Hy/Su+Anti-PDGF-B (**p<0.01).

Right Ventricular Pressure Elevation Induced in Hypoxia/Sugen Mice

Catheter-based assessment of heart right ventricular pressures revealed a significant elevation of right ventricle systolic pressures in the isotype antibody-treated group in hypoxia/sugen mice at week 6. The anti-PDGF-B antibody treatment significantly reduced right ventricular systolic pressure elevation by 9 mmHg while anti-PDGFRβ antibody also reduced right ventricular systolic pressure to a lesser extent (FIG. 10). Significant differences were found between Hy/Su+Isotype Control IgG and Hy/Su+Anti-PDGF-B (**p<0.0001) and Hy/Su+Anti-PDGFRβ (**p<0.0001). Significant difference was also found between Hy/Su+PDGFRβ and Hy/Su+Anti-PDGF-B (*p<0.05).

Right Ventricular Hypertrophy Induced in Hypoxia/Sugen Mice

The post-mortem analysis of the mouse right heart weight found a significant change in hypoxia/sugen exposed mice (FIG. 10). The ratio of the right ventricular weight to the left ventricular plus septal weight provides an index of right ventricular hypertrophy (i.e., Fulton Index), and the groups in hypoxia/sugen for 6 weeks showed greater ratios relative to normoxic animals, indicating the presence of right ventricular hypertrophy. Therapeutic treatment of anti-PDGF-B antibody lessened right ventricular hypertrophy by ~35% when compared to the hypoxia/sugen isotype control-treated mice. Use of anti-PDGFRβ antibody failed to reduce right ventricular hypertrophy in hypoxia/sugen exposed animal. Significant difference was found between Hy/Su+Isotype Control IgG and Hy/Su+Anti-PDGF-B (****p<0.0001) and Hy/Su+Anti-PDGFRβ (*p<0.05). Significant difference was also found between Hy/Su+PDGFRβ and Hy/Su+Anti-PDGF-B (*p<0.05).

In summary, anti-PDGF-B antibody provided superior efficacy in two clinically relevant endpoints (right ventricular pressure and hypertrophy) of PAH when compared directly with anti-PDGFRβ in hypoxia/sugen mice mode.

Figure 11:
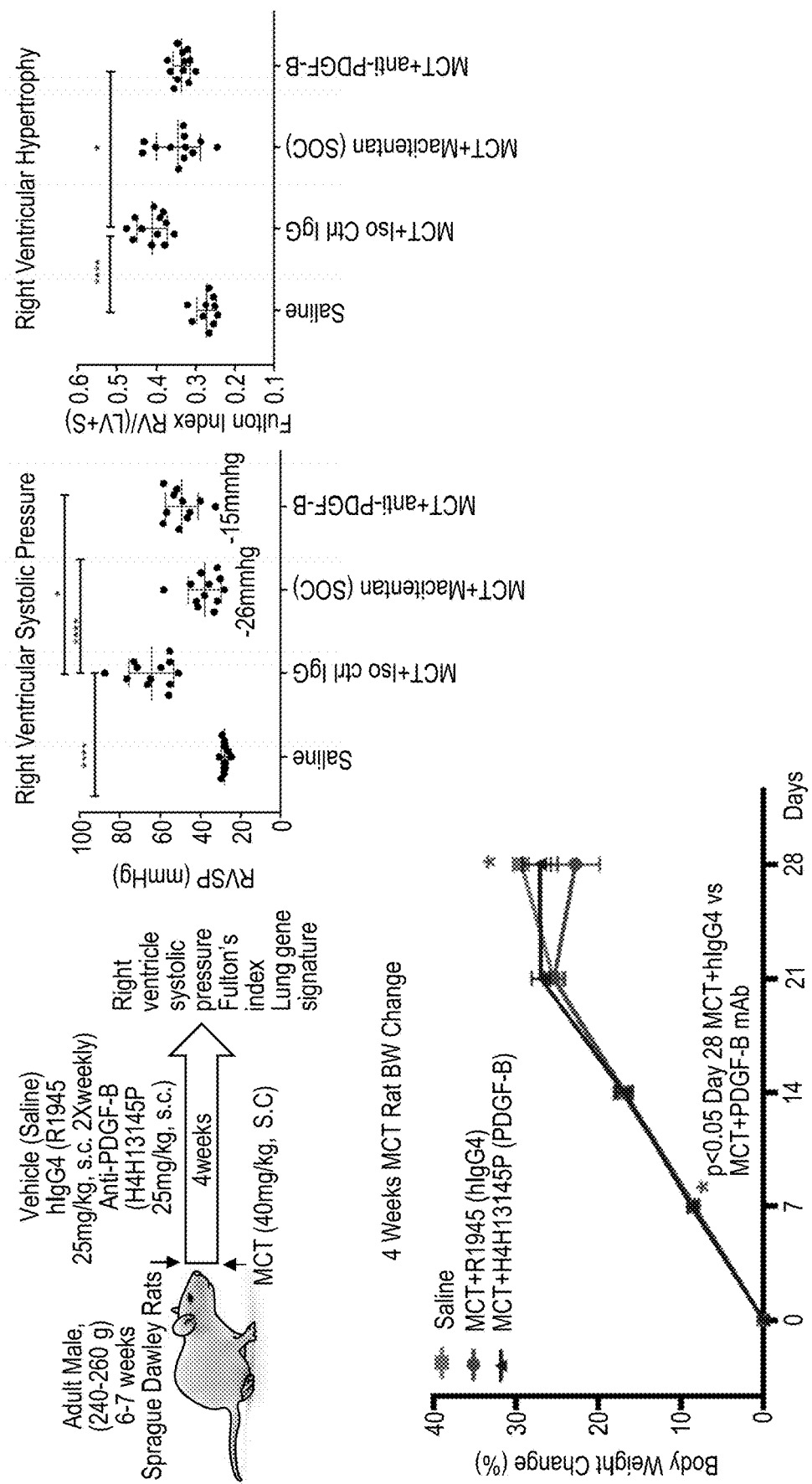
FIG. 11 is a panel of graphs depicting that preventative treatment with anti-PDGF-B reduced both a hemodynamic endpoint (RVSP) and right ventricle hypertrophy in this rat model of PAH.

Preventive Treatment of Anti-PDGF-B Potently Protects Animal in MCT Rat and Therapeutic Treatment of Anti-PDGF-B Improves Survival in High Dose MCT Rat Right Ventricular Pressure Elevation Induced in Monocrotaline Rats In study 1 catheter-based assessment of heart right ventricular pressures revealed a significant elevation of right ventricle systolic pressures in the isotype antibody-treated group in monocrotaline rats by week 4. Both vasodilatory agent Macitentan and the anti-PDGF-B antibody treatments significantly reduced right ventricular systolic pressure elevation. Significant differences were found between Monocrotaline+Isotype Control IgG and Monocrotaline+Macitentan (***p<0.001) and Monocrotaline+Anti-PDGF-B (*p<0.05) (FIG. 11).

Right Ventricular Hypertrophy Induced in Monocrotaline Rats

The post-mortem analysis of the rat right heart weight found a significant change in monocrotaline rat with isotype control IgG treatment. The ratio of the right ventricular weight to the left ventricular plus septal weight provides an index of right ventricular hypertrophy (i.e., Fulton Index), and the groups in monocrotaline treated rats for 4 weeks showed greater ratios relative to saline treated animals, indicating the presence of right ventricular hypertrophy. Preventive (treatment of anti-PDGF-B antibody lessened right ventricular hypertrophy by ~40% when compared to the monocrotaline with isotype control-treatment rats (FIG. 11). Use of vasodilatory agent Macitentan failed to reduce right ventricular hypertrophy in monocrotaline rats. Significant difference was found between Monocrotaline+Isotype Control IgG and Monocrotaline+Anti-PDGF-B (*p<0.05).

Animal Survival Rate in Monocrotaline Rats

Figure 12:
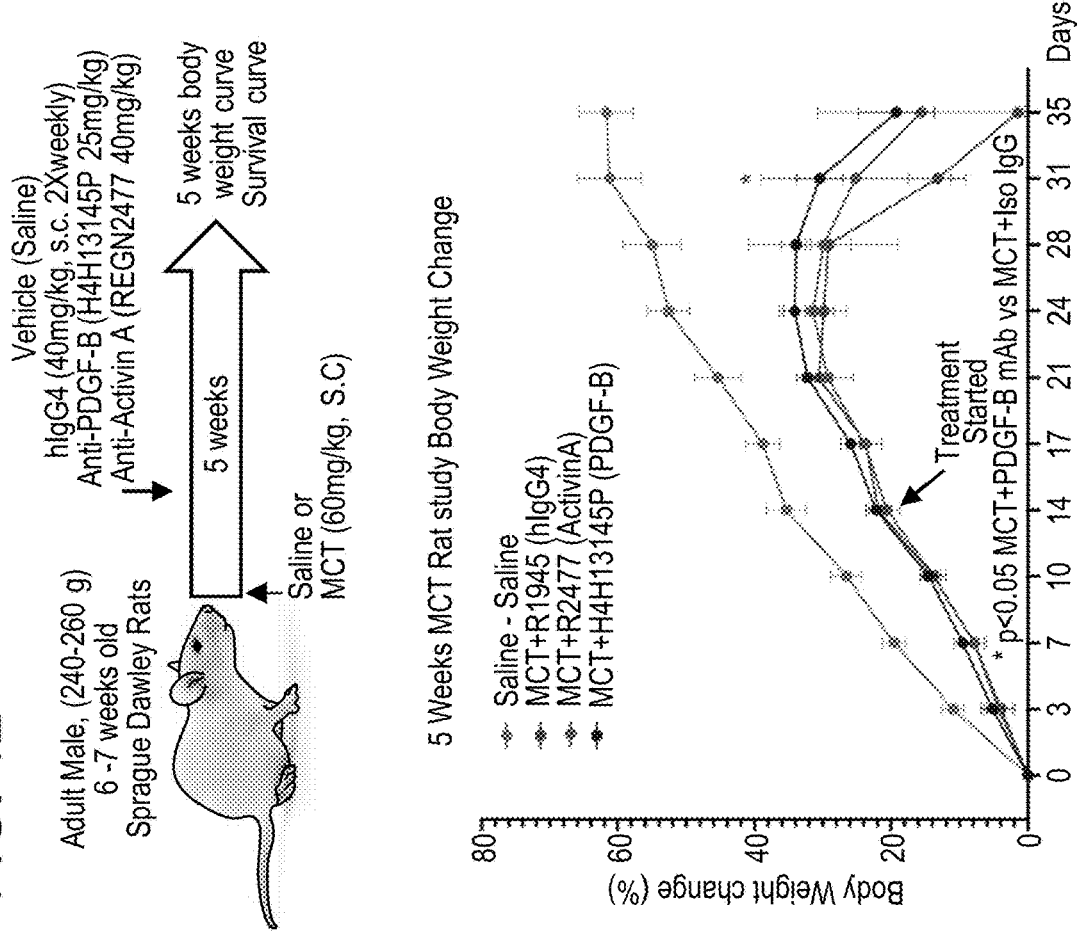
FIG. 12 is a panel of graphs depicting that anti-PDGF-B robustly improved survival time in the severe MCT Rat model of PAH.

In study 2, the rats injected with 60 mg/kg monocrotaline developed severe pulmonary hypertension symptoms and high mortality. Notably, 90% of animal in monocrotaline with isotype control IgG treatment group died by day 35. The anti-PDGF-B antibody treatment started 14 post monocrotaline injection and significantly attenuated animal body weight loss. Significant difference was found between Monocrotaline+Isotype Control IgG and Monocrotaline+Anti-PDGF-B at day 28 (*p<0.05) and day 35 (***p<0.001). PDGF-B antibody treatment also rescued 58% of rats from death by day 35. Significant difference was found between Monocrotaline+Isotype Control IgG and Monocrotaline+Anti-PDGF-B (*p<0.05) and rescued 58% of rats from death by day 35 (FIG. 12).

In summary, preventative treatment with an anti-PDGF-B antibody reduced both a hemodynamic endpoint (right ventricular systolic pressure) and right ventricular hypertrophy in monocrotaline model. Therapeutic treatment of an anti-PDGF-B antibody significantly improved animal survival in severe PAH of monocrotaline Rats.

Anti-PDGF-B Demonstrated Efficacy in Low Dose Therapeutic Treatment

Right Ventricular Pressure Elevation Induced in Hypoxia/Sugen Mice

Catheter-based assessment of heart right ventricular pressures revealed a significant elevation of right ventricle systolic pressures in the isotype antibody-treated group in hypoxia/sugen mice by week 6. The anti-PDGF-B antibody treatments significantly reduced right ventricular systolic pressure elevation at 1, 3, 10 and 25 mg/kg doses. Significant differences were found between Hy/Su+Isotype Control IgG and Hy/Su+Anti-PDGF-B groups at 1 mg/kg (*p<0.05), 3 mg/kg (*<0.01); 10 mg/kg (**p<0.0001) and 25 mg/kg (**p<0.0001). There was no statistically significant difference among different dose of PDGF-B treatments (FIG. 13A).

Right Ventricular Hypertrophy Induced in Hypoxia/Sugen Mice

The post-mortem analysis of the mouse right heart weight found a significant change in hypoxia/sugen exposed mice (FIG. 13A). The ratio of the right ventricular weight to the left ventricular plus septal weight provides an index of right ventricular hypertrophy (i.e. Fulton Index), and the groups in hypoxia/sugen for 6 weeks showed greater ratios relative to normoxic animals, indicating the presence of right ventricular hypertrophy. Therapeutic treatment of anti-PDGF-B antibody did not change right ventricular hypertrophy compared to the hypoxia/sugen isotype control-treated mice. Significant differences were found between Normoxia group and all Hy/Su groups ($^{\#\#\#\#\#}$ p<0.0001).

Serum PDGF-B Protein and Antibody Levels in Hypoxia/Sugen Mice

By week 6, serum was collected for circulating PDGF-B protein and human antibodies analysis. Circulating levels of PDGF-B were significantly elevated in hypoxia/sugen mice group (FIG. 13B). The measurement of human IgG in mice serum confirmed that the antibody levels in 1-25 mg/kg anti-PDGF-B treatment groups increased dose dependently. 1-25 mg/kg repeated subcutaneous dosing achieved nM level serum antibody levels that are thousand times of circulation PDGF-B (FIG. 13B).

In summary, circulating PDGF-BB was elevated in Hy/Su PAH mice. The anti-PDGF-B antibody demonstrated efficacy in improving pulmonary hemodynamics (right ventricular pressure) down to 1 mg/kg dosage in hypoxia/sugen mice mode.

The in-vivo efficacy for targeting PDGF-B signaling is summarized in Table 15 below.

to endothelial hyperplasia, abnormal vascular morphogenesis and formation of microaneurysms. Mice with ablation of endothelial derived PDGF-B showed <52% of normal pericyte density leading to variable capillary and venous diameter, regressing capillary branches. Specific overexpression of PDGF-B in photoreceptor cells resulted in increased proliferation of pericytes, but also astrocytes and endothelial cells. Long term treatment of PDGF-B versus PDGF-Rb antagonist potentially might cause pericyte loss/vessel damage and subsequent Edema and Hemorrhage in humans. Further, systemic toxicity of an anti-PDGFRβ pegylated di-Fab (Celltech/Zymogenetics) has been reported in humans (peripheral edema in patients with cancer), and the safety of long term anti-PDGF-B therapy is unknown.

The inventors hypothesized that specific PDGF-B ligand blockade would allow continued receptor signaling through remaining PDGF ligands and result in less negative impact on pericyte homeostasis. It was discovered that systematic administration of Anti-PDGF-B ab at 3 mg/kg s.c did not cause retinal vessel pericytes loss in neonatal mice, while anti-PDGFRb ab depleted retinal vessel pericytes completely. Adult rodents were observed to be tolerant to high dose anti-PDGF-B and anti-PDGFRb treatment. Further, an

TABLE 15

| Agent | Monocrotaline Rat - Prevention | | | high dose Monocrotaline Rat-Therapeutic | | Hypoxia/Sugen Mice - Therapeutic | | | Hypoxia/Sugen Mice - Therapeutic dose response | | |
|---|---|---|---|---|---|---|---|---|---|---|---|
| | Dose (mg/kg) | Reduction in RVSP (mmHg) | % reduction in RV hypertrophy | Dose (mg/kg) | Mortality | dose (mg/kg) | Reduction in RVSP (mmHg) | % reduction in RV hypertrophy | dose (mg/kg) | Reduction in RVSP (mmHg) | % reduction in RV hypertrophy |
| PDGF-B (H4H13145P) | 25 | 14 | 50-60 | 25 | 91%-->58% | 25 | 9 | 35 | 1 | 6 | no protection |
| Endothelin receptor antagonist SOC (Macitentan) | 30 | 19-25 | trend | 30 | N/A | 30 | 19-25 | trend | 30 | 19-25 | trend |
| ACVRIIa-Fc (Sotatercept) (vessel remodeling comparator drug) | 25 | 14 | no protection | 25 | N/A | N/A | N/A | N/A | N/A | N/A | N/A |
| PDGFRb (REGN2176) | N/A | N/A | N/A | N/A | N/A | 25 | 6 | no protection | 25 | 6 | no protection |

Targeting PDGF-B via lead mAb (H4H13145P) has demonstrated consistent and robust efficacy across clinically relevant PAH endpoints (Right Ventricular Systolic Pression—RVSP; Right Ventricular Hypertrophy—RV) in rodent models. These effects were more impressive than any treatment or benchmark to date including a standard of care drug, a comparator clinically investigational drug, and in house PDGFRb blockade. PDGF-B blocker may provide an effective non-vasodilator PAH therapy.

Example 11. Safety Assessment of Blockade of PDGFR-β

PDGF-B/PDGFRb signaling is involved in pericyte proliferation, migration, survival and attachment. Sprouting endothelial cells secrete PDGF-B, which binds to the pericyte-specific receptor PDGFRb, leading to the recruitment and attachment of pericytes. Impaired PDGF-B/PDGFRb signaling results in a failure of pericyte recruitment and in reduced microvascular pericyte coverage ultimately leading 8 months high dose of anti-PDGFRb treatment in adult mice did not induce any vessel damage, bleeding or apparent edema.

Figure 14:
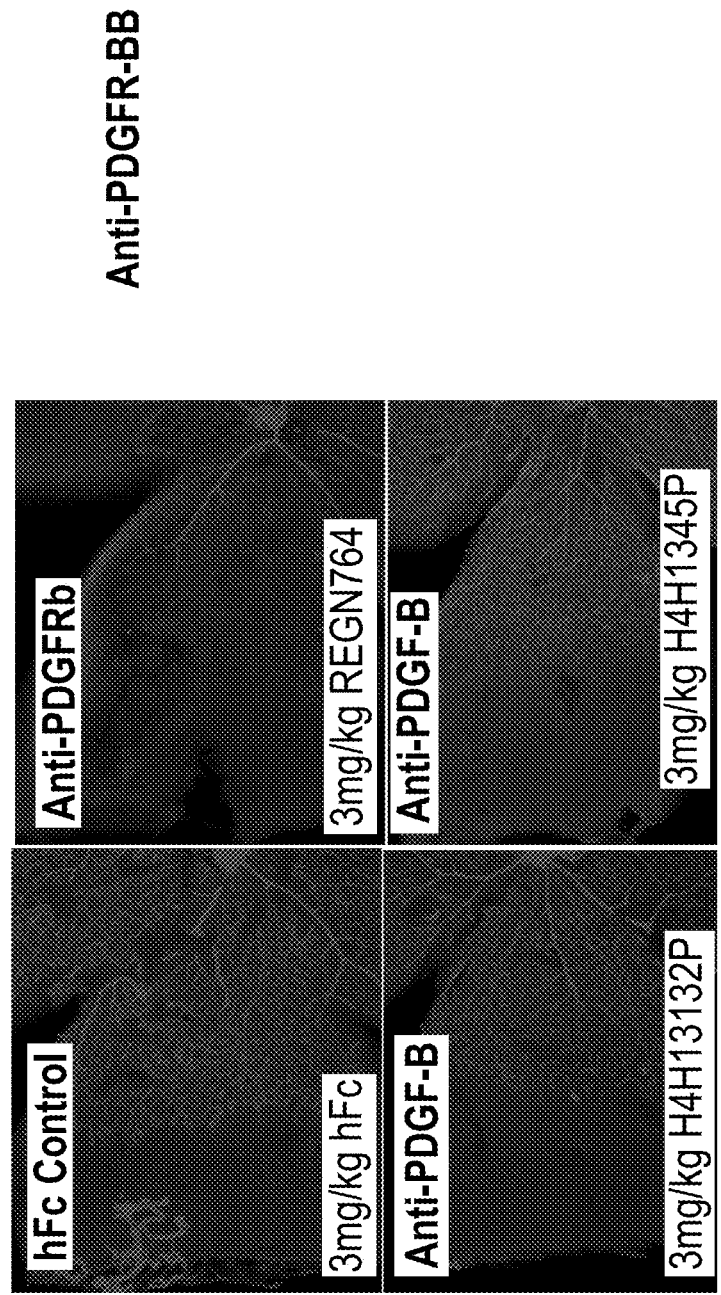
FIG. 14 is a panel of images of pericytes depicting that while systemic delivery of anti-PDGF-Rβ antibody (2C5, REGN764) effectively depleted pericytes, anti-PDGF-BB antibodies had no apparent effect in the Retinal Vascular Development (RVD) model at 3 mg/kg.

In analyzing the effect of anti-PDGF-B antibodies on P2 wild-type mice retinal vasculature, there was no observed effect on the pericyte coverage in anti-PDGF BB treated retinas at 3 mg/kg dosage. While systemic delivery of anti-PDGF-Rβ antibody (2C5, REGN764) effectively depleted pericytes, the anti-PDGF-BB antibodies (H4H13132P and H4H13145P) had no apparent effect in the Retinal Vascular Development (RVD) model at 3 mg/kg (FIG. 14).

Figure 15:
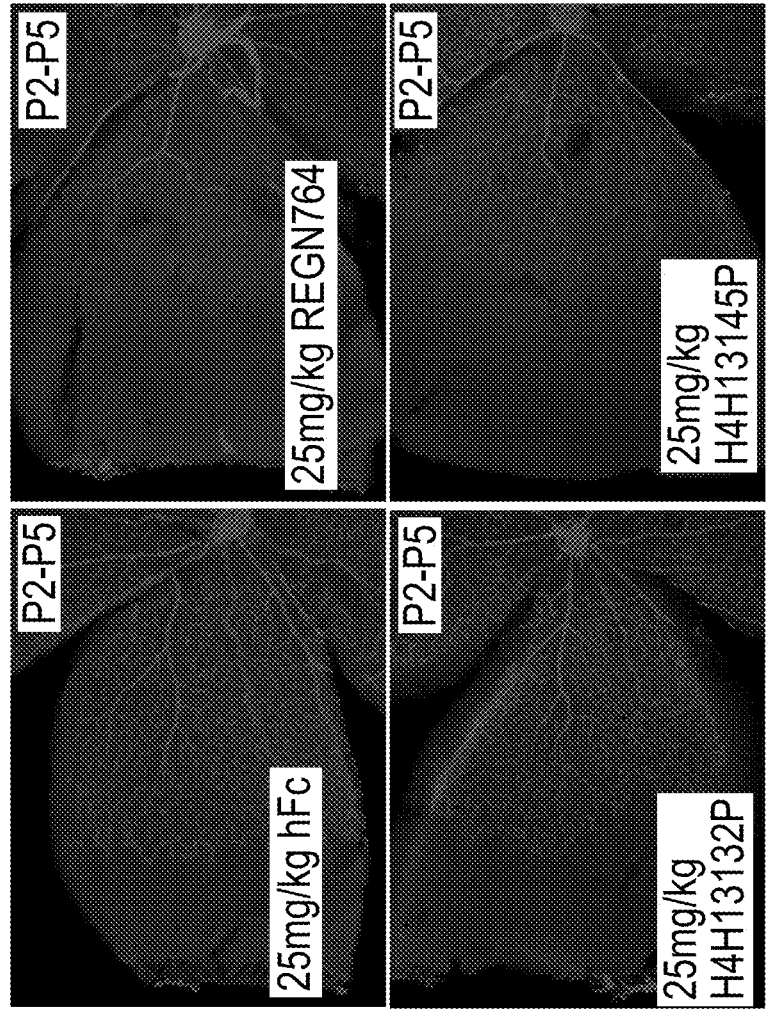
FIG. 15 is a panel of images of pericytes depicting that a higher dose (25 mg/kg) of H4H13145P has a moderate effect on pericyte depletion in the RVD model.

To determine effect of anti-PDGF-B antibodies on retinal vasculature in P2 WT mice, the anti-PDGF-B antibodies were injected at P2; and tissue was collected at P5. All retinas were incubated with anti-NG2 antibody to detect vessel pericytes. A higher dose of the anti-PDGF-B antibody (H4H13145P) was observed to exhibit a moderate effect on pericyte depletion in the RVD model (FIG. 15).

Accordingly, this study demonstrates that the use of anti-PDGF-B antibodies provide a better safety profile relative to the use of anti-PDGFR-β antibodies, and specific PDGF-B ligand blockade would allow continued receptor signaling through remaining PDGF ligands in order to maintain pericyte functionality.

Example 12. Pharmacokinetic Profile of Anti-PDGF-B Antibodies

The pharmacokinetic (PK) profile of anti-PDGF-B antibodies was determined in C57BL/6 WT mice at three different doses. Both anti-PDGF-B monoclonal antibodies used in this study cross mouse PDGF-BB with sub-nanomolar affinities at 37° C. Twenty-six weeks old female mice (Total=36 mice; WT on 100% C57BL/6 background) were administered a single subcutaneous dose of 0.1, 1, or 10 mg/kg and analyzed at bleed time points of 6 hours, day 1, day 2, day 3, day 4, day 7, day 10, day 15, day 22, and day 30. The total human IgG was determined by Gyros: mouse anti-human kappa light chain constant (REGN654*biotin) mAb Capture/mouse anti-human IgG1/IgG4 (REGN2567*Alexa647) mAb Detect. Functional binding was determined by Gyros: mouse PDGF-BB*biotin capture/mouse anti-human IgG1/IgG4 (REGN2567*Alexa647) mAb Detect.

The doses of the anti-PDGF-B antibodies and the hIgG4 isotype control used in the pharmacokinetic study are described in Table 16.

TABLE 16

| Test Article | hPDGF-BB $K_D$ @ 37° C. * | mPDGF-BB $K_D$ @ 37° C. * | Isotype | Target | Dose | n |
|---|---|---|---|---|---|---|
| H4H13145P | 1.36E−12 | 9.54E−13 | hIgG4$^P$ | Anti-PDGF-B | 10 mg/kg | 4 |
|  |  |  |  |  | 1 mg/kg | 4 |
|  |  |  |  |  | 0.1 mg/kg | 4 |
| H4H13132P | 1.84E−12 | 8.67E−11 | hIgG4$^P$ | Anti-PDGF-B | 10 mg/kg | 4 |
|  |  |  |  |  | 1 mg/kg | 4 |
|  |  |  |  |  | 0.1 mg/kg | 4 |
| REGN1945 | — | — | hIgG4$^P$ | Anti-Fel d 1 hIgG4$^P$ isotype control | 10 mg/kg | 4 |
|  |  |  |  |  | 1 mg/kg | 4 |
|  |  |  |  |  | 0.1 mg/kg | 4 |

Figure 16:
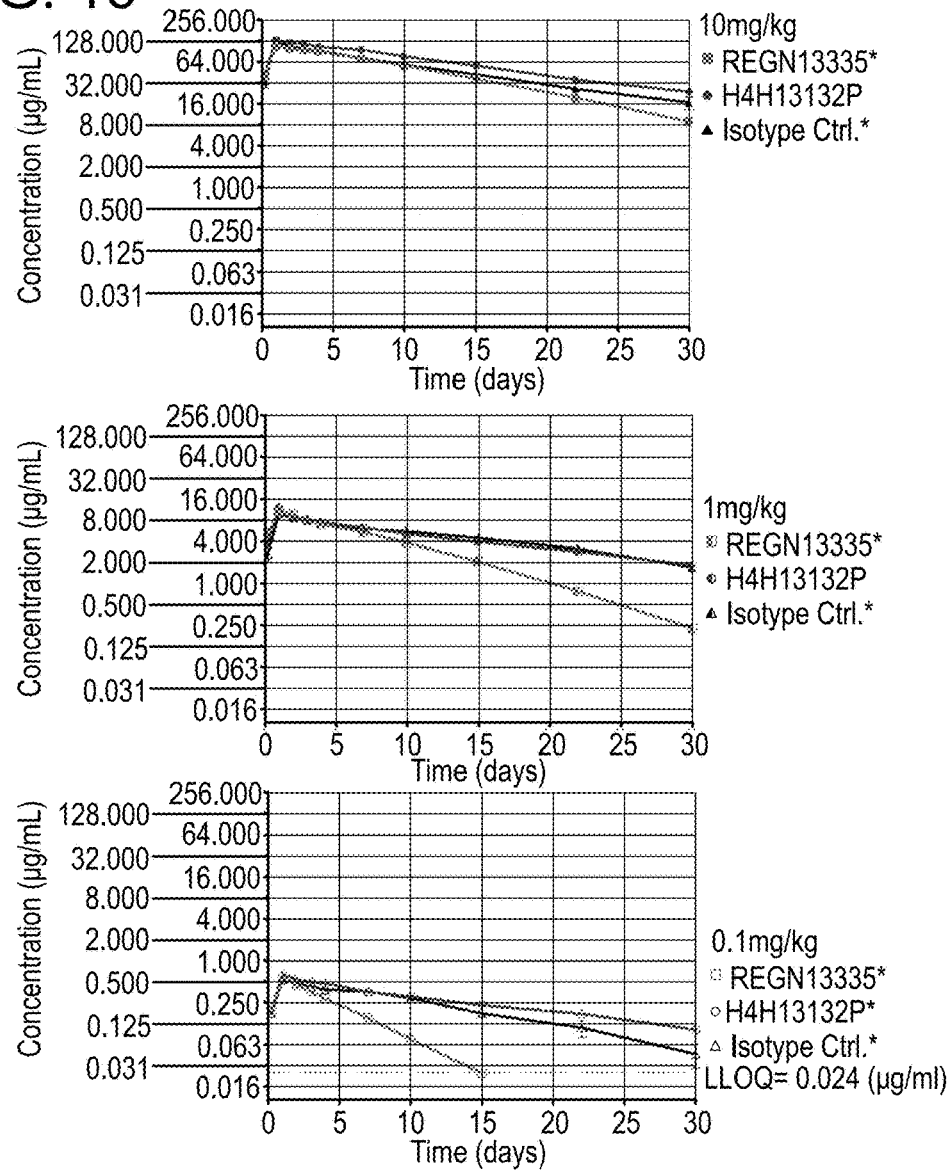
FIG. 16 is a panel of graphs and a Table depicting the pharmacokinetic profile of anti-PDFG-B antibodies in C57BL/6 wild-type mice at three single subcutaneous doses of 0.1, 1, or 10 mg/kg.

Overall, differences were observed between H4H13145P and H4H13132P (FIG. 16). H4H13145P exhibits faster clearance than the isotype control at 1 mg/kg and 0.1 mg/kg; and has a PK profile similar to the isotype control at 10 mg/kg. H4H13132P exhibits a PK profile similar to the isotype control at all doses. The greatest differences in drug exposure (AUClast) are observed at 1 mg/kg & 0.1 mg/kg when compared to H4H13145P. All the monoclonal antibodies that are tested reached similar Cmax at each respective dose. However a lower than expected Cmax was observed with all three monoclonal antibodies dosed at 0.1 mg/kg.

The clearance observed with H4H13145P at 1 mg/kg and 0.1 mg/kg is suggestive of target mediated clearance that may be driven by sub-picomolar affinity to mPDGF-BB. It is important to note that affinities to hPDGF-BB of each molecule are very similar, whereas there are differences in affinity between the molecules to mPDGF-BB.

Functional (mouse PDGF-BB) binding assays can be performed to examine unbound antibody concentrations in comparison to total hIgG concentrations.

A similar study is performed in cynomolgus monkeys in order to evaluate the PK profile of the anti-PDGF antibodies. Cynomolgus monkeys (Total=27) are administered a single subcutanaceous dose of 0.1, 1, or 10 mg/kg and analyzed at bleed time points of 6 hours, day 1, day 2, day 3, day 4, day 7, day 10, day 15, day 22, and day 30. The plasma is collected for PK analysis in order to determine the endpoints of target level (total bound and unbound PDGF-B), hFc level (total), and free target level (free PDGF-B) of the antibodies.

Example 13. Vessel Permeability Study of Anti-PDGF-B Antibodies

The pathobiologic mechanism of angioedema with regard to angiotensin-converting enzyme (ACE) inhibitor therapy (Captopril) is believed to relate to the kallikrein-kinin plasma effector system (see, Craig et al., 2014 *Int Arch Allergy Immunol.* 2014; 165(2):119-27; which is enclosed in its entirety herein by reference). Angioedema can occur due to inadequate degradation of bradykinin (BK). BK has a very short half-life of 17 seconds as it is rapidly metabolized by various metalloproteinases, such as ACE. ACE inhibitor, Captopril, by blocking the breakdown of bradykinin, increase bradykinin levels and results in vasodilation and increased vessel permeability.

A study was performed in order to evaluate whether the chronic treatment of healthy C57 adult mice with high doses of PDGF-BB antibodies have any additive impact in gastrointestinal (GI), lung, or brain vascular hyperpermeability. Taconic C57BL male mice of age 11-16 weeks were administered a subcutaneous dose of 25 mg/kg of the control IgG, anti-PDGF-B and anti-PDGFRβ antibodies twice per week, for 4 weeks, as described in FIG. 17. The Evans Blue (EB) assay was used to evaluate the impact of 4 Weeks treatment of anti-PDGF-B and PDGFRβ antibodies in baseline and ACE II inhibitor induced GI Vascular Permeability. Evans Blue (EB) dye reversibly binds to serum albumin with moderate affinity and has a long blood half-life. The binding of EB to albumin has been exploited to quantify protein leakage as an indicator of increased vascular permeability. Under physiologic conditions, the endothelium is impermeable to albumin, so Evans blue bound albumin remains restricted within blood vessels. In pathologic conditions that promote increased vascular permeability, endothelial cells partially lose their close contacts and the endothelium becomes permeable to small proteins such as albumin. Organs with increased permeability will show significantly increased blue coloration compared to organs with intact endothelium. The level of vascular permeability can be assessed by simple visualization or by quantitative measurement of the dye incorporated per milligram of tissue.

Figure 18:
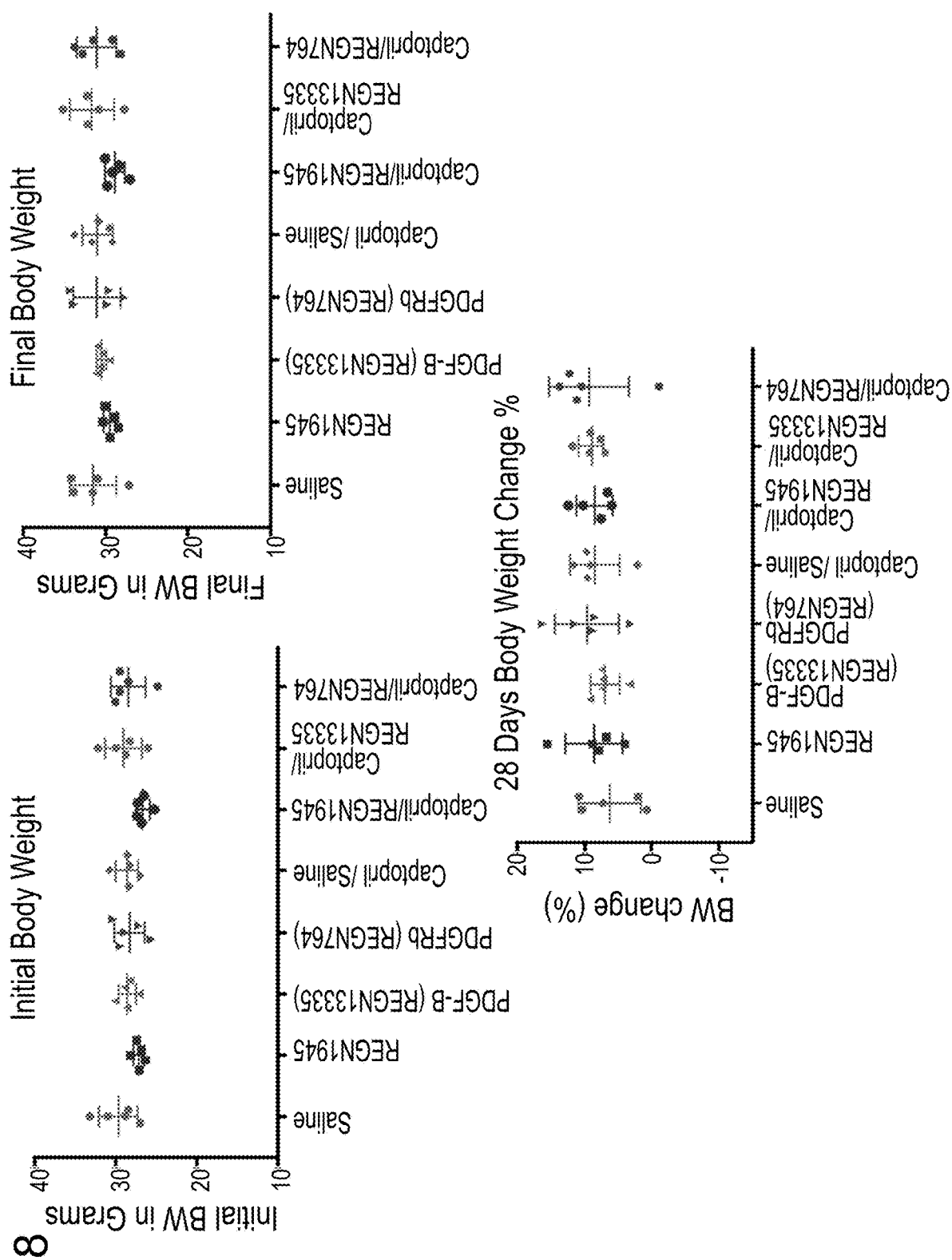
FIG. 18 is a panel of graphs depicting that dosing of anti-PDGF-B and anti-PDGFRβ antibodies did not significantly interfere with animal body weight gain.

FIG. 18 demonstrates that dosing of anti-PDGF-B and anti-PDGFRβ antibodies did not significantly interfere with animal body weight gain. Further no change was observed in animal behavior.

Figure 19:
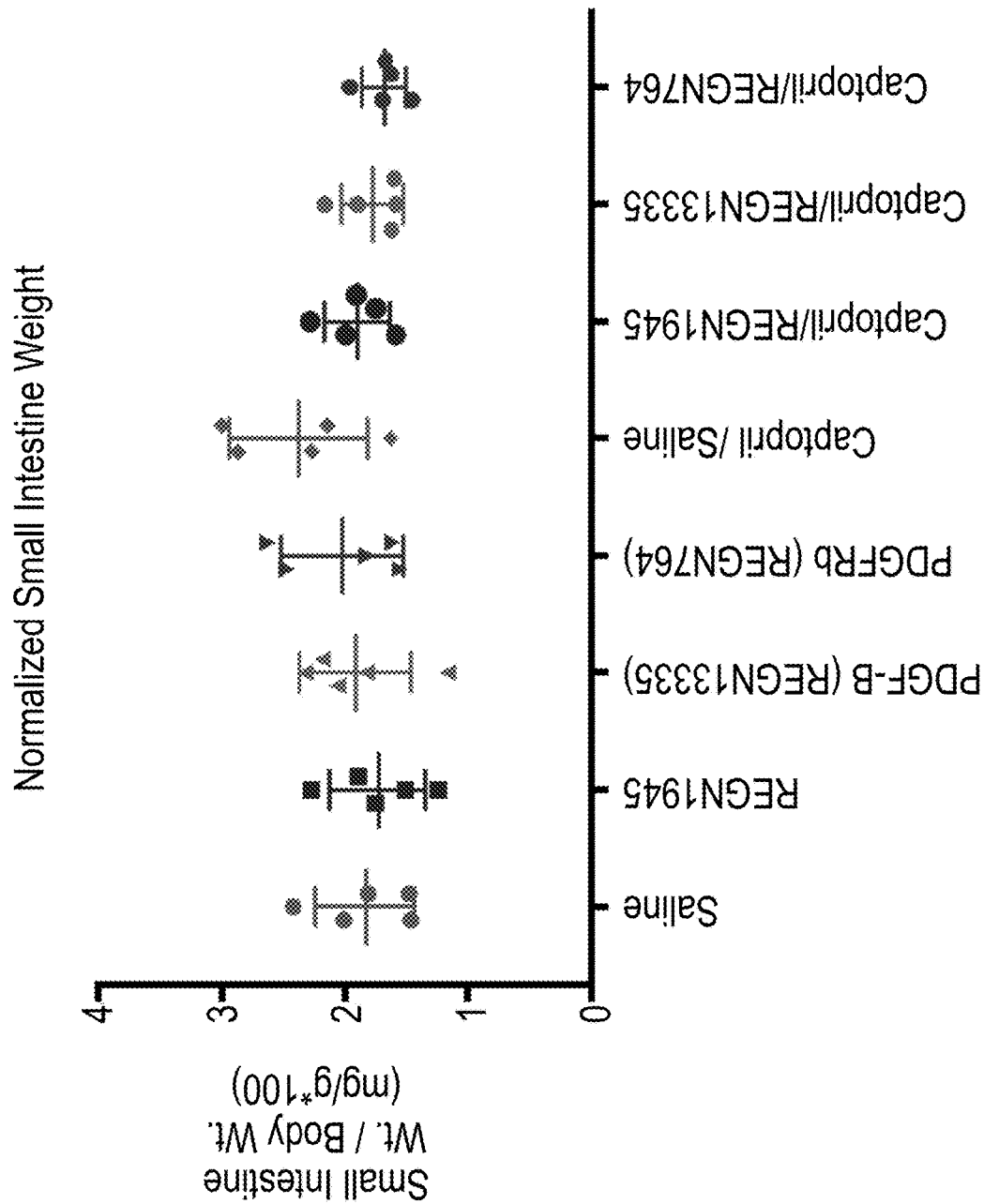
FIG. 19 is a graph depicting that there was no significant change in gastrointestinal (GI) fluid retention/edema in the small intestine after treatment with the isotype control IgG, anti-PDGF-B and anti-PDGFRβ antibodies in healthy mice.

Further, as demonstrated by FIG. 19, there was no significant change in GI fluid retention/edema in the small intestine after treatment with the Isotype control IgG, anti-PDGF-B and anti-PDGFRβ antibodies in healthy mice. Captopril caused mild and statistically insignificant gain of wet weight in the small intestine. Treatment of Isotype control IgG, anti-PDGF-B and anti-PDGFRβ antibodies did not significantly alter tissue edema in the small intestine caused by Captopril. Similarly, FIG. 20 demonstrates that there was no significant change in vessel permeability in the small intestine by treatment of anti-PDGF-B and anti-PDGFRβ antibodies in mice. The treatment of anti-PDGF-B and anti-PDGFRβ antibodies did not deteriorate Captopril caused acute vessel hyperpermeability in the small intestine.

Figure 21:
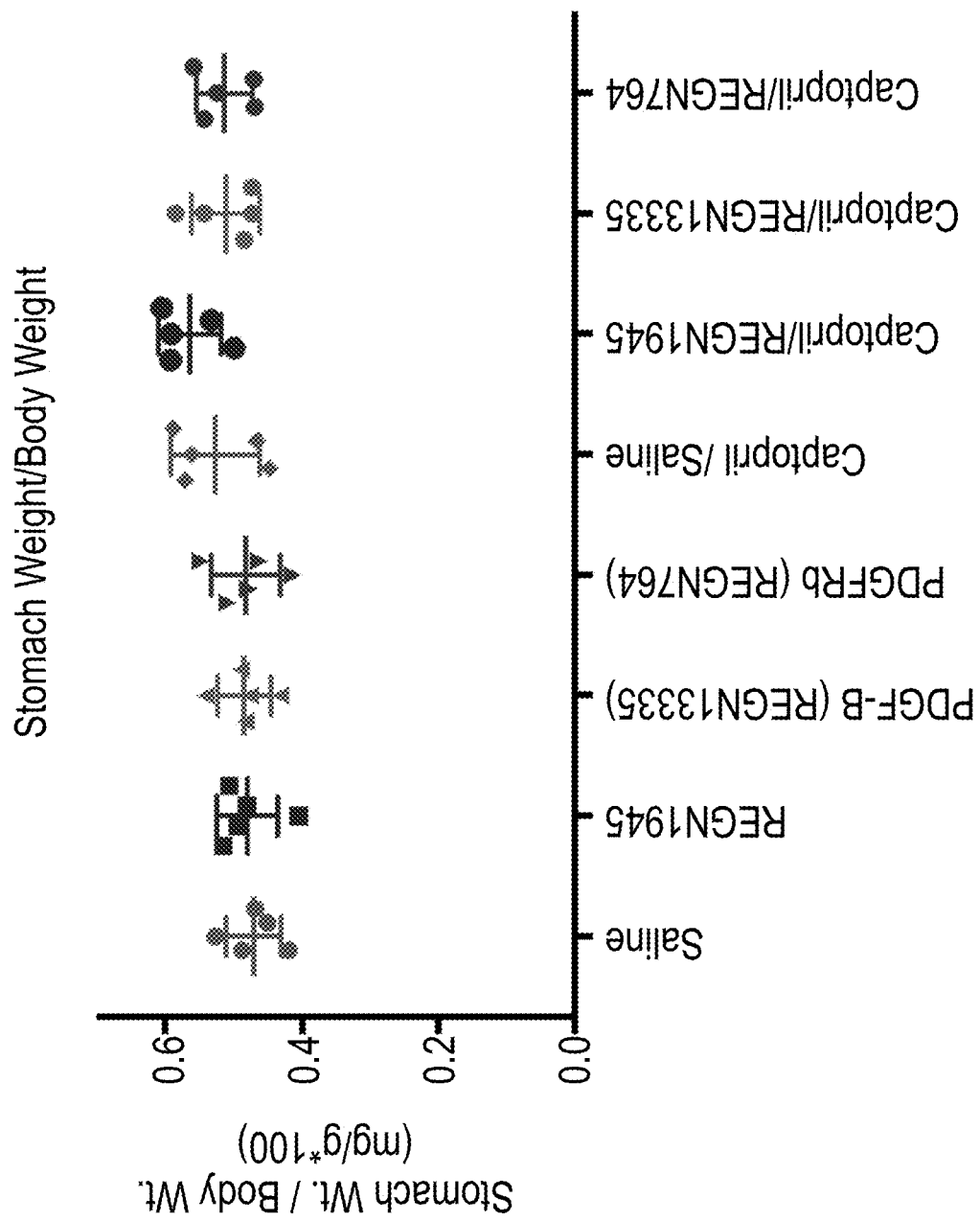
FIG. 21 is a graph depicting that there was no significant change in GI fluid retention/edema in the stomach by treatment of anti-PDGF-B and anti-PDGFRβ antibodies in healthy and Captopril treated mice.
Figure 22:
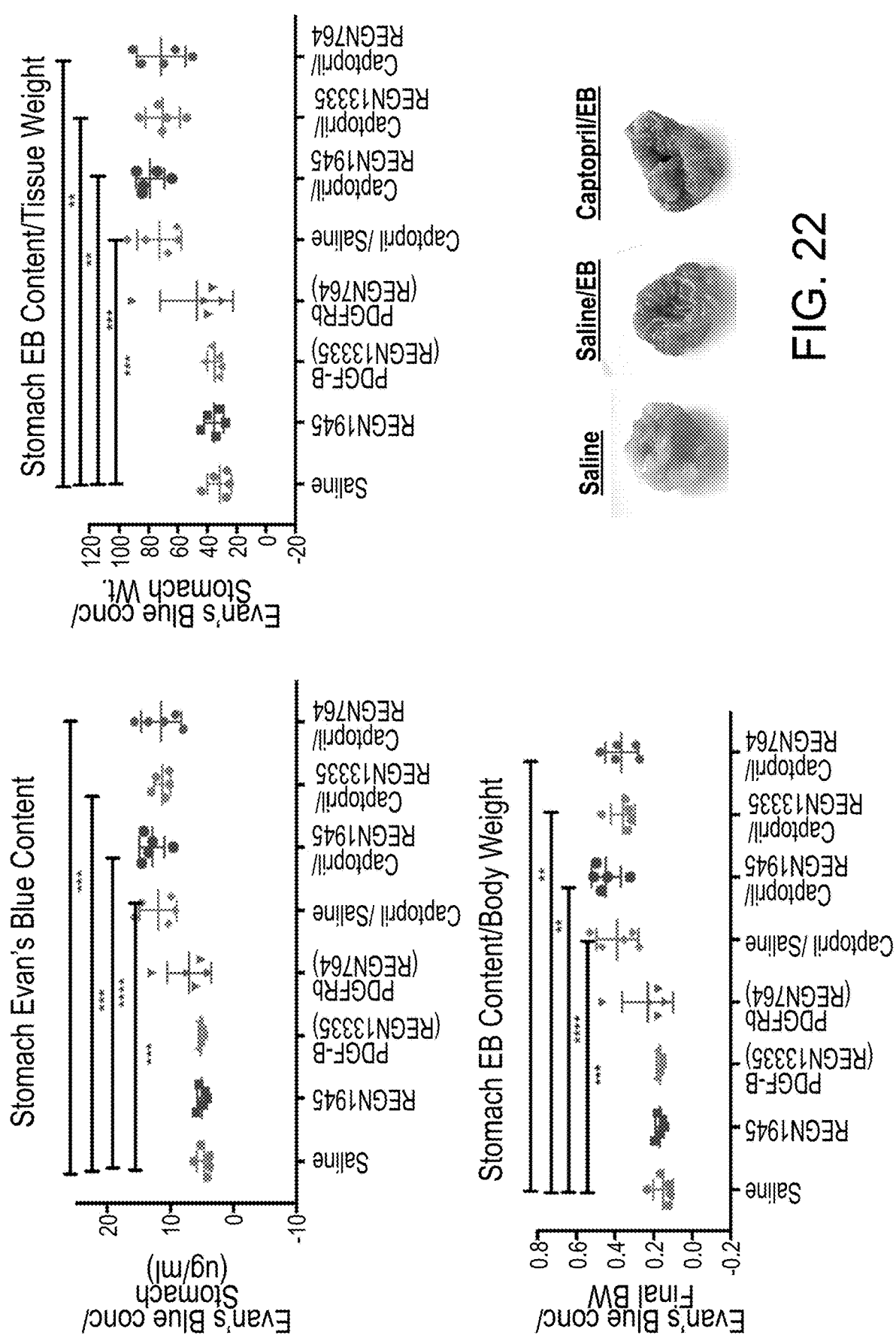
FIG. 22 is a panel of graphs and images depicting that there was no significant change in vessel permeability in the stomach by treatment of anti-PDGF-B and anti-PDGFRβ antibodies in mice.

Further, as demonstrated by FIG. 21, there was no significant change in GI fluid retention/edema in the stomach by treatment of anti-PDGF-B and anti-PDGFRβ antibodies in healthy and Captopril treated mice. Captopril did not cause statistically significant gain of wet weight in the stomach. Similarly, FIG. 22 shows that there was no significant change in vessel permeability in the stomach by treatment of anti-PDGF-B and anti-PDGFRβ antibodies in mice. The treatment of anti-PDGF-B and anti-PDGFRβ antibodies did not deteriorate Captopril caused acute vessel hyperpermeability in the stomach.

Figure 23:
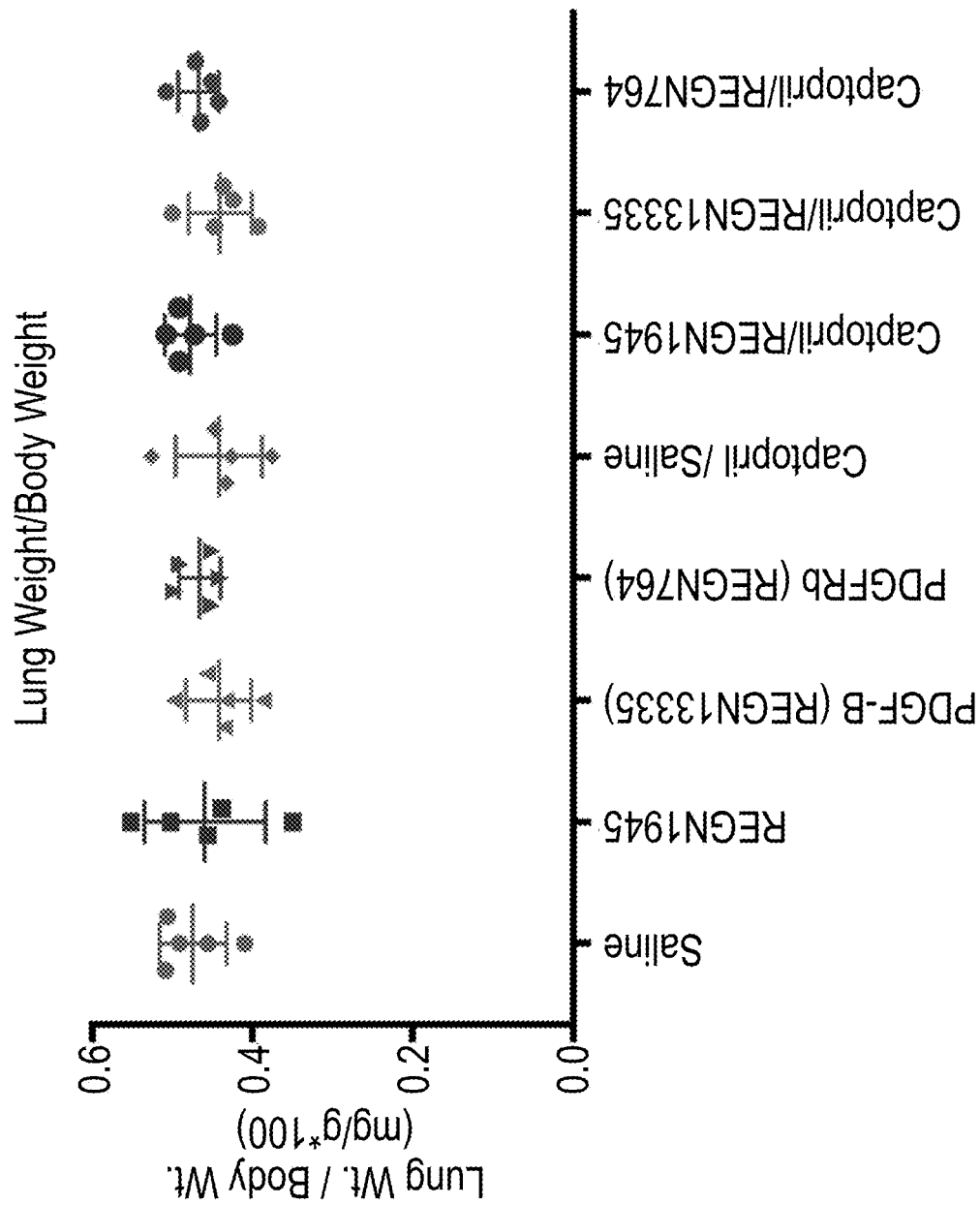
FIG. 23 is a graph depicting that there was no significant change in GI fluid retention/edema in the lung by treatment of anti-PDGF-B and anti-PDGFRβ antibodies in healthy and Captopril treated mice.
Figure 24:
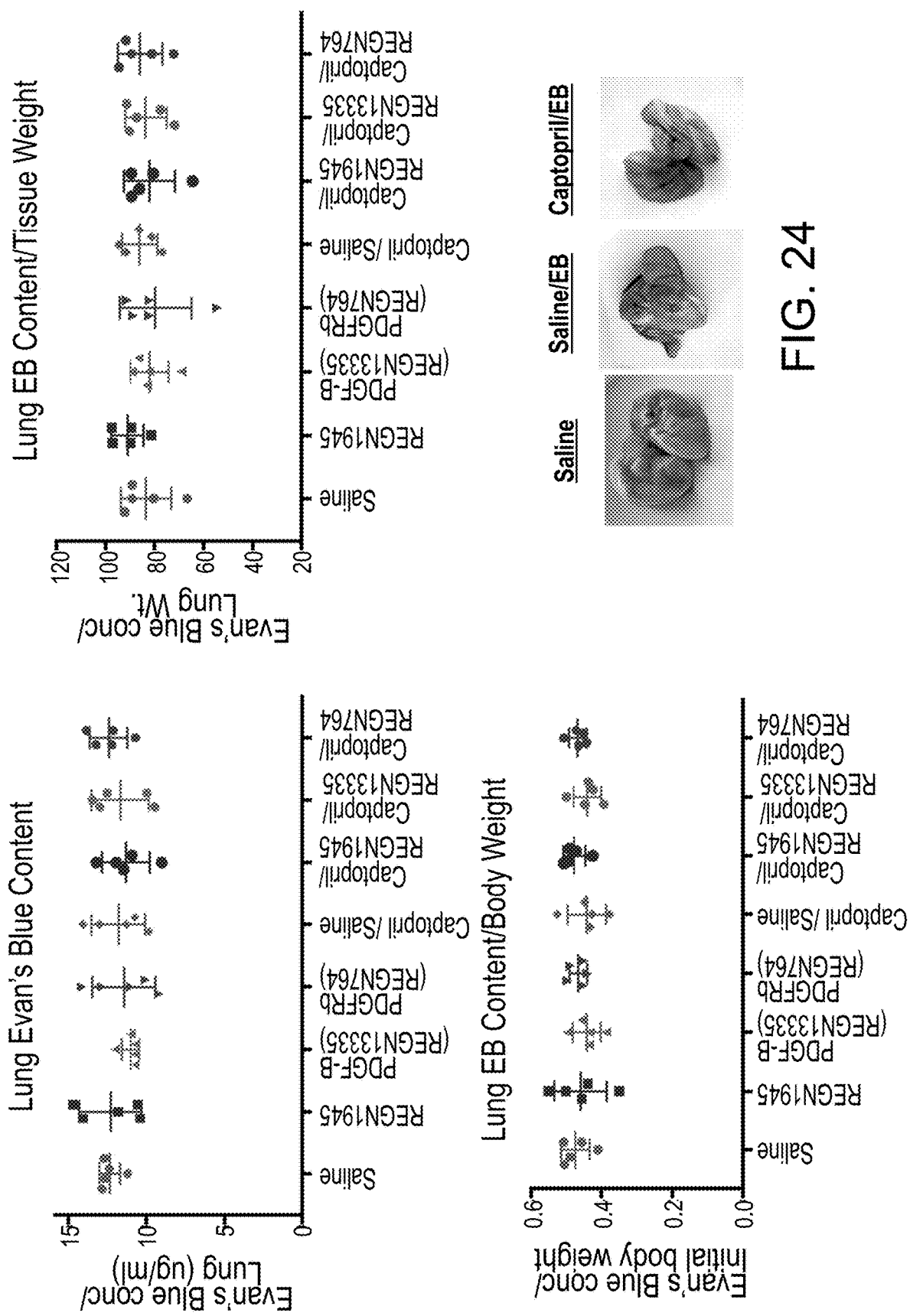
FIG. 24 is a panel of graphs and images depicting that there was no significant change in vessel permeability in the lung by treatment of anti-PDGF-B and anti-PDGFRβ antibodies in healthy and Captopril treated mice.

FIG. 23 presents results demonstrating that there was no significant change in GI fluid retention/edema in the lung by treatment of anti-PDGF-B and anti-PDGFRβ antibodies in healthy and Captopril treated mice. Captopril did not cause significant gain of weight in the lung. Similarly, as demonstrated by FIG. 24, there was no significant change in vessel permeability in the lung by treatment of anti-PDGF-B and anti-PDGFRβ antibodies in healthy and Captopril treated mice. Captopril acute treatment did not cause vessel hyperpermeability in the lung.

Figure 25:
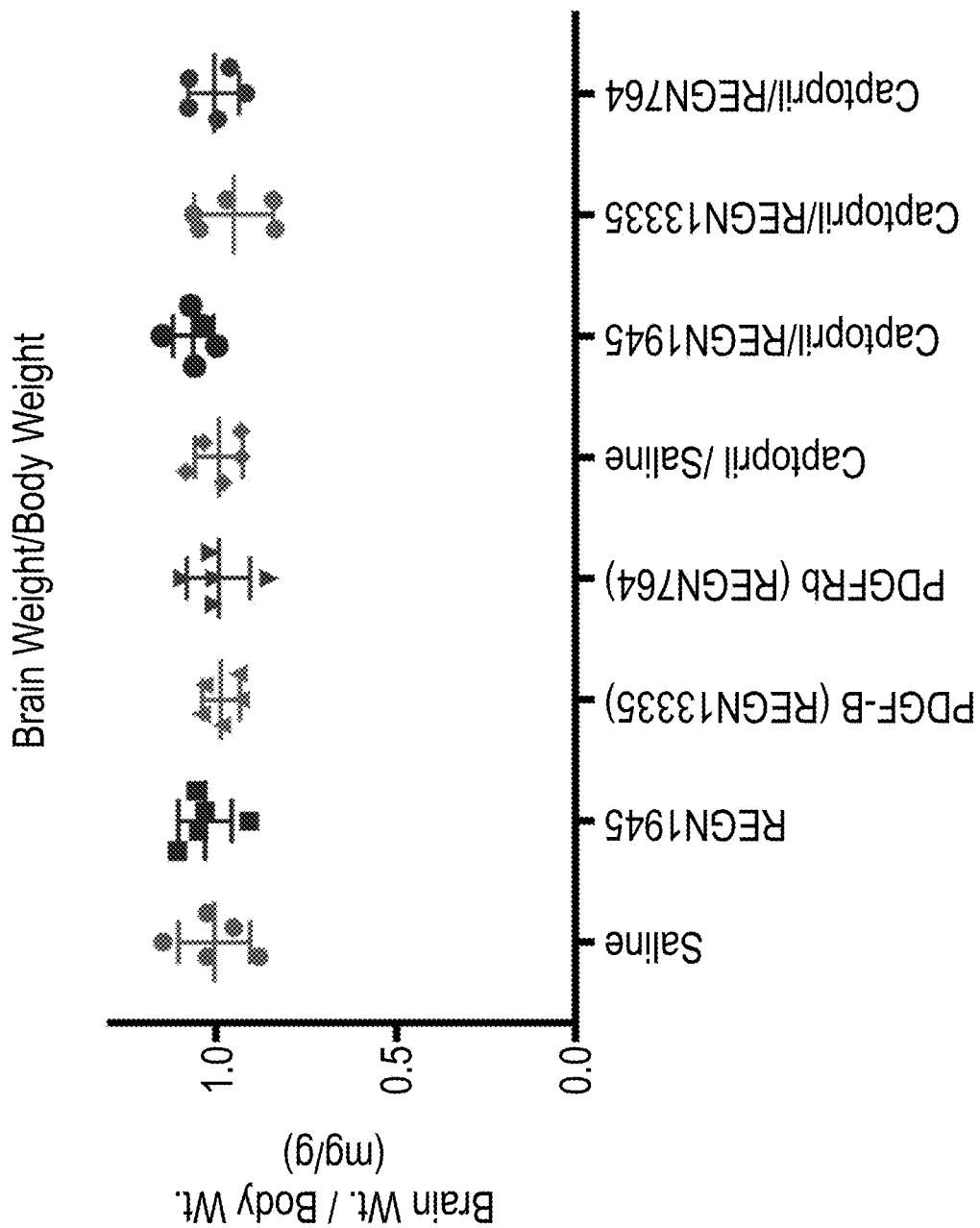
FIG. 25 is a graph depicting that there was no significant change in GI fluid retention/edema in the brain by treatment of anti-PDGF-B and anti-PDGFRβ antibodies in healthy and Captopril treated mice.

Further, FIG. 25 presents results demonstrating that there was no significant change in GI fluid retention/edema in the brain by treatment of anti-PDGF-B and anti-PDGFRβ antibodies in healthy and Captopril treated mice. Captopril did not cause significant gain of weight in the brain. Similarly, as demonstrated by FIG. 26, there was no significant change in vessel permeability in the brain by treatment of anti-PDGF-B and anti-PDGFRβ antibodies in healthy and Captopril treated mice. Captopril acute treatment did not cause vessel hyperpermeability in the brain.

Overall, treatment of anti-PDGF-B and anti-PDGFRβ antibodies did not cause any significant tissue edema and GI vessel permeability change in mice. Therefore, there is no negative impact of PDGF-B and PDGFRβ neutralizing antibodies in adult mice GI vessel permeability. Further, this study suggest that the PDGF-B signal might be dispensable in maintaining mice vasculature pericyte integrity.

Example 14. Biacore Binding Kinetics of PDGF-BB Monoclonal Antibody Binding to Human PDGF-BB, Monkey PDGF-BB and Rat PDGF-BB at 25° C.

The equilibrium dissociation constant ($K_D$) for PDGF-BB binding to different PDGF-BB monoclonal antibodies (mAbs) was determined using a real-time surface plasmon resonance biosensor using a Biacore T200 or MASS-2 instrument. All binding studies were performed in 10 mM HEPES, 300 mM NaCl, and 0.05% v/v Surfactant Tween-20, pH 7.4 (HBS-P) running buffer at 25° C. The sensor chip surface was first derivatized by amine coupling with human Fc specific mouse mAb (REGN2567) to capture different PDGF-BB mAbs. Different concentrations (90-1.11 nM, 3-fold serial dilution) of human PDGF-BB, monkey (*Macaca fascicularis*) PDGF-BB or rat PDGF-BB, prepared in HBS-P running buffer were injected over the anti-PDGF-BB mAb captured surface for 1-3 minutes at a flow rate of 25-50 μL/min and their dissociation in HBS-P running buffer was monitored for 5-10 minutes. At the end of each cycle, the PDGF-BB mAb captured surface was regenerated using a 10-12 seconds injection of 20 mM phosphoric acid.

The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2 \text{ (min)} = \frac{\ln(2)}{60*kd}$$

The binding kinetics parameters for PDGF-BB binding to different PDGF-BB mAbs of the invention at 25° C. are described in Tables 17-19.

Results

TABLE 17

Binding kinetics parameters of different PDGF-BB monoclonal antibodies (mAbs) binding to human PDGF-BB at 25° C.

| mAb Captured | mAb Capture Level (RU) | 15 nM hPDGF-BB Bound (RU) | $k_a$ (1/Ms) | $k_d$ (1/s) | $K_D$ (M) | t½ (min) |
|---|---|---|---|---|---|---|
| H4H13132P | 287.1 ± 1.1 | 49.9 | 3.01E+06 | 5.30E−05 | 1.76E−11 | 218 |
| H4H13145P | 170.9 ± 2.1 | 39.5 | 2.88E+06 | 1.00E−5* | 3.47E−12 | ≥1155 |

*Indicates that no dissociation of anti-PDGD-BB mAb was observed under the current experimental conditions and the value of kd was fixed at 1.00E−05.

TABLE 18

Binding kinetics parameters of different PDGF-BB monoclonal antibodies (mAbs) binding to monkey PDGF-BB at 25° C.

| mAb Captured | mAb Capture Level (RU) | 30 nM mfPDGF-BB Bound (RU) | $k_a$ (1/Ms) | $k_d$ (1/s) | $K_D$ (M) | $t^{1/2}$ (min) |
|---|---|---|---|---|---|---|
| H4H13132P | 257.6 ± 1.5 | 50.3 | 4.31E+06 | 4.17E−05 | 9.67E−12 | 277.2 |
| H4H13145P | 300.1 ± 13.5 | 73.4 | 9.30E+05 | 1.50E−05 | 1.61E−11 | 769.7 |

TABLE 19

Binding kinetics parameters of different PDGF-BB monoclonal antibodies (mAbs) binding to rat PDGF-BB at 25° C.

| mAb Captured | mAb Capture Level (RU) | 15 nM rPDGF-BB Bound (RU) | $k_a$ (1/Ms) | $k_d$ (1/s) | $K_D$ (M) | $t^{1/2}$ (min) |
|---|---|---|---|---|---|---|
| H4H13132P | 286.3 ± 0.1 | 42.7 | 2.75E+06 | 2.82E−04 | 1.03E−10 | 41.0 |
| H4H13145P | 167.3 ± 1.0 | 35.3 | 2.25E+06 | 2.82E−04 | 1.25E−10 | 40.9 |

Example 15. Testing for Antibody Inhibition of Human PDGF-BB, PDGF-AB, or the Combination of PDGF-BB/AB Induced Calcium Flux Using FLIPR with Primary Human Pulmonary Artery Smooth Muscle Cells and Primary Human Lung Fibroblasts For the calcium flux assay, primary Human Pulmonary Smooth Muscle Cells (Lonza, Cat #CC-2581) and Human Lung Fibroblasts (Lonza, Cat #2512) were seeded onto 96-well assay plates at a cell density of 10 k/well. The smooth muscle cells were cultured in supplier recommended smooth muscle media (Lonza, CC-3182) and the fibroblasts were cultured in DMEM-10% FBS-1× Penicillin/Streptomycin/L-Glutamine in a humidified incubator at 37° C. in 5% $CO_2$.

Upon reaching 100% confluency in the well, PDGF driven calcium flux was assessed via the FLIPR® Calcium 5 Assay Kit (Molecular Devices, Cat #R8185) on the FLIPR Tetra System (Molecular Devices) following the manufacturer's protocol. Briefly, complete media was replaced with 50 µL assay media (DMEM-0.1% BSA-1× Penicillin/Streptomycin/L-Glutamine). The Calcium 5 dye was then reconstituted in the supplied buffer in the presence of probenecid (Thermofisher, Cat #P36400). 50 µL of reconstituted Calcium 5 dye was then added to the cells and incubated for 1 hour at 37° C. in 5% $CO_2$ before being placed into the FLIPR Tetra System. Human PDGF-BB (R&D Systems, Cat #220-GMP), human PDGF-AB (R&D Systems, Cat #222-AB) and PDGF-AB/PDGF-BB were used in a 3:1 ratio to generate individual dosing plates. A 1 nM concentration of PDGF-AB, PDGF-BB and the combination treatment PDGF-AB/BB was chosen as a constant to assess antibody inhibition. In the presence of 1 nM PDGF proteins H4H13145P or H4H13132P, at a range of 500 nM to 0.06 nM (1:6 serial dilution), were tested. Antibodies were pre-incubated with PDGF proteins for 30-minutes before addition onto the cells via the FLIPR tetra system. Calcium flux traces were assessed at both 60 seconds and over the full-time course of 5 minutes. These calcium traces were analyzed for their Max-Min values using the SoftMax Pro Software (Molecular Devices).

As shown in Table 20, both antibodies, H4H13145P & H4H13132P, demonstrated complete inhibition of 1 nM PDGF-BB, PDGF-AB & PDGF-AB/BB (3:1) when recording calcium flux on human Pulmonary Smooth Muscle Cells for 60 seconds. Both antibodies demonstrated inhibition of 1 nM PDGF treatments with $IC_{50}$ values ranging from 0.18 nM to 4.5 nM. H4H13145P demonstrated greater potency than H4H13132P against PDGF-BB with an $IC_{50}$ of 0.18 nM and 0.64 nM respectively. These antibodies are more potent inhibitors of PDGF-BB alone than PDGF-AB and the PDGF-AB/BB (3:1) combination.

When recording calcium flux over a full-time course of 5 minutes, H4H13145P demonstrated a greater ability to neutralize PDGF-BB and prevent PDGF driven calcium flux compared to H4H13132P. H4H13145P maintained strong inhibition of all PDGF treatments with an $IC_{50}$ of 0.36 nM for PDGF-BB inhibition, 16 nM for PDGF-AB inhibition and 5.7 nM for the combination of PDGF-AB/BB (3:1). An isotype control antibody demonstrated no inhibition of PDGF mediated calcium flux.

TABLE 20

Anti-PDGF-BB antibody inhibition of PDGF-BB, AB, or AB/BB activation in primary cell-based assay (Pulmonary Artery Smooth Muscle Cells)

| PDGF Proteins | Human PDGF-BB | Human PDGF-AB | Human PDGF-AB/BB (3:1) |
|---|---|---|---|
| Cell Type | PASM Cells | PASM Cells | PASM Cells |
| $EC_{50}$ [M] | 3.80E−10 | 9.20E−10 | 6.00E−10 |
| Constant Concentration | 1 nM | 1 nM | 1 nM |

TABLE 20-continued

Anti-PDGF-BB antibody inhibition of PDGF-BB, AB, or AB/BB activation
in primary cell-based assay (Pulmonary Artery Smooth Muscle Cells)

| | IC$_{50}$ [M] | (%) Inhibition | IC$_{50}$ [M] | (%) Inhibition | IC$_{50}$ [M] | (%) Inhibition |
|---|---|---|---|---|---|---|
| 60 Second Timepoint | | | | | | |
| H4H13145P (45P) | 1.80E−10 | 96% | 1.50E−09 | 99% | 1.20E−09 | 99% |
| H4H13132P (32P) | 6.40E−10 | 96% | 2.10E−09 | 100% | 4.50E−09 | 100% |
| Isotype Control | No Inhibition | | No Inhibition | | No Inhibition | |
| Full Time Course | | | | | | |
| H4H13145P (45P) | 3.60E−10 | 97% | 1.10E−08 | 91% | 5.70E−09 | 89% |
| H4H13132P (32P) | 6.60E−09 | 92% | 1.20E−07 | 70% | 3.30E−07 | 72% |
| Isotype Control | No Inhibition | | No Inhibition | | No Inhibition | |

PASM—Human Pulmonary Artery Smooth Muscle Cells

When tested in Human Lung Fibroblasts, H4H13145P & H4H13132P demonstrated complete inhibition of all PDGF treatments when recording calcium flux over 60 seconds. Both antibodies demonstrated inhibition of 1 nM PDGF treatments with IC$_{50}$ values ranging from 0.59 nM to 1.6 nM. H4H13145P demonstrated slightly greater potency in neutralizing PDGF-BB compared to H4H13132P with an IC$_{50}$ of 0.59 nM and 0.99 nM respectively. H4H13145P was also slightly more potent in neutralizing the combination PDGF-AB/BB treatment than H4H13132P with an IC$_{50}$ value of 0.16 nM and 0.54 nM respectively. These antibodies are more potent inhibitors of PDGF-BB alone than PDGF-AB and the combination PDGF-AB/BB treatment.

When recording calcium flux over a full-time course of 5 minutes, H4H13145P demonstrated a significantly greater ability to neutralize PDGF-BB, PDGF-AB and the combination treatment PDGF-AB/BB compared to H4H13132P. H4H13132P demonstrated a lower ability to maximally inhibit the 1 nM constant of all PDGF treatments. H4H13145P showed greater potency in inhibiting PDGF-BB driven calcium flux compared to H4H13132P with an IC$_{50}$ of 0.63 nM and 3.8 nM respectively. An isotype control antibody demonstrated no inhibition of PDGF mediated calcium flux in Human Lung Fibroblasts.

Example 16: Structural Analysis of the Antibody-PDGF-BB Complex by Cryogenic Electron Microscopy (Cryo-EM)

Methods

Fab Fragment Preparation

H4H13145P, H4H13132P and H4H13127P IgGs were cleaved into F(ab')$^2$ and Fc fragments using Fabricator enzyme (Genovis) following standard protocols from the manufacturer. F(ab')$^2$ was reduced into Fab using 2-mercaptoethylamine (2-MEA, ThermoFisher) followed by Fc fragment removal using CaptureSelect IgG-Fc (ms) affinity resin (ThermoFisher). Fab fragments were further purified by injection into a size exclusion chromatography (SEC) column (Superdex 200 Increase 15/300 GL, GE healthcare) connected to an AKTA Avant 25 chromatography system (GE healthcare), running buffer contained 50 mM Tris-HCl pH 7.5, 150 mM NaCl. Peak fractions were pooled and concentrated in a 30 kDa cutoff centrifugal filter (Millipore Sigma) for subsequent use in complex preparation.

Complex Preparation

Recombinant human PDGF-BB protein (R&D) was mixed with H4H13145P Fab or H4H13132P Fab at 1:2.2 molar ratio. Excess non-competing H4H13127P Fab was

TABLE 21

Anti-PDGF-BB antibody inhibition of PDGF-BB, AB, or AB/BB
activation in primary cell-based assay (Fibroblasts)

| PDGF Proteins | Human PDGF-BB | Human PDGF-AB | Human PDGF-AB/BB (3:1) |
|---|---|---|---|
| Cell Type | HLF Cells | HLF Cells | HLF Cells |
| EC$_{50}$ [M] | 2.40E−10 | 6.50E−10 | 5.50E−10 |
| Constant Concentration | 1 nM | 1 nM | 1 nM |

| | IC$_{50}$ [M] | (%) Inhibition | IC$_{50}$ [M] | (%) Inhibition | IC$_{50}$ [M] | (%) Inhibition |
|---|---|---|---|---|---|---|
| 60 Second Timepoint | | | | | | |
| H4H13145P (45P) | 5.90E−10 | 100% | 1.00E−09 | 100% | 1.60E−10 | 100% |
| H4H13132P (32P) | 9.90E−10 | 100% | 1.60E−09 | 100% | 5.40E−10 | 100% |
| Isotype Control | No Inhibition | | No Inhibition | | No Inhibition | |
| Full Time Course | | | | | | |
| H4H13145P (45P) | 6.30E−10 | 100% | 2.10E−08 | 100% | 1.10E−09 | 100% |
| H4H13132P (32P) | 3.80E−09 | 97% | 4.30E−07 | 63% | 5.50E−09 | 87% |
| Isotype Control | No Inhibition | | No Inhibition | | No Inhibition | | further added to the two samples to increase the size of the two complexes, making them more suitable targets for EM characterization. This additional Fab is also able to improve orientation distribution of the complex particles on EM grids. The samples were incubated at 4° C. for 30 minutes before being concentrated in a 30 kDa cutoff centrifugal filter (Millipore Sigma) to a concentration of 2.5 mg/mL measured using a Nanodrop instrument (ThermoFisher).

Cryo-EM Sample Preparation and Data Collection

Freshly made PDGFBB—H4H13145P Fab—H4H13127 Fab complex or PDGFBB—H4H13132P Fab—H4H13127 Fab complex was mixed with ~0.15% Amphipol PMAL-C8 (Anatrace) immediately before pipetting 3.5 µL of the mixture onto a UltrAufoil R1.2/1.3, 300 mesh grid (Quantifoil). Excess liquid was blotted away using filter paper and the grid was plunge frozen into liquid ethane cooled by liquid nitrogen using a Vitrobot Mark IV (ThermoFisher) operated at 4° C. and 100% humidity. The grid was then loaded into a Titan Krios G3i microscope (ThermoFisher) equipped with a K3 camera (Gatan). ~7,000 movies were collected in counted mode at a nominal magnification of 105,000× (0.86 Å pixel size) for both complexes with the EPU software (ThermoFisher). Each movie contained 46 dose fractions over a 2 second exposure, and the total acquired dose per $A^2$ was ~40 electrons.

Cryo-EM Data Processing and Map Generation

Cryo-EM data were processed using Cryosparc v2.14.2. Movies were motion corrected by Patch motion correction and CTF parameters were estimated by Patch CTF estimation. Particles were initially picked using Blob picker to generate 2D class averages to be used as templates for the subsequent template picking. After multiple rounds of 2D classification to remove junk particles, 249,832 and 429,948 particles were left for PDGFBB—H4H13145P Fab—H4H13127 Fab complex and PDGFBB—H4H13132P Fab—H4H13127 Fab complex, respectively. Through Ab initio reconstruction, Homogeneous refinement and Heterogenous refinement, 110,261 particles corresponding to the PDGFBB—H4H13145P Fab—H4H13127 Fab complex, and 159,372 particles corresponding to the PDGFBB—H4H13132P Fab—H4H13127 Fab complex were identified. Using Non-uniform refinement, these particles were further refined to 3.4 Å and 3.5 Å resolution reconstructions for the two complexes, respectively.

Model Building and Refinement

Manual model building was carried out using Coot version 0.8.9 and real space refinements were done in Phenix version 1.17. The crystal structure of human PDGF-BB (PDB: 1PDG) was docked into the cryo-EM density maps of PDGFBB—H4H13145P Fab—H4H13127 Fab complex and PDGFBB—H4H13132P Fab—H4H13127 Fab complex using UCSF Chimera Fit-in-map. Homology models for Fab fragments of H4H13145P, H4H13132P and H4H13127P were made from a previously determined REGN Fab structure. Unambiguous docking of Fab models into their respective densities was aided by clearly interpretable side chain densities corresponding to their distinct CDR sequences. After docking, the models were adjusted manually in Coot followed by real space refinement of the entire PDGFBB—H4H13145P Fab—H4H13127 Fab complex or PDGFBB—H4H13132P Fab—H4H13127 Fab complex in Phenix.

Results

The PDGFBB ligand is a homodimer containing two clamp regions formed by three inter-strand loops (L1 formed by residues 25-38, L2 formed by residues 53-58, and L3 formed by residues 78-81), followed by C-terminal segments.

According to cryo-EM studies, each PDGFBB homodimer binds to two H4H13145P or H4H13132P Fab molecules, and two H4H13127P Fab molecules. The two complexes both have 2-fold symmetry with two H4H13127P Fab molecules binding to the outside edge of the β-sheet region. H4H13145P Fab and H4H13132P Fab both bind to the three interstrand loops, which also engages with PDGFRβ in the PDGFBB—PDGFRβ signaling complex (PDB: 3MJG), with similar binding site. The data suggests that the H4H13145P and H4H13132P antibodies bind at the ends of the PDGFBB dimer, and a single Fab makes contacts with both monomers in the dimer, i.e., the antibody binds across the dimer interface.

H4H13145P: Both the heavy chain and the light chain of H4H13145P interact with the PDGFBB dimer at the three interstrand loops.

Antibody to dimer interactions: CDRs H1, H2 and H3 in the heavy chain (residues A31, Y32, W50, Y54, N57, W100) are involved in interactions with both chains of the PDGFBB homodimer. CDRs L3 in the light chain (residues Y91, Y92, N93, L94 and F96) are involved in interactions with chain 1 of the PDGFBB dimer.

Dimer to antibody interactions: Chain 1 of PDGFBB (residues F37, W40, R73, K80, K81, P82, F84, and K86) interacts with both chains of H4H13145P. Residues 113 and R56 in Chain 2 of PDGFBB are involved in interactions with the heavy chain of H4H13145P. Loop 1 and Loop 3 in Chain 1 play a major role in the interactions.

H4H13132P: Both the heavy chain and the light chain of H4H13132P interact with the PDGFBB dimer at the three inter-strand loops.

Antibody to dimer interactions: CDRs H1, H2 and H3 in the heavy chain (residues S31, A33, I52, I54, F55, D103, Y104, Y105) are involved in interactions with both chains of the PDGFBB dimer. CDRs L1 and L3 in the light chain (residues Y31, T97, and W99) are involved in interactions with chain1 of the PDGFBB dimer.

Dimer to antibody interactions: Chain 1 of PDGFBB (residues L38, W40, R73, I75, K80, K81, P82, I83, F84, and K86) interacts with both chains of H4H13132P. Residue R56 in Chain 2 of PDGFBB are involved in interactions with the heavy chain of H4H13132P. Loop 1 and Loop 3 in Chain 1 play a major role in the interactions Discussion Cryo-EM data shows that the two antibodies, H4H13145P and H4H13132P, have nearly identical binding sites on the PDGFBB dimer. Multiple residues within Chain 1 of PDGFBB interact with both antibodies (W40, R73, K80, K81, P82, F84, and K86). Interactions between Chain 2 of PDGFBB and the antibodies are fewer (two for H4H13145P and one for H4H13132P), yet both interactions have the R56 residue in common.

Example 17: Testing for Antibody or Small Molecule Inhibition of Human PDGF-BB, PDGF-AA, or PDGF-DD Induced Calcium Flux Using FLIPR or Cellular Proliferation in Primary Human Pulmonary Artery Smooth Muscle Cells Reagents The reagents used for testing for antibody or small molecule inhibition of human PDGF-BB, PDGF-AA, or PDGF-DD induced calcium flux using FLIPR or cellular proliferation in primary human pulmonary artery smooth muscle cells included: Human Pulmonary Artery Smooth Muscle Cells (PASMC), Lonza Cat #CC-2581 Lot #0000559495; Smooth Muscle Cell Media, Lonza, CC-3182; DMEM Media, Thermofisher, Cat #11965092; Bovine Serum Albumin solution, Millipore-Sigma, Cat #A9576; PDGF-BB, R&D Systems, Cat #220-GMP; PDGF-AA, R&D Systems, Cat #221-AA; PDGF-DD, R&D Systems, Cat #1159-SB; Calcium 5 Assay Kit, Molecular Devices, Cat #R8185; Probenecid, Thermofisher, Cat #P36400; Seralutinib (GB002), MedChemExpress, Cat #HY-109190; and Imatinib Mesylate, MedChemExpress, Cat #HY-50946.

Experimental Procedures

For calcium flux and proliferation assays, primary Human Pulmonary Smooth Muscle Cells were seeded onto 96-well assay plates at a cell density of 10,000/well and 2,000/well respectively. The smooth muscle cells were cultured in supplier recommended smooth muscle media in a humidified incubator at 37° C. in 5% $CO_2$.

Upon reaching 100% confluency within each well, PDGF driven calcium flux was assessed via the FLIPR® Calcium 5 Assay Kit on the FLIPR Tetra System (Molecular Devices) following the manufacturer's protocol. In brief, complete media was replaced with 50 μL assay media (DMEM-0.1% BSA-1× Penicillin/Streptomycin/L-Glutamine). The Calcium 5 dye was then reconstituted in the supplied buffer in the presence of probenecid. 50 μL of reconstituted Calcium 5 dye was then added to the cells and incubated for 1 hour at 37° C. in 5% $CO_2$ before being placed into the FLIPR Tetra System. Human PDGF-AA, PDGF-BB and PDGF-DD serial dilutions and inhibitory constants were generated on separate dosing plates. A 0.5 nM concentration of PDGF-BB, 1 nM concentration of PDGF-DD and a 3 nM concentration of PDGF-AA were chosen as constants to assess antibody and small molecule inhibition. A serial dilution of H4H13145P (anti-PDGFb) and H4H1238N (isotype control) (250 nM to 0.2 nM, 1:6 dilution) were tested in the presence of the PDGF constants. Antibodies were pre-incubated with PDGF proteins for 30 minutes before addition onto the cells via the FLIPR tetra system. The small molecules Seralutinib and Imatinib were pre-incubated for 30-minutes with the cells in assay media and calcium dye in a concentration range of 10,000 nM to 8 nM (1:6 serial dilution). These calcium traces were analyzed for their Max-Min values using the SoftMax Pro Software (Molecular Devices).

Proliferation was assessed via the IncuCyte live cell imaging system (Essen BioScience). Following overnight plating, the complete media was replaced with serum free smooth muscle media supplemented with 0.1% BSA. Antibodies were pre-incubated with PDGF constants for 30 minutes while the cells were pre-treated with the small molecule compounds Imatinib and Seralutinib before PDGF addition. Plates were imaged every 3 hours over the course of 7 days and proliferation was determined by measuring cell confluence in the well at day 6 via the IncuCyte Base Analysis software (Sartorius).

Results

The PDGF growth factor family are a set of potent mitogens that are of interest in pulmonary arterial hypertension. Multiple therapeutics, including small molecule receptor kinase inhibitors named Seralutinib and Imatinib, target the PDGF/PDGFR signaling pathway. In the present study, the anti-PDGF-BB molecule H4H13145P was directly compared to these small molecule PDGFR inhibitors in two in vitro cell assays.

Figure 27:
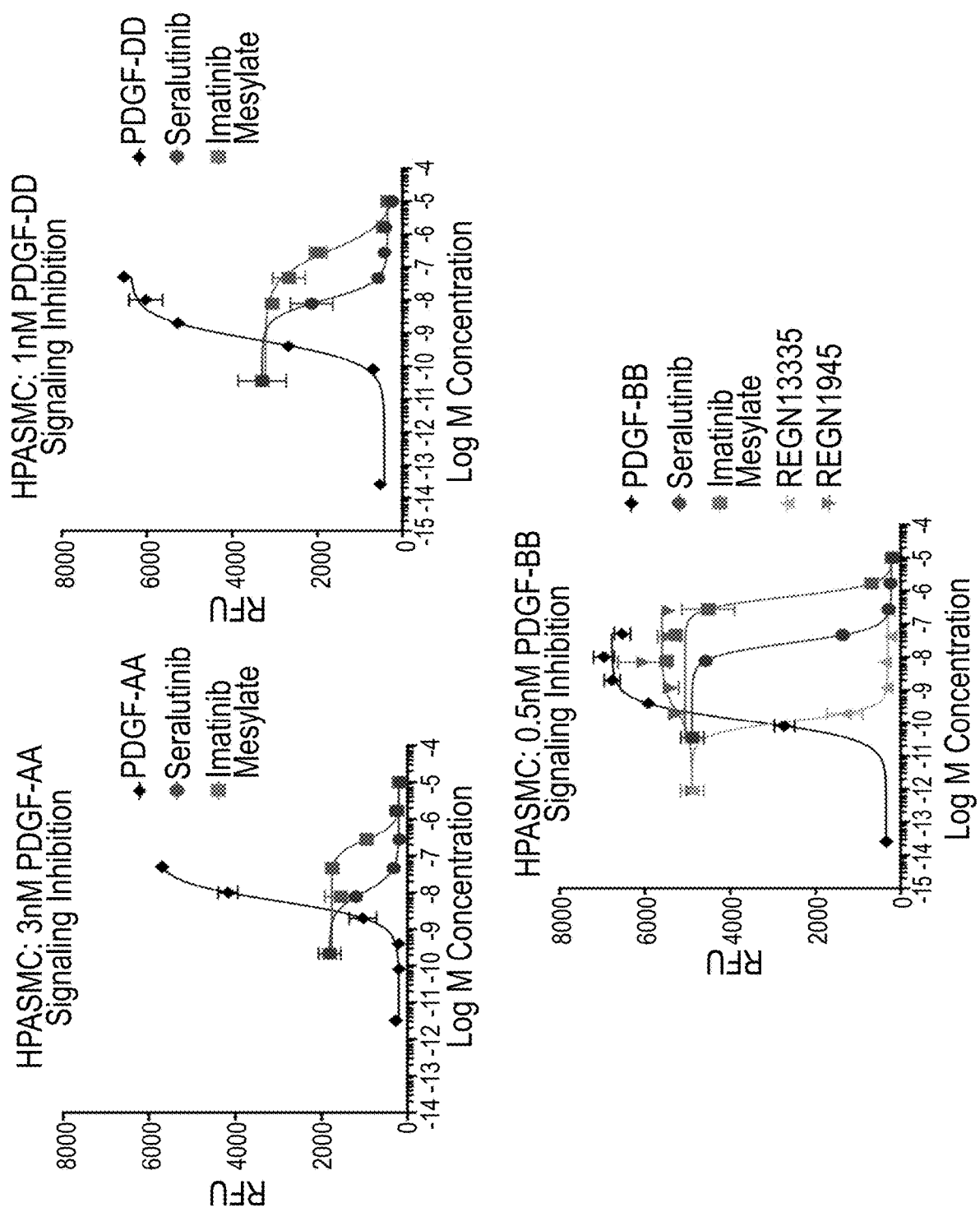
FIG. 27 is a panel of graphs depicting the inhibition of PDGF induced calcium flux in human pulmonary artery smooth muscle cells (HPASMC) by anti-PDGF-B antibodies.
Figure 28:
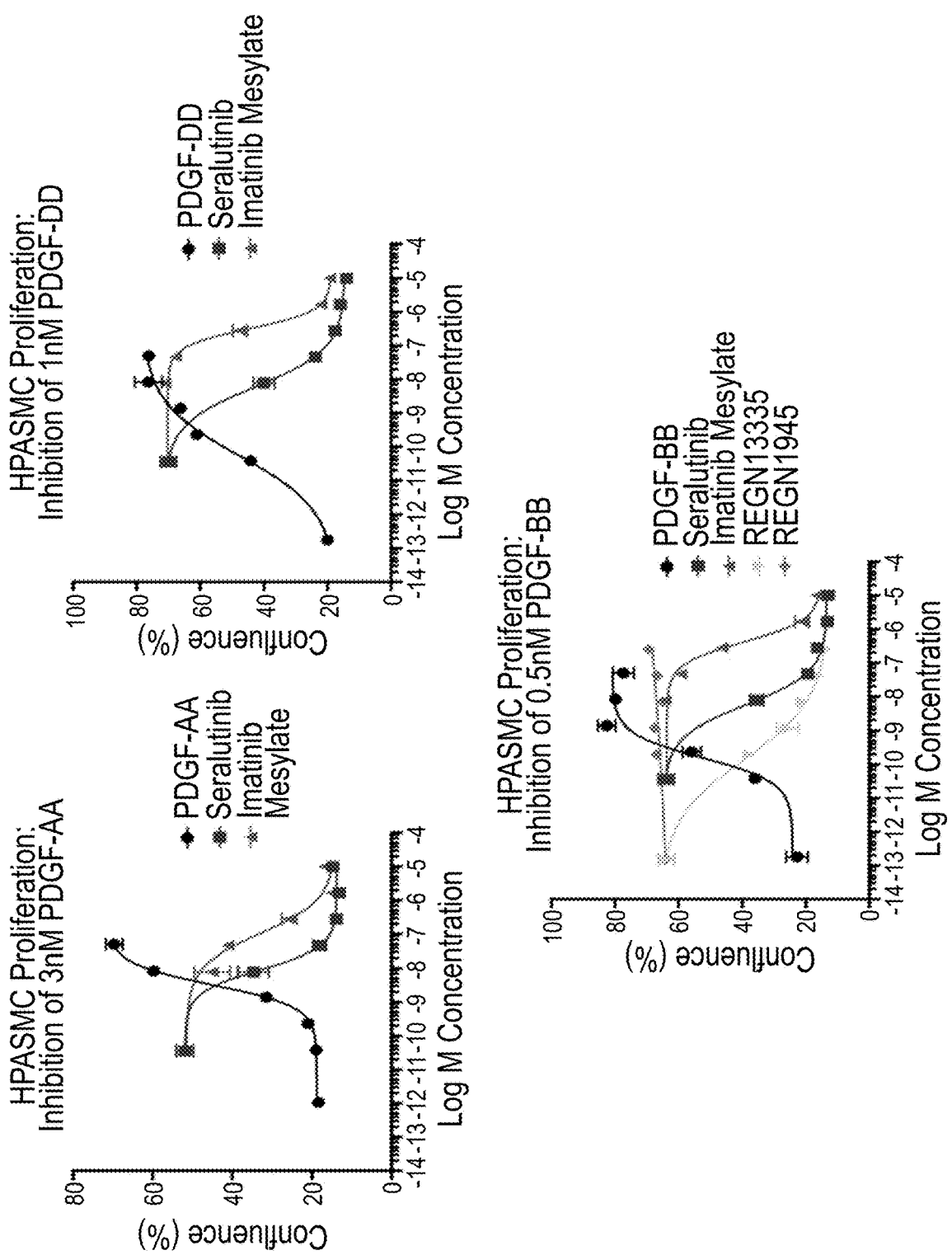
FIG. 28 is a panel of graphs depicting the inhibition of PDGF induced cellular proliferation in human pulmonary artery smooth muscle cells (HPASMC) by anti-PDGF-B antibodies.

Both Seralutinib and Imatinib fully inhibited PDGF-AA, PDGF-DD and PDFD-BB driven calcium flux and proliferation. PDGF-AA signals through PDGFRa, PDGF-DD signals through PDGFRb, and PDGF-BB signals through both dimeric receptors. As shown in Table 22, Seralutinib is more potent when compared to Imatinib in this cell-based assay with $IC_{50}$ values ranging from 6-27 nM. Imatinib was able to fully inhibit PDGF signaling with $IC_{50}$ values ranging from 110-650 nM. H4H13145P was able to fully inhibit PDGF-BB driven calcium flux and proliferation with an $IC_{50}$ of 0.11 nM and 0.14 nM respectively. H4H13145P is more potent against PDGF-BB when compared to the small molecule PDGFR inhibitors, Seralutinib and Imatinib (Table 22 and FIGS. 27-28).

TABLE 22

Summarized $IC_{50}$ across the in vitro assays.

| $IC_{50}$ | Seralutinib | | | Imatinib | | | H4H13145P |
|---|---|---|---|---|---|---|---|
| Protein | PDGF-AA | PDGF-DD | PDGF-BB | PDGF-AA | PDGF-DD | PDGF-BB | PDGF-BB |
| Calcium Flux | 10 nM | 27 nM | 10 nM | 270 nM | 660 nM | 330 nM | 0.110 nM |
| Proliferation | 9 nM | 6 nM | 6 nM | 110 nM | 320 nM | 410 nM | 0.140 nM |

Example 18: Testing for Receptor Mediated Antibody Internalization in Primary Human Pulmonary Artery Smooth Muscle Cells and Primary Human Lung Fibroblasts Reagents The reagents used for testing for receptor mediated antibody internalization in primary human pulmonary artery smooth muscle cells and primary human lung fibroblasts included: Human Pulmonary Artery Smooth Muscle Cells (PASMC), Lonza Cat #CC-2581 Lot #0000559495; Normal Human Lung Fibroblasts (NHLF) Lonza Cat #CC-2512 Lot #0000494609; DMEM Media, Thermofisher, Cat #11965092; Bovine Serum Albumin solution, Millipore-Sigma, Cat #A9576; Smooth Muscle Cell Media, Lonza, CC-3182; pHrodoTMDeep Red Antibody labeling kit cat #P35355 Thermo Fisher; CellTrkr™ Violet Cell proliferation kit Cat #C34571 Thermo Fisher; PDGF-BB—R&D Systems, Cat #220-GMP; PDGF-AB—R&D Systems, Cat #222-AB; Calcium 5 Assay Kit, Molecular Devices, Cat #R8185; Probenecid, Thermofisher, Cat #P36400; PDGFRa-APC, Abcam, Cat #AB119838; PDGFRb-APC, R&D Systems, Cat #FAB1263A; Isotype Antibody-APC, Abcam, Cat #AB37391; DAPI Viability Dye, Thermofisher, Cat #62248; and TrypLE™ Express Enzyme, Thermofisher, Cat #12604013.

Experimental Procedures

Antibody Labeling: pHrodo Deep Red Antibody labeling was completed by following the user guide provided by Invitrogen pHrodoTMDeep Red Antibody labeling kit (Catalog Numbers P35355 and P35356). The antibody internalization assays were performed using the following procedures:

Antibody Internalization Assay 1: (1) Plate 20,000 PASMC per well of a 96-well plate and incubate the cells in complete media overnight at 37° C., 5% $CO_2$, (2) Remove the complete culture media, wash once with PBS, then label the cells with CellTrkr Violet dye for 15 minutes; (3) Remove the CellTrkr solution; (4) Prebind labeled (pHrodo) anti-PDGF-B mAbs with PDGF-BB or PDGF-AB for 30 minutes at room temperature before treatment of cells; (5) Add the antibody-ligand solutions to the cells. No pre-binding as control; (6) Live-cell imaging was acquired every hour on Opera Phenix Imaging System for up to 21 hours; and (7) Analysis of data with Harmony 4.9 software.

Antibody Internalization Assay 2 (with receptor blocking): (1) Plate 20,000 PASMC per well of a 96-well plate and incubate the cells in complete media overnight at 37° C., 5% $CO_2$; (2) Remove the complete culture media, wash once with PBS, then label the cells with CellTrkr Violet dye for 15 minutes; (3) Remove the CellTrkr solution; (4) Add anti-PDGFRα (REGN1574), anti PDGFRβ (REGN764) at 500 nM each or in combination to the cells for 30 minutes; (5) Pre-bind labeled (pHrodo) anti-PDGF-B mAbs each with PDGF-BB or PDGF-AB for 30 minutes at room temperature before treatment of cells; (6) Add the antibody-ligand solutions to the cells; (7) Live-cell imaging was acquired every hour on Opera Phenix Imaging System for up to 72 hours; and (8) Analysis of data with Harmony 4.9 software.

FLIPR (Fluorescence Imaging Plate Reader) antibody internalization assay: (1) Plate 10,000 PASMC per well of a 96-well plate and incubate the cells in complete media overnight at 37° C., 5% $CO_2$, (2) Pre-incubate a mixture of antibody to PDGF-BB in a 10-1 nM ratio for 10 minutes in assay media (DMEM-0.1% BSA-1× Penicillin/Streptomycin/L-Glutamine); (3) Replace complete media with the 10-1 nM ratio of REGN1945 and H4H13145P to PDGF-BB; (4) Treat cells with the antibody-ligand mixture for 3, 24 and 48 hours; (5) Wash cell monolayer 3× with PBS; (6) Add 50 uL of assay media and 50 uL of the calcium 5 dye; (7) Incubate plate for 1 hour post-dye addition before plate reading via the FLIPR Tetra imager; (8) Assembled and have a treatment plate inserted into the FLIPR system to treat the cells with a serial dilution of PDGF-BB (25-0.04 nM, 1:6 Dilution); and (9) Analyze calcium traces for their Max-Min values using the SoftMax Pro Software (Molecular Devices)

Flow Cytometry antibody internalization assay: (1) Plate 300,000 PASMC per well of a 6-well plate and incubate the cells in complete media overnight at 37° C., 5% $CO_2$; (2) Pre-incubate a mixture of antibody to PDGF-BB in a 10-1 nM ratio for 10 minutes in assay media (DMEM-0.1% BSA-lx Penicillin/Streptomycin/L-Glutamine); (3) Replace complete media with the 10-1 nM ratio of antibodies to PDGF-BB; (4) Treat cells with the antibody-ligand mixture for 24 hours; (5) Wash cell monolayer 3× with PBS; (6) Dissociate cells from the 6 well plate using the TrypLE™ Express Enzyme; (7) Spin down and resuspend in cell staining buffer (10% DMEM, 5% FBS); (8) Stain cells on ice with APC conjugated antibodies against PDGFRa and PDGFRb for 1 hour following the manufacturer's protocol; (9) Spin and wash cells 3×; (10) Prior to insertion in the CytoFlex flow cytometer, add the DAPI viability dye to the cells at a final concentration of 1 μg/mL; (11) Record 10,000 cells on the CytoFlex flow cytometer with gating for live single cells; and (12) Analyze the flow cytometer data on the FlowJo software (BD Biosciences).

Results

Across multiple separate assays it was shown that H4H13145P can be internalized into various cell lines in a ligand dependent manner through the PDGF receptors.

Antibody Internalization: Labeling the anti-PDGF-B antibodies with pHrodo Deep Red allowed for the evaluation of antibody internalization in human primary PASMC assay. The pHrodo Deep Red emits light at pH levels that are encountered in the late endosome or lysosome. At normal pH, no light is emitted. This allows for evaluation of time dependent internalization using confocal imaging. As shown in Tables 23-24, labeled H4H13145P-PDGFBB co-treatment had a 108-127× fold change increase in fluorescent signal compared to the labeled isotype control REGN1945 in both PASMC and NHLF. A similar trend is observed at a lower magnitude for PDGF-AB. This increase in fluorescent signal, which is only emitted once the labeled antibodies are internalized into the cell, is diminished when the cells have been pre-treated with two antibodies that inhibit both the PDGFRa and PDGFRb receptor. This data suggests that H4H13145P is internalized into the cell in a ligand dependent manner through the PDGF receptors.

Figure 29:
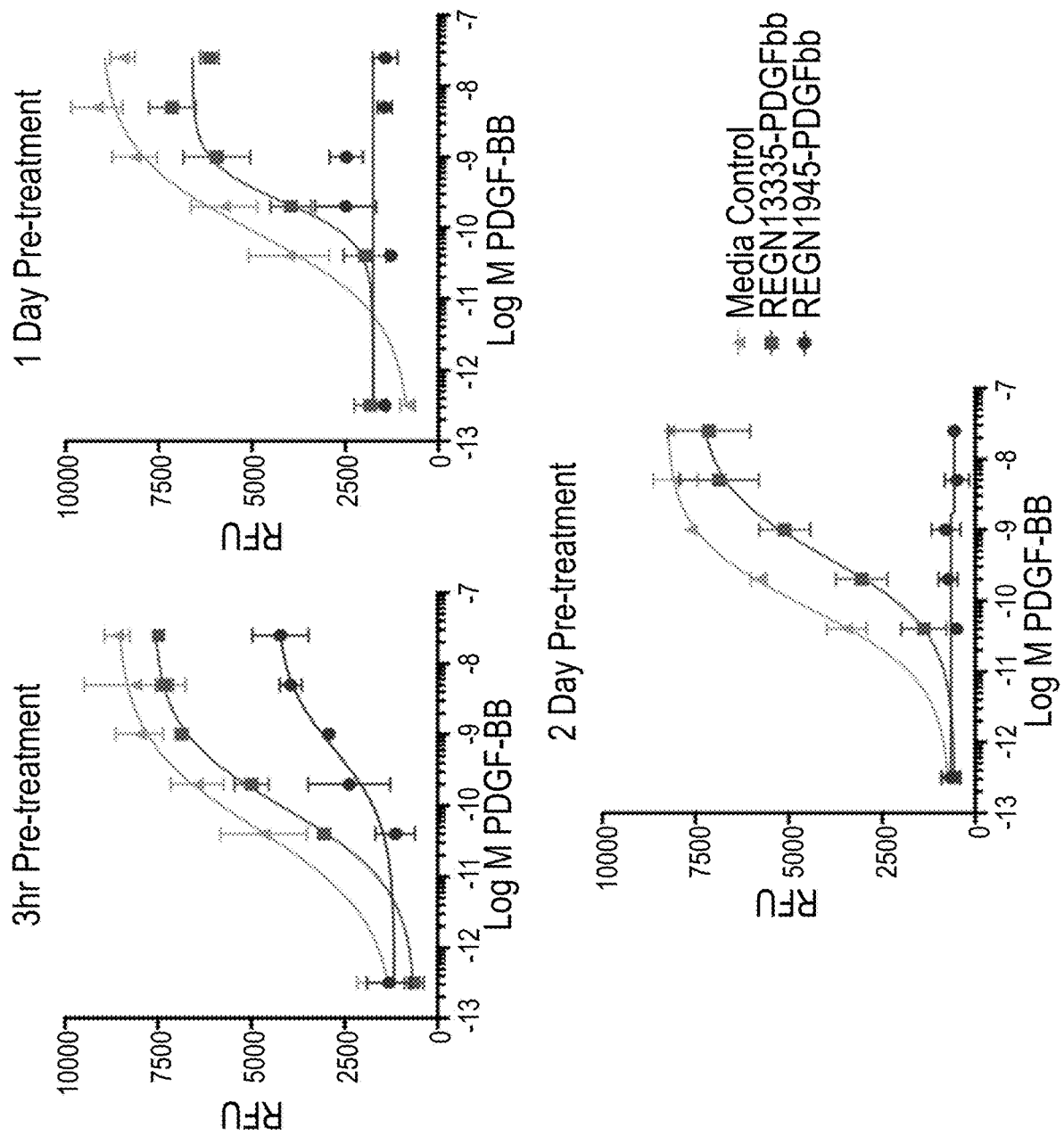
FIG. 29 is a panel of graphs depicting the Fluorescence Imaging Plate Reader (FLIPR) receptor internalization assay in pulmonary artery smooth muscle cells (PASMC) pretreated with anti-PDGF-B antibody-ligand complexes.

FLIPR Data: In this assay, PDGF-BB binds to the PDGF receptors and causes rapid receptor internalization and desensitization of the cells to subsequent PDGF-BB treatments. As shown in Table 25 and FIG. 29, PASMC pre-treated with REGN1945-PDGFBB (10:1 nM) were desensitized to subsequent PDGF-BB induced calcium flux. H4H13145P was able to neutralize PDGF-BB and limit the observed loss in responsiveness to PDGF-BB. Compared to the media control, the H4H13145P group was not able to fully prevent PDGF-BB desensitization. The H4H13145P-PDGFBB treatment had a slight rightward shift in potency and a small drop in the max-min calcium flux response at 5 nM of PDGF-BB treatment. This may be explained by the antibody-ligand complexes binding to the PDGFR receptor and causing receptor internalization, albeit at a rate and magnitude significantly slower than unbound PDGF-BB.

Flow Cytometry: PASMC express both PDGFRa and PDGFRb. No fluorescent signal was detected in the REGN1945-ligand treatment group for both PDGFRa and PDGFRb. This finding confirms rapid ligand dependent internalization of receptors in response to PDGF-BB. H4H13145P prevented the observed loss in PDGFRb fluorescent signal. There was a slight shift and loss of PDGFR cell surface expression in the H4H13145P treatment group compared to the media control indicating receptor internalization, albeit at a reduced rate and magnitude compared to unbound PDGF-BB.

TABLE 23

Fluorescent antibody labeling Internalization in PASMC

| | | Antibody prebinding with PDGF-AB | | Antibody prebinding with PDGF-BB | |
| --- | --- | --- | --- | --- | --- |
| PASMC | Pre-blocking Ab | A647 Intensity | Fold Change* | A647 Intensity | Fold Change* |
| H4H13145P | media | 2.3E+07 | 48.53 | 5.3E+07 | 108.71 |
| | Anti PDGFRα | 1.3E+07 | 27.40 | 5.3E+07 | 108.92 |

TABLE 23-continued

Fluorescent antibody labeling Internalization in PASMC

| PASMC | Pre-blocking Ab | Antibody prebinding with PDGF-AB | | Antibody prebinding with PDGF-BB | |
|---|---|---|---|---|---|
| | | A647 Intensity | Fold Change* | A647 Intensity | Fold Change* |
| | Anti PDGFRβ | 1.3E+07 | 28.47 | 4.2E+07 | 85.93 |
| | Anti PDGFRα + β | 652814 | 1.41 | 2842206 | 5.89 |
| REGN1945 | NA | 463585 | 1.00 | 482942 | 1.00 |
| H4H13145P | NA | 2.4E+07 | 51.99 | 5.3E+07 | 108.71 |
| H4H13132P | NA | 772127 | 1.67 | 1708915 | 3.54 |

TABLE 24

Fluorescent antibody labeling Internalization in NHLF

| NHDF | Pre-blocking Ab | Antibody prebinding with PDGF-AB | | Antibody prebinding with PDGF-BB | |
|---|---|---|---|---|---|
| | | A647 Intensity | Fold Change* | A647 Intensity | Fold Change* |
| H4H13145P | media | 1.9E+07 | 30.42 | 7.3E+07 | 126.82 |
| | Anti PDGFRα | 1.4E+07 | 22.90 | 5.3E+07 | 92.45 |
| | Anti PDGFRβ | 1.1E+07 | 17.61 | 3.4E+07 | 59.31 |
| | Anti PDGFRα + β | 9451698 | 15.13 | 1513178 | 2.64 |
| REGN1945 | NA | 624495 | 1.00 | 573275 | 1.00 |
| H4H13145P | NA | 1.9E+07 | 30.42 | 7.3E+07 | 126.82 |
| H4H13132P | NA | 679346 | 1.09 | 2669964 | 4.66 |

Data in the summary tables were selected at the $10^{th}$ hour of each assay
*Fold change = (pHrodo-A647 fluorescence intensity/pHrodo-A647 fluorescence intensity of isotype control Ab REGN1945)

TABLE 25

FLIPR Receptor Internalization Assay in PASMC

| | Media Control | | | H4H13145P-PDGFBB | | | REGN1945-PDGFBB | | |
|---|---|---|---|---|---|---|---|---|---|
| Time | 3 hr | 24 h | 48 hr | 3 hr | 24 hr | 48 hr | 3 hr | 24 hr | 48 h |
| EC50 | 48 pM | 85 pM | 79 pM | 93 pM | 230 pM | 400 pM | 600 pM | — | — |
| Max-Min at 5 nM PDGF-BB (RFU) | 8132 ± 1670 | 9066 ± 804 | 8345 ± 66 | 7408 ± 282 | 7410 ± 628 | 6822 ± 1501 | 3948 ± 293 | 1458 ± 192 | 492 ± 324 |

Example 19: Evaluation of the Effect of Two Inhibitory Anti-PDGF-B Antibodies in the Rat Monocrotaline Model of Pulmonary Arterial Hypertension Reagents The reagents used for evaluation of the effect of two inhibitory anti-PDGF-B antibodies in the rat monocrotaline model of pulmonary arterial hypertension included: Monocrotaline (Crotaline) Sigma Cat #PHL89251—CAS Number: 315-22-0, MDL: MFCD00084656, Formula: $C_{16}H_{23}NO_6$, Formula Weight: 325.36 g/mol, Storage Temperature: 2-8° C., Purity: 98%; Macitentan MedChemExpress Cat #HY-14184—Oral active endothelin receptor antagonist, CAS Number: 441798-33-0, Formula: $C_{19}H_{20}Br_2N_6O_4S$, Formula Weight: 588.27 g/mol, Lot #: 10673, Storage Temperature: −20° C. for 3 years, Purity: 98%; and PEG-400 (at 50:50 v/v, Affymetrix Inc., #19957).

Experimental Procedure

In order to evaluate the effect of two inhibitory anti-PDGF-B antibodies in the rat monocrotaline model of pulmonary arterial hypertension, 2 studies were performed: study #1 was performed on 4-week Monocrotaline PAH Rats with Preventive Drug Treatment; and study #2 was performed on 5-weeks Monocrotaline Severe PAH Rats Survival with Therapeutic Drug Treatment (Tables 26-27).

Six to seven weeks old male Sprague Dawley rats were used. Rats were separated into treatment groups such that body weights were similar among different groups. In study #1, one day prior of monocrotaline injection, rats in antibody treatment groups were subcutaneously administered either anti-PDGF-B antibodies or isotype control IgG at 10 mg/kg with dosing continuing at a rate of 2 times a week for 28 days. On day one, rats were subcutaneously administered either 40 mg/kg of monocrotaline or 5 mL/kg or saline as control. On day 28, right ventricular systolic pressure (RVSP) was measured by right heart catheterization and RV hypertrophy was calculated by Fulton index as the weight ratio of RV to (LV+septum). In study #2, rats were subcutaneously administered either 60 mg/kg of monocrotaline or 5 mL/kg of saline. Starting at day 14, rats in antibody treatment groups were subcutaneously administered either anti-PDGF-B antibody or isotype control IgG at 25 mg/kg, 2 times a week. Small molecule group was orally administered macitentan at 30 mg/kg daily. Body weight change from day 0-35 were used for general toxicity assessment and animal mortality and median survival time were calculated by day 35.

(Micro-tip catheter transducer SPR-1000, Millar Instruments, Inc.) was inserted into the opening of the Jugular vein and advanced past the right atrium into the right ventricle.

TABLE 26

Study #1-4 weeks Monocrotaline PAH Rats with Preventive Drug Treatment

| Group | Condition | Treatment | Monocrotaline | REGN# | Dosage | Frequency | Route | Starting Day | Number of rat/group |
|---|---|---|---|---|---|---|---|---|---|
| 1 | Saline | Saline | N/A | N/A | 5 ml/kg | Once at day 1 | SC | N/A | 8 |
| 2 | Monocrotaline (40 mg/kg) + Isotype control IgG | Isotype control IgG antibody | 40 mg/kg s.c once at day 1 | REGN1945 | 10 mg/kg | Twice per week | SC | −1 | 12 |
| 3 | Monocrotaline (40 mg/kg) + Anti-PDGF-B antibody 1 | Anti-PDGF-B antibody 1 | 40 mg/kg s.c once at day 1 | H4H13145P | 10 mg/kg | Twice per week | SC | −1 | 12 |
| 4 | Monocrotaline (40 mg/kg) + Anti-PDGF-B antibody 2 | Anti-PDGF-B antibody 2 | 40 mg/kg s.c once at day 1 | H4H13132P | 10 mg/kg | Twice per week | SC | −1 | 12 |

TABLE 27

Study #2-5 weeks Monocrotaline Severe PAH Rats Survival with Therapeutic Drug Treatment

| Group | Condition | Treatment | Monocrotaline | REGN# | Dosage | Frequency | Route | Starting Day | Number of rat/group |
|---|---|---|---|---|---|---|---|---|---|
| 1 | Saline | Saline | N/A | N/A | 5 ml/kg | Once at day 1 | SC | N/A | 8 |
| 2 | Monocrotaline (60 mg/kg) + Isotype control IgG | Isotype control IgG antibody | 60 mg/kg s.c once at day 1 | REGN 1945 | 10 mg/kg | Twice per week | SC | 14 | 16 |
| 3 | Monocrotaline (40 mg/kg) + Anti-PDGF-B antibody | Anti-PDGF-B antibody | 60 mg/kg s.c once at day 1 | REGN 13335 | 10 mg/kg | Twice per week | SC | 14 | 12 |
| 4 | Monocrotaline (40 mg/kg) + Macitentan | Endothelin Receptor Antagonist Macitentan | 60 mg/kg s.c once at day 1 | N/A | 30 mg/kg | Daily | gavage | 14 | 11 |
| 5 | Monocrotaline (40 mg/kg) + Macitentan + anti-PDGF-B antibody | Anti-PDGF-B + Macitentan | 60 mg/kg s.c once at day 1 | REGN 13335 | Macitentan 30 mg/kg REGN 13335 10 mg/kg | Mac: daily REGN 13335 Twice per week | Mac:gavage H4H13145P:SC |  | 12 |

Right heart catheterization and right ventricular systolic pressure: Rats were anesthetized with isoflurane and were kept at approximately 37° C. using a heated platform (Heated Hard Pad 1, Braintree Scientific) and circulating heated water pump (T/Pump Classic, Gaymar Industries). The neck area for each rat was prepared for surgery by depilating over the right common Carotid artery and right Jugular vein. An incision was made, and the right Jugular vein was isolated with care as to not damage the carotid artery and/or the vagus nerve. A piece of 5-0 silk suture was placed under the isolated Jugular vein to allow for retraction of the vessel cranially, then a 23-guage needle was used to introduce a hole into the Jugular vein. A pressure catheter (Micro-tip catheter transducer SPR-1000, Millar Instruments, Inc.) was inserted into the opening of the Jugular vein and advanced past the right atrium into the right ventricle. The catheter was connected to pressure/volume instrument (MPVS-300, Millar Instruments, Inc.) that measured heart rate as well as both diastolic and systolic right ventricular pressures. These parameters were digitally acquired using a data acquisition system (PowerLab 4/35, AD Instruments). LabChart Pro 7.0 software (AD Instruments) was used to analyze right ventricular pressures. Readings were quantified from a 60 second interval of the pressure tracing (following a 2-minute period of recording to allow for pressure stabilization). The parameters analyzed were right ventricular systolic pressures (RVSP) and heart rate (HR).

Right heart hypertrophy assessment: After the in vivo hemodynamic measurements, animals were euthanized by exsanguinations under anesthesia and then RV free wall, left ventricle (LV) and septum tissue were harvested and weighted. RV hypertrophy was calculated by Fulton index as the weight ratio of RV to (LV+septum).

Results

Right ventricular pressure elevation induced in monocrotaline rats: In study #1 in monocrotaline treated rats, catheter-based assessment of heart right ventricular pressures (right ventricular systolic pressure) and right ventricular hypertrophy in the monocrotaline rat model of PAH. Therapeutic treatment of Regeneron Anti-PDGF-B antibody demonstrated superior survival benefit over the vasodilatory drug endothelin receptor antagonist Macitentan in a severe monocrotaline rat PAH model. Anti-PDGF-B antibody H4H13145P significantly rescued animal mortality and prolonged survival time.

TABLE 28

| Group | Drug | Dosage mg/kg | Rat # | Right ventricular systolic pressure (RVSP) Mean ± SD | Reduction % (RYSP) % | Right ventricular hypertrophy (Fulton index) Mean ± SD | Reduction % (RV Hypertrophy) % |
|---|---|---|---|---|---|---|---|
| Saline | N/A | N/A | 8 | 26.38 ± 2.77 | N/A | 0.2861 ± 0.0292 | N/A |
| MCT + Iso Ctrl IgG | REGN1945 | 10 | 12 | 71.15 ± 8.82* | N/A | 0.6871 ± 0.0910* | N/A |
| MCT + anti-PDGF-B ab1 | H4H13145P | 10 | 11 | 54.36 ± 12.87*## | 38% | 0.5431 ± 0.1313*# | 36% |
| MCT + anti-PDGF-B ab2 | H4H13132P | 10 | 11 | 55.26 ± 11.56*## | 35% | 0.5644 ± 0.1347*# | 30% |

Figure 30:
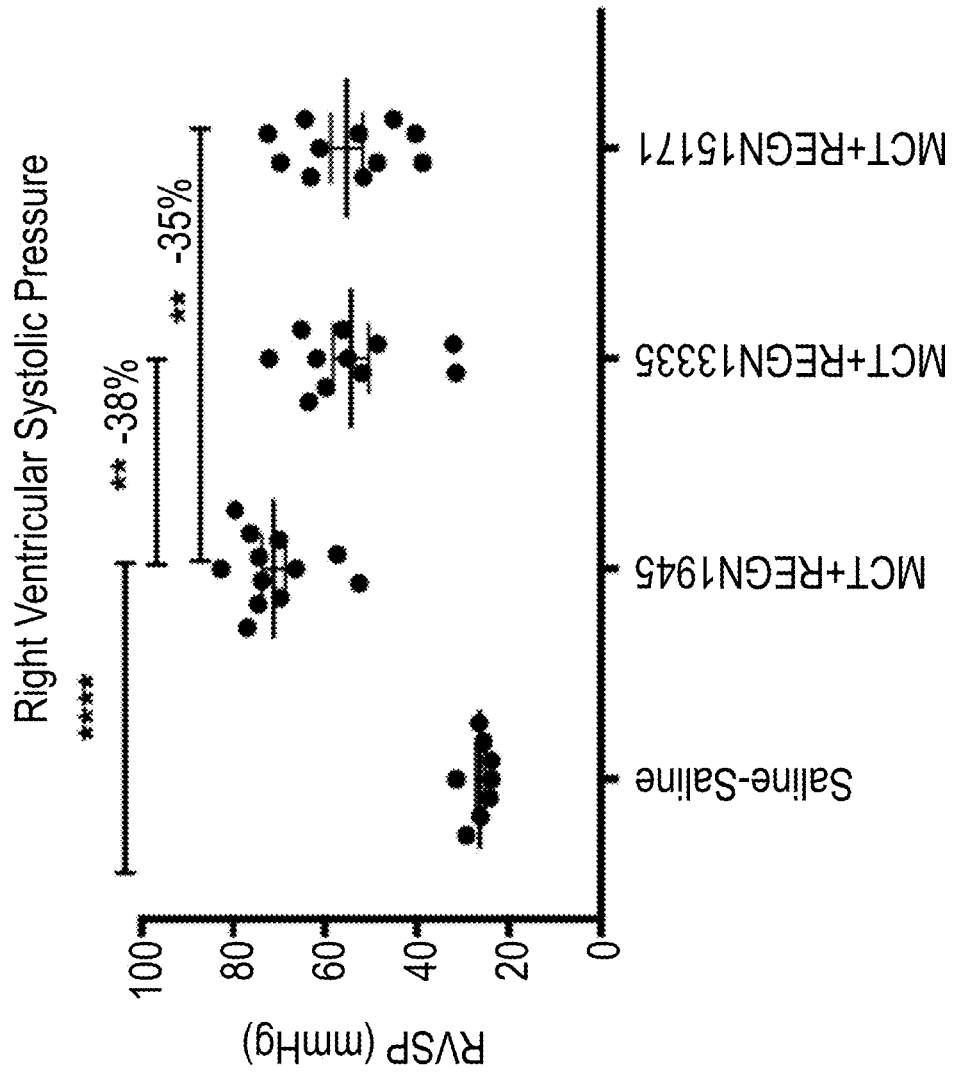
FIG. 30 is a graph depicting a study in monocrotaline treated rats for catheter-based assessment of heart right ventricular pressures, which demonstrated that anti- PDGF-B antibody treatments reduced right ventricular systolic pressure in comparison to the isotype control-treated rats.

*$p < 0.00001$ vs Saline control,
$p < 0.01$ vs MCT + Iso Control IgG,
$p < 0.05$ vs MCT + Iso Control IgG revealed a significant elevation of right ventricle systolic pressures in the isotype antibody-treated group at week 4. The two anti-PDGF-B antibody treatments significantly reduced right ventricular systolic pressure (FIG. 30 and Table 28).

Figure 31:
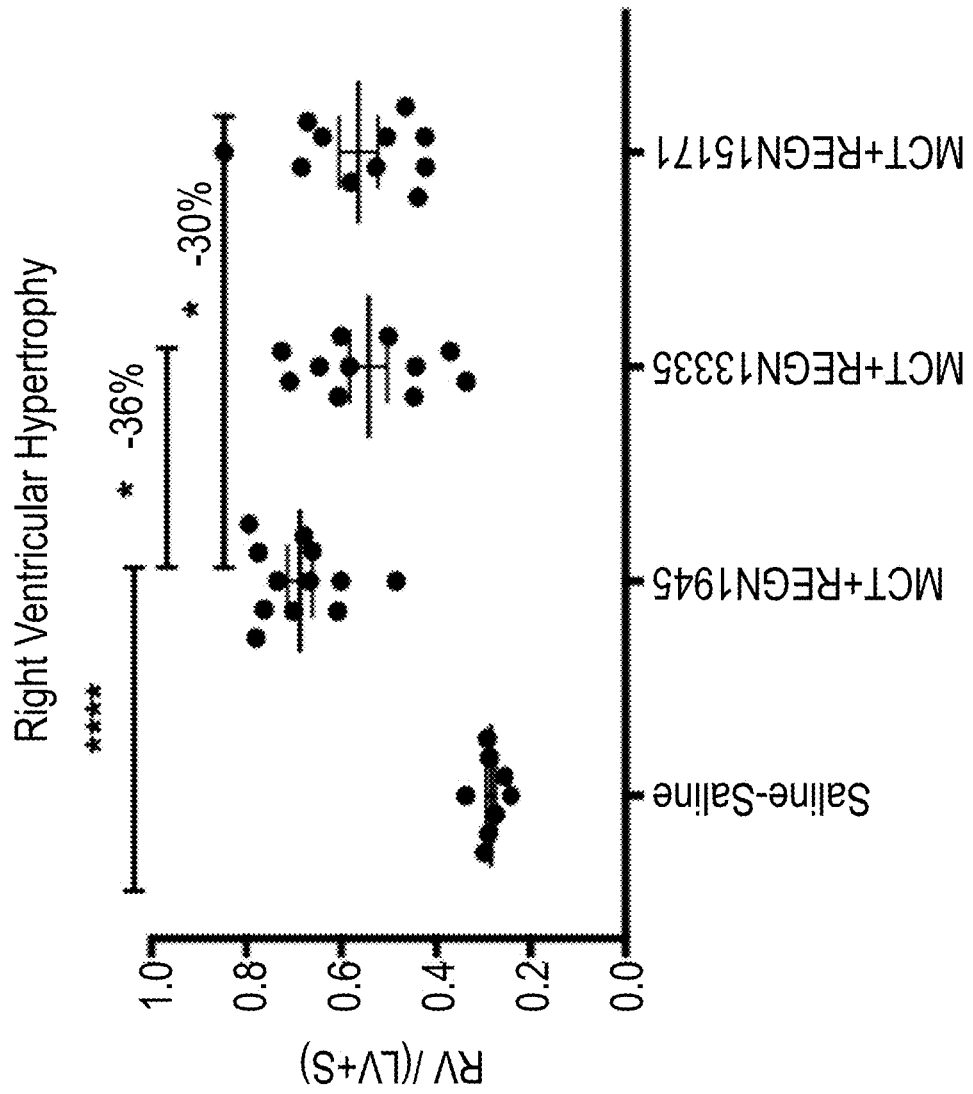
FIG. 31 is a graph depicting that preventive treatment with anti-PDGF-B antibodies reduced right ventricular hypertrophy in comparison to the isotype control-treated rats.

Right ventricular hypertrophy induced in monocrotaline rats: Increased right ventricular heart weight was observed in monocrotaline rats in the isotype control IgG treatment group. The ratio of the right ventricular weight to the left ventricular plus septal weight provides an index of right ventricular hypertrophy (i.e., Fulton Index). Increased futon index was observed in monocrotaline treated rats relative to saline treated controls, indicating the presence of right ventricular hypertrophy. Preventive treatment with anti-PDGF-B antibodies H4H13145P and H4H13132P at 10 mg/kg reduced right ventricular hypertrophy by 36% and 30% respectively, when compared to the isotype control-treated rats (FIG. 31 and Table 28).

Figure 32:
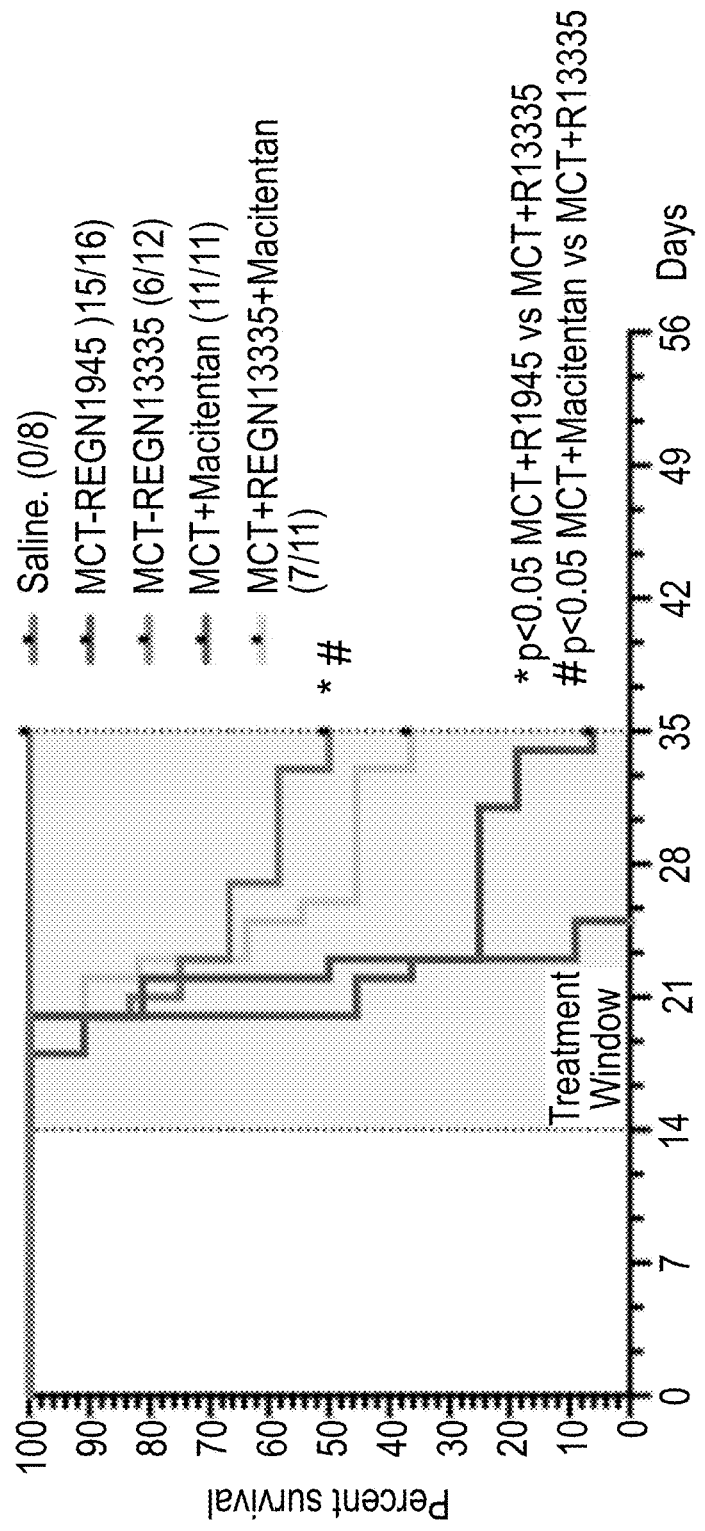
FIG. 32 is a graph depicting that a combination of endothelin receptor antagonist Macitentan with anti-PDGF-B treatment showed no further survival benefit compared to monotherapy with an anti-PDGF-B antibody.

Animal survival rate in monocrotaline rats: In study #2, the rats injected with 60 mg/kg monocrotaline developed severe pulmonary hypertension symptoms and high mortality. Notably, 15 out of 16 rats in monocrotaline with isotype control IgG treatment group died by day 35. The anti-PDGF-B antibody H4H13145P, started 14 days post monocrotaline injection, significantly prolonged the survival time and improved mortality. The standard of care drug, endothelin receptor antagonist Macitentan, failed to prolong survival. The combination of Macitentan with anti-PDGF-B treatment showed no further survival benefit compared to monotherapy with anti-PDGF-B antibody (FIG. 32 and Table 29).

In summary, preventative treatment with Regeneron Anti-PDGF-B antibodies reduced both hemodynamic endpoints

TABLE 29

| Group | Rat # | Death # by day 35 | Survival rate by day 35 | median survival (day) |
|---|---|---|---|---|
| Saline | 8 | 0 | 1 | N/A |
| MCT-REGN1945 | 16 | 15 | 6%* | 22.5 |
| MCT-H4H13145P | 12 | 6 | 50%*# | 34 |
| MCT + Macitentan | 11 | 11 | 0%* | 20 |
| MCT + H4H13145P + Macitentan | 11 | 7 | 36%*Δ | 26 |

*$p < 0.00001$ vs Saline control,
$p < 0.05$ vs MCT + Iso Control IgG,
Δ$p < 0.01$ vs MCT + Macitentan

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INFORMAL SEQUENCE LISTING

H4H13145P
SEQ ID NO: 1; HCVR
CAGGTTCAGCTGGTGCAGTCTGGAACTGAGGTGAAGAAGCCTGGGGCCTCAGTAAAGGTCTCCTGCA
AGGCCTCTGGTTATACTTATGGTGCCTATGCAATCAGCTGGGTGCGACAGGCCCCTGGACAAGGCCT
TGAGTGGATGGGATGGATCAGCGCTTACAATGGTAACACAAACTATGCACAGAAATTCCAGGACAGA
GTCACCATGACCACAGACACATCCACGAACACAGCCTACATGGAACTGAGGGGCCTAAAATCTGACG
ACACGGCCGTGTATTTCTGTGCGAGGGCCTGGAACTCCTTTGACTACTGGGGCCAGGGCACCCTGGT
CACTGTCTCCTCA
SEQ ID NO: 2; HCVR
QVQLVQSGTEVKKPGASVKVSCKASGYTYGAYAISWVRQAPGQGLEWMGWISAYNGNTNYAQKFQDR
VTMTTDTSTNTAYMELRGLKSDDTAVYFCARAWNSFDYWGQGTLVTVSS
SEQ ID NO: 3; HCDR1
GGT TAT ACT TAT GGT GCC TAT GCA
SEQ ID NO: 4; HCDR1
G Y T Y G A Y A
SEQ ID NO: 5; HCDR2
ATC AGC GCT TAC AAT GGT AAC ACA
SEQ ID NO: 6; HCDR2
I S A Y N G N T
SEQ ID NO: 7; HCDR3
GCG AGG GCC TGG AAC TCC TTT GAC TAC
SEQ ID NO: 8; HCDR3
A R A W N S F D Y
SEQ ID NO: 9; LCVR
GACATCCAGATGACCCAGTCTCCATCCTCCCTGTCTGCGTCTGTAGGAGACAGAGTCACCATCACTT
GCCAGGCGAGTCAGGACATTAGGAAAAATTTAAATTGGTATCAACAGAAACCAGGGAAAGCCCCTAA
GCTCCTGATCTCCGATGCATCCACTTTAGAAACAGGGGTCCCATCAAGATTCAGTGGAAGTGGATCT
GGGACAGATTTTACTTTCACCATCAGCAGCCTGCAGCCTGAAGATATTGCAAATATTACTGTCAAC
AATATTATAATCTCCCATTCACTTTCGGCCCTGGGACCAAAGTGGATATCAAA
SEQ ID NO: 10; LCVR
DIQMTQSPSSLSASVGDRVTITCQASQDIRKNLNWYQQKPGKAPKLLISDASTLETGVPSRFSGSGS
GTDFTFTISSLQPEDIAKYYCQQYYNLPFTFGPGTKVDIK
SEQ ID NO: 11; LCDR1
CAG GAC ATT AGG AAA AAT
SEQ ID NO: 12; LCDR1
Q D I R K N
SEQ ID NO: 13; LCDR2
GAT GCA TCC
SEQ ID NO: 14; LCDR2
D A S
SEQ ID NO: 15; LCDR3
CAA CAA TAT TAT AAT CTC CCA TTC ACT
SEQ ID NO: 16; LCDR3
Q Q Y Y N L P F T
SEQ ID NO: 17; HC
CAGGTTCAGCTGGTGCAGTCTGGAACTGAGGTGAAGAAGCCTGGGGCCTCAGTAAAGGTCTCCTGCA
AGGCCTCTGGTTATACTTATGGTGCCTATGCAATCAGCTGGGTGCGACAGGCCCCTGGACAAGGCCT
TGAGTGGATGGGATGGATCAGCGCTTACAATGGTAACACAAACTATGCACAGAAATTCCAGGACAGA
GTCACCATGACCACAGACACATCCACGAACACAGCCTACATGGAACTGAGGGGCCTAAAATCTGACG
ACACGGCCGTGTATTTCTGTGCGAGGGCCTGGAACTCCTTTGACTACTGGGGCCAGGGCACCCTGGT
CACTGTCTCCTCAGCCTCCACCAAGGGCCCATCGGTCTTCCCCCTGGCGCCCTGCTCCAGGAGCACC
TCCGAGAGCACAGCCGCCCTGGGCTGCCTGGTCAAGGACTACTTCCCCGAACCGGTGACGGTGTCGT
GGAACTCAGGCGCCCTGACCAGCGGCGTGCACACCTTCCCGGCTGTCCTACAGTCCTCAGGACTCTA
CTCCCTCAGCAGCGTGGTGACCGTGCCCTCCAGCAGCTTGGGCACGAAGACCTACACCTGCAACGTA
GATCACAAGCCCAGCAACACCAAGGTGGACAAGAGAGTTGAGTCCAAATATGGTCCCCCATGCCCAC
CCTGCCCAGCACCTGAGTTCCTGGGGGGACCATCAGTCTTCCTGTTCCCCCCAAAACCCAAGGACAC
TCTCATGATCTCCCGGACCCCTGAGGTCACGTGCGTGGTGGTGGACGTGAGCCAGGAAGACCCCGAG
GTCCAGTTCAACTGGTACGTGGATGGCGTGGAGGTGCATAATGCCAAGACAAAGCCGCGGGAGGAGC
AGTTCAACAGCACGTACCGTGTGGTCAGCGTCCTCACCGTCCTGCACCAGGACTGGCTGAACGGCAA
GGAGTACAAGTGCAAGGTCTCCAACAAAGGCCTCCCGTCCTCCATCGAGAAAACCATCTCCAAAGCC
AAAGGGCAGCCCCGAGAGCCACAGGTGTACACCCTGCCCCCATCCCAGGAGGAGATGACCAAGAACC
AGGTCAGCCTGACCTGCCTGGTCAAAGGCTTCTACCCCAGCGACATCGCCGTGGAGTGGGAGAGCAA
TGGGCAGCCGGAGAACAACTACAAGACCACGCCTCCCGTGCTGGACTCCGACGGCTCCTTCTTCCTC
TACAGCAGGCTCACCGTGGACAAGAGCAGGTGGCAGGAGGGGAATGTCTTCTCATGCTCCGTGATGC
ATGAGGCTCTGCACAACCACTACACACAGAAGTCCCTCTCCCTGTCTCTGGGTAAATGA
SEQ ID NO: 18; HC
QVQLVQSGTEVKKPGASVKVSCKASGYTYGAYAISWVRQAPGQGLEWMGWISAYNGNTNYAQKFQDR
VTMTTDTSTNTAYMELRGLKSDDTAVYFCARAWNSFDYWGQGTLVTVSSASTKGPSVFPLAPCSRST
SESTAALGCLVKDYFPEPVTVSWNSGALTSGVHTFPAVLQSSGLYSLSSVVTVPSSSLGTKTYTCNV
DHKPSNTKVDKRVESKYGPPCPPCPAPEFLGGPSVFLFPPKPKDTLMISRTPEVTCVVVDVSQEDPE
VQFNWYVDGVEVHNAKTKPREEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQPENNYKTTPPVLDSDGSFFL
YSRLTVDKSRWQEGNVFSCSVMHEALHNHYTQKSLSLSLGK*
SEQ ID NO: 19; LC
GACATCCAGATGACCCAGTCTCCATCCTCCCTGTCTGCGTCTGTAGGAGACAGAGTCACCATCACTT
GCCAGGCGAGTCAGGACATTAGGAAAAATTTAAATTGGTATCAACAGAAACCAGGGAAAGCCCCTAA
GCTCCTGATCTCCGATGCATCCACTTTAGAAACAGGGGTCCCATCAAGATTCAGTGGAAGTGGATCT
GGGACAGATTTTACTTTCACCATCAGCAGCCTGCAGCCTGAAGATATTGCAAATATTACTGTCAAC
AATATTATAATCTCCCATTCACTTTCGGCCCTGGGACCAAAGTGGATATCAAACGAACTGTGGCTGC

| INFORMAL SEQUENCE LISTING |
|---|
| ACCATCTGTOTTCATCTTCCCGCCATCTGATGAGCAGTTGAAATCTGGAACTGCCTCTGTTGTGTGC
CTGCTGAATAACTTCTATCCCAGAGAGGCCAAAGTACAGTGGAAGGTGGATAACGCCCTCCAATCGG
GTAACTCCCAGGAGAGTGTCACAGAGCAGGACAGCAAGGACAGCACCTACAGCCTCAGCAGCACCCT
GACGCTGAGCAAAGCAGACTACGAGAAACACAAAGTCTACGCCTGCGAAGTCACCCATCAGGGCCTG
AGCTCGCCCGTCACAAAGAGCTTCAACAGGGGAGAGTGTTAG
SEQ ID NO: 20; LC
DIQMTQSPSSLSASVGDRVTITCQASQDIRKNLNWYQQKPGKAPKLLISDASTLETGVPSRFSGSGS
GTDFTFTISSLQPEDIAKYYCQQYYNLPFTFGPGTKVDIKRTVAAPSVFIFPPSDEQLKSGTASVVC
LLNNFYPREAKVQWKVDNALQSGNSQESVTEQDSKDSTYSLSSTLTLSKADYEKHKVYACEVTHQGL
SSPVTKSFNRGEC\*

H4H13132P
SEQ ID NO: 21; HCVR
CAGGTGCAGCTGGTACAGTCTGGGGCTGAGGTGAAGAAGCCTGGGTCCTCGGTGAAGGTCTCCTGCA
AGGCTTCTGGAGGCACCTTCAGCAGCTATGCTATCAGCTGGGTGCGACAGGCCCCTGGACAAGGGCT
TGAGTGGATGGGAGGGATCATCCCTATCTTTGGTACAGCAAACTACGCACAGAAGTTCCAGGGCAGA
GTCACGATTACCACGGACGAATCCACGAGCACAGCCTACATGGAGCTGAGCAGCCTGAGATCTGAGG
ACACGGCCGTATATTACTGTGCGAGAGAGGGCTACGGTGACTACTACTTCGGTATGGACGTCTGGGG
CCAAGGGACCACGGTCACCGTCTCCTCA
SEQ ID NO: 22; HCVR
QVQLVQSGAEVKKPGSSVKVSCKASGGTFSSYAISWVRQAPGQGLEWMGGIIPIFGTANYAQKFQGR
VTITTDESTSTAYMELSSLRSEDTAVYYCAREGYGDYYFGMDVWGQGTTVTVSS
SEQ ID NO: 23; HCDR1
GGA GGC ACC TTC AGC AGC TAT GCT
SEQ ID NO: 24; HCDR1
G G T F S S Y A
SEQ ID NO: 25; HCDR2
ATC ATC CCT ATC TTT GGT ACA GCA
SEQ ID NO: 26; HCDR2
I I P I F G T A
SEQ ID NO: 27; HCDR3
GCG AGA GAG GGC TAC GGT GAC TAC TAC TTC GGT ATG GAC GTC
SEQ ID NO: 28; HCDR3
A R E G Y G D Y Y F G M D V
SEQ ID NO: 29; LCVR
GATGTTGTGATGACTCAGTCTCCACTCTCCCTGCCCGTCACCCTTGGACAGCCGGCCTCCATCTCCT
GCAGGTCTAGTCAAAGCCTCGTATACAGTGATGGAAACACCTACTTGAATTGGTTTCAGCAGAGGCC
AGACCAATCTCCAAGGCGCCTAATTTATAAGATTTCTAACCGGGACTCTGGGGTCCCAGACAGATTC
AGCGGCAGTGGGTCAGGCACTGATTTCACACTGAAAATCAGCAGGGTGGAGGCTGAGGATGTTGGGG
TTTATTACTGCATGCAAGGTACACACTGGCCTCCCACTTTTGGCCAGGGGACCAAGCTGGAGATCAA
A
SEQ ID NO: 30; LCVR
DVVMTQSPLSLPVTLGQPASISCRSSQSLVYSDGNTYLNWFQQRPDQSPRRLIYKISNRDSGVPDRF
SGSGSGTDFTLKISRVEAEDVGVYYCMQGTHWPPTFGQGTKLEIK
SEQ ID NO: 31; LCDR1
CAA AGC CTC GTA TAC AGT GAT GGA AAC ACC TAC
SEQ ID NO: 32; LCDR1
Q S L V Y S D G N T Y
SEQ ID NO: 33; LCDR2
AAG ATT TCT
SEQ ID NO: 34; LCDR2
K I S
SEQ ID NO: 35; LCDR3
ATG CAA GGT ACA CAC TGG CCT CCC ACT
SEQ ID NO: 36; LCDR3
M Q G T H W P P T
SEQ ID NO: 37; HC
CAGGTGCAGCTGGTACAGTCTGGGGCTGAGGTGAAGAAGCCTGGGTCCTCGGTGAAGGTCTCCTGCA
AGGCTTCTGGAGGCACCTTCAGCAGCTATGCTATCAGCTGGGTGCGACAGGCCCCTGGACAAGGGCT
TGAGTGGATGGGAGGGATCATCCCTATCTTTGGTACAGCAAACTACGCACAGAAGTTCCAGGGCAGA
GTCACGATTACCACGGACGAATCCACGAGCACAGCCTACATGGAGCTGAGCAGCCTGAGATCTGAGG
ACACGGCCGTATATTACTGTGCGAGAGAGGGCTACGGTGACTACTACTTCGGTATGGACGTCTGGGG
CCAAGGGACCACGGTCACCGTCTCCTCAGCCTCCACCAAGGGCCCATCGGTCTTCCCCCTGGCGCCC
TGCTCCAGGAGCACCTCCGAGAGCACAGCCGCCCTGGGCTGCCTGGTCAAGGACTACTTCCCCGAAC
CGGTGACGGTGTCGTGGAACTCAGGCGCCCTGACCAGCGGCGTGCACACCTTCCCGGCTGTCCTACA
GTCCTCAGGACTCTACTCCCTCAGCAGCGTGGTGACCGTGCCCTCCAGCAGCTTGGGCACGAAGACC
TACACCTGCAACGTAGATCACAAGCCCAGCAACACCAAGGTGGACAAGAGAGTTGAGTCCAAATATG
GTCCCCCATGCCCACCCTGCCCAGCACCTGAGTTCCTGGGGGGACCATCAGTCTTCCTGTTCCCCCC
AAAACCCAAGGACACTCTCATGATCTCCCGGACCCCTGAGGTCACGTGCGTGGTGGTGGACGTGAGC
CAGGAAGACCCCGAGGTCCAGTTCAACTGGTACGTGGATGGCGTGGAGGTGCATAATGCCAAGACAA
AGCCGCGGGAGGAGCAGTTCAACAGCACGTACCGTGTGGTCAGCGTCCTCACCGTCCTGCACCAGGA
CTGGCTGAACGGCAAGGAGTACAAGTGCAAGGTCTCCAACAAAGGCCTCCCGTCCTCCATCGAGAAA
ACCATCTCCAAAGCCAAAGGGCAGCCCCGAGAGCCACAGGTGTACACCCTGCCCCCATCCCAGGAGG
AGATGACCAAGAACCAGGTCAGCCTGACCTGCCTGGTCAAAGGCTTCTACCCCAGCGACATCGCCGT |

GGAGTGGGAGAGCAATGGGCAGCCGGAGAACAACTACAAGACCACGCCTCCCGTGCTGGACTCCGAC
GGCTCCTTCTTCCTCTACAGCAGGCTCACCGTGGACAAGAGCAGGTGGCAGGAGGGGAATGTCTTCT
CATGCTCCGTGATGCATGAGGCTCTGCACAACCACTACACACAGAAGTCCCTCTCCCTGTCTCTGGG
TAAATGA

SEQ ID NO: 38; HC
QVQLVQSGAEVKKPGSSVKVSCKASGGTFSSYAISWVRQAPGQGLEWMGGIIPIFGTANYAQKFQGR
VTITTDESTSTAYMELSSLRSEDTAVYYCAREGYGDYYFGMDVWGQGTTVTVSSASTKGPSVFPLAP
CSRSTSESTAALGCLVKDYFPEPVTVSWNSGALTSGVHTFPAVLQSSGLYSLSSVVTVPSSSLGTKT
YTCNVDHKPSNTKVDKRVESKYGPPCPPCPAPEFLGGPSVFLFPPKPKDTLMISRTPEVTCVVVDVS
QEDPEVQFNWYVDGVEVHNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESNGQPENNYKTTPPVLDSD
GSFFLYSRLTVDKSRWQEGNVESCSVMHEALHNHYTQKSLSLSLGK*

SEQ ID NO: 39; LC
GATGTTGTGATGACTCAGTCTCCACTCTCCCTGCCCGTCACCCTTGGACAGCCGGCCTCCATCTCCT
GCAGGTCTAGTCAAAGCCTCGTATACAGTGATGGAAACACCTACTTGAATTGGTTTCAGCAGAGGCC
AGACCAATCTCCAAGGCGCCTAATTTATAAGATTTCTAACCGGGACTCTGGGGTCCCAGACAGATTC
AGCGGCAGTGGGTCAGGCACTGATTTCACACTGAAAATCAGCAGGGTGGAGGCTGAGGATGTTGGGG
TTTATTACTGCATGCAAGGTACACACTGGCCTCCCACTTTTGGCCAGGGGACCAAGCTGGAGATCAA
ACGAACTGTGGCTGCACCATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGTACAGTGGAAGGTGGATA
ACGCCCTCCAATCGGGTAACTCCCAGGAGAGTGTCACAGAGCAGGACAGCAAGGACAGCACCTACAG
CCTCAGCAGCACCCTGACGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGAGTGTTAG

SEQ ID NO: 40; LC
DVVMTQSPLSLPVTLGQPASISCRSSQSLVYSDGNTYLNWFQQRPDQSPRRLIYKISNRDSGVPDRF
SGSGSGTDFTLKISRVEAEDVGVYYCMQGTHWPPTFGQGTKLEIKRTVAAPSVFIFPPSDEQLKSGT
ASVVCLLNNFYPREAKVQWKVDNALQSGNSQESVTEQDSKDSTYSLSSTLTLSKADYEKHKVYACEV
THQGLSSPVTKSFNRGEC* hPDGF-B
SEQ ID NO: 41; P01127|PDGFB_HUMAN Platelet-derived Growth Factor
Subunit B OS = Homo sapiens OX = 9606 GN = PDGFB PE = 1 SV = 1
MNRCWALFLSLCCYLRLVSAEGDPIPEELYEMLSDHSIRSFDDLQRLLHGDPGEEDGAELDLNMTRS
HSGGELESLARGRRSLGSLTIAEPAMIAECKTRTEVFEISRRLIDRTNANFLVWPPCVEVQRCSGCC
NNRNVQCRPTQVQLRPVQVRKIEIVRKKPIFKKATVTLEDHLACKCETVAAARPVTRSPGGSQEQRA
KTPQTRVTIRTVRVRRPPKGKHRKFKHTHDKTALKETGA

What is claimed is:

1. An isolated human monoclonal antibody, or antigen-binding fragment thereof, that binds specifically to human Platelet-Derived Growth Factor Subunit B (PDGF-B), wherein the antibody, or antigen-binding fragment thereof, comprises:

(a) an HCDR1 domain comprising the amino acid sequence set forth in SEQ ID NO: 4;

(b) an HCDR2 domain comprising the amino acid sequence set forth in SEQ ID NO: 6;

(c) an HCDR3 domain comprising the amino acid sequence set forth in SEQ ID NO: 8;

(d) an LCDR1 domain comprising the amino acid sequence set forth in SEQ ID NO: 12;

(e) an LCDR2 domain comprising the amino acid sequence set forth in SEQ ID NO: 14; and (f) an LCDR3 domain comprising the amino acid sequence set forth in SEQ ID NO: 16.

2. The isolated human antibody, or antigen-binding fragment thereof, of claim 1, wherein the antibody or antigen-binding fragment comprises an HCVR comprising an amino acid sequence having at least 90% identity to the sequence of SEQ ID NO:2.

3. The isolated human antibody, or antigen-binding fragment thereof, of claim 1, wherein the antibody or antigen-binding fragment comprises an LCVR comprising an amino acid sequence having at least 90% identity to the sequence of SEQ ID NO:10.

4. The isolated human antibody, or antigen-binding fragment thereof, of claim 1, wherein the antibody, or antigen-binding fragment thereof, comprises: (a) an HCVR comprising an amino acid sequence of SEQ ID NO:2; or (b) an LCVR comprising an amino acid sequence of SEQ ID NO:10.

5. The isolated human antibody, or antigen-binding fragment thereof, of claim 1, wherein the antibody, or antigen-binding fragment thereof, comprises an HCVR/LCVR amino acid sequence pair of SEQ ID NOs: 2/10.

6. The antigen-binding fragment of claim 1, wherein the antigen-binding fragment is a Fab fragment, a F(ab')2 fragment, a Fv fragment, or a single-chain Fv (scFv) molecule.

7. An injection device or vessel comprising an antibody, or antigen-binding fragment thereof, of claim 1.

8. A pharmaceutical composition comprising an isolated human antibody, or antigen-binding fragment thereof, that binds to human PDGF-B according to claim 1, and a pharmaceutically acceptable carrier or diluent; and, optionally, one or more additional therapeutic agents.

9. The pharmaceutical composition of claim 8, wherein the one or more additional therapeutic agents comprise an iron supplement.

* * * * *

SEQUENCE LISTING

<160> NUMBER OF SEQ ID NOS: 41

<210> SEQ ID NO 1
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
caggttcagc tggtgcagtc tggaactgag gtgaagaagc ctggggcctc agtaaaggtc      60
tcctgcaagg cctctggtta tacttatggt gcctatgcaa tcagctgggt gcgacaggcc     120
cctggacaag gccttgagtg gatgggatgg atcagcgctt acaatggtaa cacaaactat     180
gcacagaaat tccaggacag agtcaccatg accacagaca tccacgaa cacagcctac      240 atggaactga ggggcctaaa atctgacgac acggccgtgt atttctgtgc gagggcctgg     300
aactcctttg actactgggg ccagggcacc ctggtcactg tctcctca                 348

<210> SEQ ID NO 2
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Val Gln Leu Val Gln Ser Gly Thr Glu Val Lys Lys Pro Gly Ala
1               5                   10                  15

Ser Val Lys Val Ser Cys Lys Ala Ser Gly Tyr Thr Tyr Gly Ala Tyr
            20                  25                  30

Ala Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Phe
    50                  55                  60

Gln Asp Arg Val Thr Met Thr Thr Asp Thr Ser Thr Asn Thr Ala Tyr
65                  70                  75                  80

Met Glu Leu Arg Gly Leu Lys Ser Asp Asp Thr Ala Val Tyr Phe Cys
                85                  90                  95

Ala Arg Ala Trp Asn Ser Phe Asp Tyr Trp Gly Gln Gly Thr Leu Val
            100                 105                 110

Thr Val Ser Ser
        115

<210> SEQ ID NO 3
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
ggttatactt atggtgccta tgca                                           24

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Tyr Thr Tyr Gly Ala Tyr Ala
1               5

<210> SEQ ID NO 5
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
atcagcgctt acaatggtaa caca                                           24

<210> SEQ ID NO 6
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 6

Ile Ser Ala Tyr Asn Gly Asn Thr
1               5

<210> SEQ ID NO 7
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
gcgagggcct ggaactcctt tgactac                                             27

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ala Arg Ala Trp Asn Ser Phe Asp Tyr
1               5

<210> SEQ ID NO 9
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
gacatccaga tgacccagtc tccatcctcc ctgtctgcgt ctgtaggaga cagagtcacc          60
atcacttgcc aggcgagtca ggacattagg aaaaatttaa attggtatca acagaaacca         120
gggaaagccc ctaagctcct gatctccgat gcatccactt tagaaacagg ggtcccatca         180
agattcagtg gaagtggatc tgggacagat tttactttca ccatcagcag cctgcagcct         240
gaagatattg caaaatatta ctgtcaacaa tattataatc tcccattcac tttcggccct         300
gggaccaaag tggatatcaa a                                                   321

<210> SEQ ID NO 10
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Lys Asn
                20                  25                  30

Leu Asn Trp Tyr Gln Gln Lys Pro Gly Lys Ala Pro Lys Leu Leu Ile
        35                  40                  45
```

```
Ser Asp Ala Ser Thr Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Lys Tyr Tyr Cys Gln Gln Tyr Tyr Asn Leu Pro Phe
                 85                  90                  95

Thr Phe Gly Pro Gly Thr Lys Val Asp Ile Lys
            100                 105

<210> SEQ ID NO 11
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
caggacatta ggaaaaat                                                 18

<210> SEQ ID NO 12
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gln Asp Ile Arg Lys Asn
1               5

<210> SEQ ID NO 13
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13 gatgcatcc                                                            9

<210> SEQ ID NO 14
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Asp Ala Ser
1

<210> SEQ ID NO 15
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 15
caacaatatt ataatctccc attcact                                              27

<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gln Gln Tyr Tyr Asn Leu Pro Phe Thr
1               5

<210> SEQ ID NO 17
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
caggttcagc tggtgcagtc tggaactgag gtgaagaagc ctggggcctc agtaaaggtc        60
tcctgcaagg cctctggtta tacttatggt gcctatgcaa tcagctgggt gcgacaggcc       120
cctggacaag gccttgagtg gatgggatgg atcagcgctt acaatggtaa cacaaactat       180
gcacagaaat tccaggacag agtcaccatg accacagaca catccacgaa cacagcctac       240
atggaactga ggggcctaaa atctgacgac acggccgtgt atttctgtgc gagggcctgg       300
aactcctttg actactgggg ccagggcacc ctggtcactg tctcctcagc ctccaccaag       360
ggcccatcgg tcttccccct ggcgccctgc tccaggagca cctccgagag cacagccgcc       420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540
ctcagcagcg tggtgaccgt gccctccagc agcttgggca cgaagaccta cacctgcaac       600
gtagatcaca agcccagcaa caccaaggtg gacaagagag ttgagtccaa atatggtccc       660
ccatgcccac cctgcccagc acctgagttc ctggggggac catcagtctt cctgttcccc       720
ccaaaaccca aggacactct catgatctcc cggacccctg aggtcacgtg cgtggtggtg       780
gacgtgagcc aggaagaccc cgaggtccag ttcaactggt acgtggatgg cgtggaggtg       840
cataatgcca agacaaagcc gcgggaggag cagttcaaca gcacgtaccg tgtggtcagc       900
gtcctcaccg tcctgcacca ggactggctg aacggcaagg agtacaagtg caaggtctcc       960
aacaaaggcc tcccgtcctc catcgagaaa accatctcca aagccaaagg gcagccccga      1020
gagccacagg tgtacaccct gcccccatcc caggaggaga tgaccaagaa ccaggtcagc      1080
ctgacctgcc tggtcaaagg cttctacccc agcgacatcg ccgtggagtg ggagagcaat      1140
gggcagccgg agaacaacta caagaccacg cctcccgtgc tggactccga cggctccttc      1200
ttcctctaca gcaggctcac cgtggacaag agcaggtggc aggaggggaa tgtcttctca      1260
tgctccgtga tgcatgaggc tctgcacaac cactacacac agaagtccct ctccctgtct      1320
ctgggtaaat ga                                                         1332

<210> SEQ ID NO 18
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

Gln Val Gln Leu Val Gln Ser Gly Thr Glu Val Lys Lys Pro Gly Ala
1               5                   10                  15

Ser Val Lys Val Ser Cys Lys Ala Ser Gly Tyr Thr Tyr Gly Ala Tyr
            20                  25                  30

Ala Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Phe
    50                  55                  60

Gln Asp Arg Val Thr Met Thr Thr Asp Thr Ser Thr Asn Thr Ala Tyr
65                  70                  75                  80

Met Glu Leu Arg Gly Leu Lys Ser Asp Asp Thr Ala Val Tyr Phe Cys
                85                  90                  95

Ala Arg Ala Trp Asn Ser Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe

```
                    355                 360                 365
Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
                435                 440

<210> SEQ ID NO 19
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
gacatccaga tgacccagtc tccatcctcc ctgtctgcgt ctgtaggaga cagagtcacc      60
atcacttgcc aggcgagtca ggacattagg aaaaatttaa attggtatca acagaaacca    120
gggaaagccc ctaagctcct gatctccgat gcatccactt tagaaacagg ggtcccatca    180
agattcagtg gaagtggatc tgggacagat tttactttca ccatcagcag cctgcagcct    240
gaagatattg caaaatatta ctgtcaacaa tattataatc tcccattcac tttcggccct    300
gggaccaaag tggatatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 20
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Lys Asn
                20                  25                  30

Leu Asn Trp Tyr Gln Gln Lys Pro Gly Lys Ala Pro Lys Leu Leu Ile
            35                  40                  45

Ser Asp Ala Ser Thr Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Lys Tyr Tyr Cys Gln Gln Tyr Tyr Asn Leu Pro Phe
```

```
                85                  90                  95
Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 21
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
caggtgcagc tggtacagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accacggacg aatccacgag cacagcctac    240
atggagctga gcagcctgag atctgaggac acggccgtat attactgtgc gagagagggc    300
tacggtgact actacttcgg tatggacgtc tggggccaag ggaccacggt caccgtctcc    360
tca                                                                   363

<210> SEQ ID NO 22
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80
```

```
              Met Glu Leu Ser Ser Leu Arg Ser Glu Asp Thr Ala Val Tyr Tyr Cys
                              85                  90                  95

Ala Arg Glu Gly Tyr Gly Asp Tyr Tyr Phe Gly Met Asp Val Trp Gly
                          100                 105                 110

Gln Gly Thr Thr Val Thr Val Ser Ser
                      115                 120

<210> SEQ ID NO 23
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
ggaggcacct tcagcagcta tgct                                              24

<210> SEQ ID NO 24
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Gly Thr Phe Ser Ser Tyr Ala
 1               5

<210> SEQ ID NO 25
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
atcatcccta tctttggtac agca                                              24

<210> SEQ ID NO 26
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ile Ile Pro Ile Phe Gly Thr Ala
 1               5

<210> SEQ ID NO 27
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
```
gcgagagagg gctacggtga ctactacttc ggtatggacg tc                42

<210> SEQ ID NO 28
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ala Arg Glu Gly Tyr Gly Asp Tyr Tyr Phe Gly Met Asp Val
1               5                   10

<210> SEQ ID NO 29
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29
gatgttgtga tgactcagtc tccactctcc ctgcccgtca cccttggaca gccggcctcc    60
atctcctgca ggtctagtca aagcctcgta tacagtgatg aaacacccta cttgaattgg   120
tttcagcaga ggccagacca atctccaagg cgcctaattt ataagatttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggcct   300
cccactttgg ccaggggac caagctggag atcaaa                              336

<210> SEQ ID NO 30
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Asp Gln Ser
        35                  40                  45

Pro Arg Arg Leu Ile Tyr Lys Ile Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Leu Glu Ile Lys
            100                 105                 110

<210> SEQ ID NO 31
<211> LENGTH: 33
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 31
caaagcctcg tatacagtga tggaaacacc tac                              33

<210> SEQ ID NO 32
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gln Ser Leu Val Tyr Ser Asp Gly Asn Thr Tyr
1               5                   10

<210> SEQ ID NO 33
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33 aagatttct                                                          9

<210> SEQ ID NO 34
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Lys Ile Ser
1

<210> SEQ ID NO 35
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
atgcaaggta cacactggcc tcccact                                     27

<210> SEQ ID NO 36
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36
```

Met Gln Gly Thr His Trp Pro Pro Thr
1               5

<210> SEQ ID NO 37
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37

| | | | | | |
|---|---|---|---|---|---|
| caggtgcagc | tggtacagtc | tggggctgag | gtgaagaagc | ctgggtcctc | ggtgaaggtc | 60 |
| tcctgcaagg | cttctggagg | caccttcagc | agctatgcta | tcagctgggt | gcgacaggcc | 120 |
| cctggacaag | gcttgagtg | gatgggaggg | atcatccta | tctttggtac | agcaaactac | 180 |
| gcacagaagt | tccagggcag | agtcacgatt | accacggacg | aatccacgag | cacagcctac | 240 |
| atggagctga | gcagcctgag | atctgaggac | acggccgtat | attactgtgc | gagagaggc | 300 |
| tacggtgact | actacttcgg | tatggacgtc | tggggccaag | ggaccacggt | caccgtctcc | 360 |
| tcagcctcca | ccaagggccc | atcggtcttc | cccctggcgc | cctgctccag | gagcacctcc | 420 |
| gagagcacag | ccgccctggg | ctgcctggtc | aaggactact | tccccgaacc | ggtgacggtg | 480 |
| tcgtggaact | caggcgccct | gaccagcggc | gtgcacacct | tcccggctgt | cctacagtcc | 540 |
| tcaggactct | actccctcag | cagcgtggtg | accgtgccct | ccagcagctt | gggcacgaag | 600 |
| acctacacct | gcaacgtaga | tcacaagccc | agcaacacca | aggtggacaa | gagagttgag | 660 |
| tccaaatatg | gtcccccatg | cccaccctgc | ccagcacctg | agttcctggg | gggaccatca | 720 |
| gtcttcctgt | tccccccaaa | acccaaggac | actctcatga | tctcccggac | ccctgaggtc | 780 |
| acgtgcgtgg | tggtggacgt | gagccaggaa | gaccccgagg | tccagttcaa | ctggtacgtg | 840 |
| gatggcgtgg | aggtgcataa | tgccaagaca | aagccgcggg | aggagcagtt | caacagcacg | 900 |
| taccgtgtgg | tcagcgtcct | caccgtcctg | caccaggact | ggctgaacgg | caaggagtac | 960 |
| aagtgcaagg | tctccaacaa | aggcctcccg | tcctccatcg | agaaaaccat | ctccaaagcc | 1020 |
| aaagggcagc | cccgagagcc | acaggtgtac | accctgcccc | catcccagga | ggagatgacc | 1080 |
| aagaaccagg | tcagcctgac | ctgcctggtc | aaaggcttct | accccagcga | catcgccgtg | 1140 |
| gagtgggaga | gcaatgggca | gccggagaac | aactacaaga | ccacgcctcc | cgtgctggac | 1200 |
| tccgacggct | ccttcttcct | ctacagcagg | ctcaccgtgg | acaagagcag | gtggcaggag | 1260 |
| gggaatgtct | tctcatgctc | cgtgatgcat | gaggctctgc | acaaccacta | cacacagaag | 1320 |
| tccctctccc | tgtctctggg | taaatga | | | | 1347 |

<210> SEQ ID NO 38
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

-continued

```
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
 50                  55                  60
Gln Gly Arg Val Thr Ile Thr Thr Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Glu Gly Tyr Gly Asp Tyr Tyr Phe Gly Met Asp Val Trp Gly
                100                 105                 110
Gln Gly Thr Thr Val Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
        195                 200                 205
Lys Pro Ser Asn Thr Lys Val Asp Lys Arg Val Glu Ser Lys Tyr Gly
210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly Lys
        435                 440                 445
```

```
<210> SEQ ID NO 39
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39
gatgttgtga tgactcagtc tccactctcc ctgcccgtca cccttggaca gccggcctcc      60
atctcctgca ggtctagtca aagcctcgta tacagtgatg aaacaccta cttgaattgg     120 tttcagcaga ggccagacca atctccaagg cgcctaattt ataagatttc taaccgggac     180
tctggggtcc cagacagatt cagcggcagt gggtcaggca ctgatttcac actgaaaatc     240
agcagggtgg aggctgagga tgttggggtt tattactgca tgcaaggtac acactggcct     300 cccactttg gccaggggac caagctggag atcaaacgaa ctgtggctgc accatctgtc      360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 40
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Asp Gln Ser
        35                  40                  45

Pro Arg Arg Leu Ile Tyr Lys Ile Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
```

-continued

```
                180               185               190
Lys His Lys Val Tyr Ala Cys Glu Val Thr His Gln Gly Leu Ser Ser
        195               200               205

Pro Val Thr Lys Ser Phe Asn Arg Gly Glu Cys
        210               215

<210> SEQ ID NO 41
<211> LENGTH: 241
<212> TYPE: PRT
<213> ORGANISM: Homo sapiens

<400> SEQUENCE: 41

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala
```